(12) United States Patent
Wahlestedt

(10) Patent No.: US 10,472,627 B2
(45) Date of Patent: *Nov. 12, 2019

(54) NATURAL ANTISENSE AND NON-CODING RNA TRANSCRIPTS AS DRUG TARGETS

(71) Applicant: The Scripps Research Institute, La Jolla, CA (US)

(72) Inventor: Claes Wahlestedt, Palm Beach, FL (US)

(73) Assignee: The Scripps Research Institute, La Jolla, CA (US)

( * ) Notice: Subject to any disclaimer, the term of this patent is extended or adjusted under 35 U.S.C. 154(b) by 21 days.

This patent is subject to a terminal disclaimer.

(21) Appl. No.: 15/716,093

(22) Filed: Sep. 26, 2017

(65) Prior Publication Data

US 2018/0148721 A1 May 31, 2018

Related U.S. Application Data

(60) Division of application No. 13/563,581, filed on Jul. 31, 2012, now Pat. No. 9,803,195, which is a continuation of application No. 12/159,607, filed as application No. PCT/US2006/062672 on Dec. 28, 2006, now Pat. No. 8,288,354.

(60) Provisional application No. 60/754,463, filed on Dec. 28, 2005.

(51) Int. Cl.
C12N 15/113 (2010.01)

(52) U.S. Cl.
CPC ...... *C12N 15/113* (2013.01); *C12N 2310/111* (2013.01); *C12N 2310/14* (2013.01); *C12N 2330/10* (2013.01)

(58) Field of Classification Search
None
See application file for complete search history.

(56) References Cited

U.S. PATENT DOCUMENTS

| | | |
|---|---|---|
| 3,687,808 A | 8/1972 | Merigan, Jr. et al. |
| 4,469,863 A | 9/1984 | Ts'o et al. |
| 4,476,301 A | 10/1984 | Imbach et al. |
| 4,683,195 A | 7/1987 | Mullis et al. |
| 4,683,202 A | 7/1987 | Mullis |
| 4,754,065 A | 6/1988 | Levenson et al. |
| 4,800,159 A | 1/1989 | Mullis et al. |
| 4,828,979 A | 5/1989 | Klevan et al. |
| 4,845,205 A | 7/1989 | Huynh et al. |
| 4,948,882 A | 8/1990 | Ruth |
| 4,981,957 A | 1/1991 | Lebleu et al. |
| 5,013,830 A | 5/1991 | Ohtsuka et al. |
| 5,023,243 A | 6/1991 | Tullis |
| 5,034,506 A | 7/1991 | Summerton et al. |
| 5,118,800 A | 6/1992 | Smith et al. |
| 5,130,302 A | 7/1992 | Spielvogel et al. |
| 5,134,066 A | 7/1992 | Rogers et al. |
| 5,138,045 A | 8/1992 | Cook et al. |
| 5,149,797 A | 9/1992 | Pederson et al. |
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,185,444 A | 2/1993 | Summerton et al. |
| 5,188,897 A | 2/1993 | Suhadolnik et al. |
| 5,214,134 A | 5/1993 | Weis et al. |
| 5,216,141 A | 6/1993 | Benner |
| 5,218,105 A | 6/1993 | Cook et al. |
| 5,220,007 A | 6/1993 | Pederson et al. |
| 5,235,033 A | 8/1993 | Summerton et al. |
| 5,256,775 A | 10/1993 | Froehler |
| 5,264,562 A | 11/1993 | Matteucci |
| 5,264,564 A | 11/1993 | Matteucci |
| 5,276,019 A | 1/1994 | Cohen et al. |
| 5,278,302 A | 1/1994 | Caruthers et al. |
| 5,286,717 A | 2/1994 | Cohen et al. |
| 5,288,512 A | 2/1994 | Seiden |
| 5,288,514 A | 2/1994 | Ellman |
| 5,319,080 A | 6/1994 | Leumann |
| 5,321,131 A | 6/1994 | Agrawal et al. |
| 5,359,044 A | 10/1994 | Cook et al. |
| 5,366,878 A | 11/1994 | Pederson et al. |
| 5,367,066 A | 11/1994 | Urdea et al. |
| 5,393,878 A | 2/1995 | Leumann |
| 5,399,676 A | 3/1995 | Froehler |
| 5,403,711 A | 4/1995 | Walder et al. |
| 5,405,938 A | 4/1995 | Summerton et al. |
| 5,405,939 A | 4/1995 | Suhadolnik et al. |
| 5,432,272 A | 7/1995 | Benner |

(Continued)

FOREIGN PATENT DOCUMENTS

| | | |
|---|---|---|
| CA | 2686933 A1 | 10/2008 |
| CN | 104583405 A | 4/2015 |

(Continued)

OTHER PUBLICATIONS

New England Biolabs Catalog 1998/99, p. 121. (Year: 1998).*

(Continued)

*Primary Examiner* — J. E. Angell

(74) *Attorney, Agent, or Firm* — Wilson Sonsini Goodrich & Rosati

(57) ABSTRACT

Small interfering RNA (siRNA) knock down antisense transcripts, and regulate the expression of their sense partners. This regulation can either be discordant (antisense knockdown results in sense transcript elevation) or concordant (antisense knockdown results in concomitant sense transcript reduction).

16 Claims, 23 Drawing Sheets

Specification includes a Sequence Listing.

(56) References Cited

U.S. PATENT DOCUMENTS

| | | |
|---|---|---|
| 5,434,257 A | 7/1995 | Matteucci et al. |
| 5,446,137 A | 8/1995 | Maag et al. |
| 5,453,496 A | 9/1995 | Caruthers et al. |
| 5,455,233 A | 10/1995 | Spielvogel et al. |
| 5,457,187 A | 10/1995 | Gmeiner et al. |
| 5,459,255 A | 10/1995 | Cook et al. |
| 5,466,677 A | 11/1995 | Baxter et al. |
| 5,466,786 A | 11/1995 | Buhr et al. |
| 5,470,967 A | 11/1995 | Huie et al. |
| 5,474,796 A | 12/1995 | Brennan |
| 5,476,925 A | 12/1995 | Letsinger et al. |
| 5,484,908 A | 1/1996 | Froehler et al. |
| 5,489,677 A | 2/1996 | Sanghvi et al. |
| 5,491,084 A | 2/1996 | Chalfie et al. |
| 5,491,133 A | 2/1996 | Walder et al. |
| 5,502,177 A | 3/1996 | Matteucci et al. |
| 5,506,337 A | 4/1996 | Summerton et al. |
| 5,514,785 A | 5/1996 | Van Ness et al. |
| 5,519,126 A | 5/1996 | Hecht |
| 5,519,134 A | 5/1996 | Acevedo et al. |
| 5,525,465 A | 6/1996 | Haralambidis et al. |
| 5,525,711 A | 6/1996 | Hawkins et al. |
| 5,525,735 A | 6/1996 | Gallop et al. |
| 5,536,821 A | 7/1996 | Agrawal et al. |
| 5,539,082 A | 7/1996 | Nielsen et al. |
| 5,539,083 A | 7/1996 | Cook et al. |
| 5,541,306 A | 7/1996 | Agrawal et al. |
| 5,541,307 A | 7/1996 | Cook et al. |
| 5,541,313 A | 7/1996 | Ruth |
| 5,545,730 A | 8/1996 | Urdea et al. |
| 5,549,974 A | 8/1996 | Holmes |
| 5,550,111 A | 8/1996 | Suhadolnik et al. |
| 5,552,538 A | 9/1996 | Urdea et al. |
| 5,552,540 A | 9/1996 | Haralambidis |
| 5,561,225 A | 10/1996 | Maddry et al. |
| 5,563,253 A | 10/1996 | Agrawal et al. |
| 5,565,350 A | 10/1996 | Kmiec |
| 5,567,811 A | 10/1996 | Misiura et al. |
| 5,569,588 A | 10/1996 | Ashby et al. |
| 5,571,799 A | 11/1996 | Tkachuk et al. |
| 5,576,427 A | 11/1996 | Cook et al. |
| 5,587,361 A | 12/1996 | Cook et al. |
| 5,587,469 A | 12/1996 | Cook et al. |
| 5,591,722 A | 1/1997 | Montgomery et al. |
| 5,593,853 A | 1/1997 | Chen et al. |
| 5,596,086 A | 1/1997 | Matteucci et al. |
| 5,596,091 A | 1/1997 | Switzer |
| 5,597,909 A | 1/1997 | Urdea et al. |
| 5,602,240 A | 2/1997 | De Mesmaeker et al. |
| 5,605,662 A | 2/1997 | Heller et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |
| 5,623,065 A | 4/1997 | Cook et al. |
| 5,623,070 A | 4/1997 | Cook et al. |
| 5,625,050 A | 4/1997 | Beaton et al. |
| 5,627,053 A | 5/1997 | Usman et al. |
| 5,633,360 A | 5/1997 | Bischofberger et al. |
| 5,639,873 A | 6/1997 | Barascut et al. |
| 5,646,265 A | 7/1997 | McGee |
| 5,652,355 A | 7/1997 | Metelev et al. |
| 5,652,356 A | 7/1997 | Agrawal |
| 5,658,873 A | 8/1997 | Bertsch-Frank et al. |
| 5,663,312 A | 9/1997 | Chaturvedula |
| 5,670,633 A | 9/1997 | Cook et al. |
| 5,677,437 A | 10/1997 | Teng et al. |
| 5,677,439 A | 10/1997 | Weis et al. |
| 5,681,941 A | 10/1997 | Cook et al. |
| 5,700,920 A | 12/1997 | Altmann et al. |
| 5,700,922 A | 12/1997 | Cook |
| 5,714,331 A | 2/1998 | Buchardt et al. |
| 5,719,262 A | 2/1998 | Buchardt et al. |
| 5,750,692 A | 5/1998 | Cook et al. |
| 5,998,148 A | 12/1999 | Bennett et al. |
| 6,175,409 B1 | 1/2001 | Nielsen et al. |
| 6,221,587 B1 | 4/2001 | Ecker et al. |
| 6,239,265 B1 | 5/2001 | Cook |
| 6,242,589 B1 | 6/2001 | Cook et al. |
| 6,268,490 B1 | 7/2001 | Imanishi et al. |
| 6,303,374 B1 | 10/2001 | Zhang et al. |
| 6,307,040 B1 | 10/2001 | Cook et al. |
| 6,316,198 B1 | 11/2001 | Skouv et al. |
| 6,335,434 B1 | 1/2002 | Guzaev et al. |
| 6,376,541 B1 | 4/2002 | Nixon et al. |
| 6,403,566 B1 | 6/2002 | Wang |
| 6,444,464 B1 | 9/2002 | Wyatt |
| 6,451,991 B1 | 9/2002 | Martin et al. |
| 6,525,191 B1 | 2/2003 | Ramasamy |
| 6,528,262 B1 | 3/2003 | Gilad et al. |
| 6,528,631 B1 | 3/2003 | Cook et al. |
| 6,617,122 B1 | 9/2003 | Hayden et al. |
| 6,617,442 B1 | 9/2003 | Crooke et al. |
| 6,630,315 B1 | 10/2003 | Miwa et al. |
| 6,639,059 B1 | 10/2003 | Kochkine et al. |
| 6,656,730 B1 | 12/2003 | Manoharan |
| 6,667,337 B2 | 12/2003 | Wilson |
| 6,670,461 B1 | 12/2003 | Wengel et al. |
| 6,710,174 B2 | 3/2004 | Bennett et al. |
| 6,734,291 B2 | 5/2004 | Kochkine et al. |
| 6,762,169 B1 | 7/2004 | Manoharan |
| 6,794,499 B2 | 9/2004 | Wengel et al. |
| 6,833,361 B2 | 12/2004 | Wang; Guangyi et al. |
| 6,861,514 B2 | 3/2005 | Cook et al. |
| 6,867,294 B1 | 3/2005 | Sanghvi et al. |
| 6,936,467 B2 | 8/2005 | Kmiec et al. |
| 6,936,593 B1 | 8/2005 | Agrawal et al. |
| 6,977,295 B2 | 12/2005 | Belotserkovskii et al. |
| 6,986,988 B2 | 1/2006 | Gilad et al. |
| 7,034,133 B2 | 4/2006 | Wengel et al. |
| 7,034,145 B2 | 4/2006 | Shen et al. |
| 7,053,195 B1 | 5/2006 | Goff |
| 7,053,199 B2 | 5/2006 | Imanishi et al. |
| 7,053,207 B2 | 5/2006 | Wengel |
| 7,060,809 B2 | 6/2006 | Wengel et al. |
| 7,084,125 B2 | 8/2006 | Wengel |
| 7,087,589 B2 | 8/2006 | Jacobson et al. |
| 7,125,982 B1 | 10/2006 | Frayne |
| 7,144,995 B2 | 12/2006 | Wise et al. |
| 7,144,999 B2 | 12/2006 | Ward et al. |
| 7,148,204 B2 | 12/2006 | Bennett et al. |
| 7,153,954 B2 | 12/2006 | Koch et al. |
| 7,169,916 B2 | 1/2007 | Krotz et al. |
| 7,199,107 B2 | 4/2007 | Dobie et al. |
| 7,202,357 B2 | 4/2007 | Crooke et al. |
| 7,217,572 B2 | 5/2007 | Ward et al. |
| 7,220,549 B2 | 5/2007 | Buzby et al. |
| 7,226,785 B2 | 6/2007 | Kmiec et al. |
| 7,229,974 B2 | 6/2007 | Peyman et al. |
| 7,229,976 B2 | 6/2007 | Dobie et al. |
| 7,235,534 B2 | 6/2007 | Tanguay et al. |
| 7,235,653 B2 | 6/2007 | Bennett et al. |
| 7,238,858 B2 | 7/2007 | Marraccini et al. |
| 7,276,599 B2 | 10/2007 | Moore et al. |
| 7,285,288 B1 | 10/2007 | Tormo et al. |
| 7,297,786 B2 | 11/2007 | McCray et al. |
| 7,314,923 B2 | 1/2008 | Kaneko et al. |
| 7,320,965 B2 | 1/2008 | Sah et al. |
| 7,321,828 B2 | 1/2008 | Cowsert et al. |
| 7,335,764 B2 | 2/2008 | Crooke et al. |
| 7,335,765 B2 | 2/2008 | Kaneko et al. |
| 7,339,051 B2 | 3/2008 | Crooke et al. |
| 7,371,833 B1 | 5/2008 | Weiss |
| 7,399,845 B2 | 7/2008 | Swayze et al. |
| 7,402,434 B2 | 7/2008 | Newman et al. |
| 7,402,574 B2 | 7/2008 | Iversen et al. |
| 7,420,050 B2 | 9/2008 | Park et al. |
| 7,423,142 B2 | 9/2008 | Vornlocher |
| 7,425,545 B2 | 9/2008 | Crooke et al. |
| 7,427,675 B2 | 9/2008 | Capaldi et al. |
| 7,456,154 B2 | 11/2008 | Soreq et al. |
| 7,462,642 B2 | 12/2008 | Wang et al. |
| 7,468,431 B2 | 12/2008 | Bhanot et al. |

(56) References Cited

U.S. PATENT DOCUMENTS

| | | |
|---|---|---|
| 7,510,830 B2 | 3/2009 | Baguley et al. |
| 7,541,344 B2 | 6/2009 | Bhat et al. |
| 7,547,684 B2 | 6/2009 | Seth et al. |
| 7,569,575 B2 | 8/2009 | Soerensen et al. |
| 7,569,686 B1 | 8/2009 | Bhat et al. |
| 7,572,582 B2 | 8/2009 | Wengel et al. |
| 7,582,745 B2 | 9/2009 | Sah et al. |
| 7,585,893 B2 | 9/2009 | Baguley et al. |
| 7,589,190 B2 | 9/2009 | Westergaard et al. |
| 7,598,227 B2 | 10/2009 | Crooke et al. |
| 7,605,251 B2 | 10/2009 | Tan et al. |
| 7,622,453 B2 | 11/2009 | Frieden et al. |
| 7,662,948 B2 | 2/2010 | Kurreck et al. |
| 7,666,854 B2 | 2/2010 | Seth et al. |
| 7,674,895 B2 | 3/2010 | Reich et al. |
| 7,687,617 B2 | 3/2010 | Thrue et al. |
| 7,691,995 B2 | 4/2010 | Zamore et al. |
| 7,695,902 B2 | 4/2010 | Crooke |
| 7,696,345 B2 | 4/2010 | Allerson et al. |
| 7,709,456 B2 | 5/2010 | Corey et al. |
| 7,709,630 B2 | 5/2010 | Gaarde et al. |
| 7,713,738 B2 | 5/2010 | Hansen et al. |
| 7,718,629 B2 | 5/2010 | Bumcrot et al. |
| 7,723,508 B2 | 5/2010 | Crooke et al. |
| 7,732,422 B2 | 6/2010 | Gleave et al. |
| 7,732,590 B2 | 6/2010 | Bhanot et al. |
| 7,737,264 B2 | 6/2010 | Thrue et al. |
| 7,737,265 B2 | 6/2010 | Akinc et al. |
| 7,741,305 B2 | 6/2010 | Crooke et al. |
| 7,741,309 B2 | 6/2010 | Hansen et al. |
| 7,741,457 B2 | 6/2010 | Swayze et al. |
| 7,745,609 B2 | 6/2010 | Bennett et al. |
| 7,749,978 B2 | 7/2010 | Sah et al. |
| 8,288,354 B2 * | 10/2012 | Wahlestedt .......... C12N 15/113 514/44 A |
| 8,557,960 B2 | 10/2013 | Kim et al. |
| 8,815,808 B2 | 8/2014 | Nykjaer et al. |
| 9,074,210 B2 | 7/2015 | Collard et al. |
| 9,803,195 B2 | 10/2017 | Wahlestedt et al. |
| 10,214,745 B2 | 2/2019 | Faghihi et al. |
| 2003/0139359 A1 | 7/2003 | Dobie |
| 2003/0186920 A1 | 10/2003 | Sirois |
| 2003/0190635 A1 | 10/2003 | McSwiggen |
| 2003/0191075 A1 | 10/2003 | Cook et al. |
| 2003/0228618 A1 | 12/2003 | Levanon et al. |
| 2003/0233670 A1 | 12/2003 | Edgerton et al. |
| 2004/0006031 A1 | 1/2004 | Dean et al. |
| 2004/0033480 A1 | 2/2004 | Wong |
| 2004/0101858 A1 | 5/2004 | Ward et al. |
| 2004/0132680 A1 | 7/2004 | Wong et al. |
| 2004/0137423 A1 | 7/2004 | Hayden et al. |
| 2004/0138156 A1 | 7/2004 | Schneider et al. |
| 2004/0175803 A1 | 9/2004 | Meritet et al. |
| 2004/0180336 A1 | 9/2004 | Gilad et al. |
| 2004/0248231 A1 | 12/2004 | Cordell et al. |
| 2004/0254137 A1 | 12/2004 | Ackermann et al. |
| 2004/0259247 A1 | 12/2004 | Tuschl et al. |
| 2005/0009771 A1 | 1/2005 | Levanon et al. |
| 2005/0026160 A1 | 2/2005 | Allerson et al. |
| 2005/0048641 A1 | 3/2005 | Hildebrand et al. |
| 2005/0113326 A1 | 5/2005 | Siwkowski et al. |
| 2005/0143357 A1 | 6/2005 | Pousette et al. |
| 2005/0153286 A1 | 7/2005 | Clements |
| 2005/0209179 A1 | 9/2005 | McSwiggen et al. |
| 2005/0215504 A1 | 9/2005 | Bennett et al. |
| 2005/0222029 A1 | 10/2005 | Bartel et al. |
| 2006/0009410 A1 | 1/2006 | Crooke et al. |
| 2006/0142196 A1 | 6/2006 | Klein et al. |
| 2006/0178333 A1 | 8/2006 | Soreq et al. |
| 2007/0082848 A1 | 4/2007 | Alitalo et al. |
| 2007/0197459 A1 | 8/2007 | Milner et al. |
| 2007/0213274 A1 | 9/2007 | Salonen |
| 2007/0213292 A1 | 9/2007 | Stoffel et al. |
| 2007/0248590 A1 | 10/2007 | Milne et al. |
| 2008/0146788 A1 | 6/2008 | Bhat et al. |
| 2008/0168574 A1 | 7/2008 | Barry et al. |
| 2008/0221051 A1 | 9/2008 | Becker et al. |
| 2008/0234197 A1 | 9/2008 | Allam et al. |
| 2008/0293142 A1 | 11/2008 | Liu et al. |
| 2009/0110661 A1 | 4/2009 | Musatov |
| 2009/0191263 A1 | 7/2009 | Reich et al. |
| 2009/0192106 A1 | 7/2009 | Dobie et al. |
| 2009/0208479 A1 | 8/2009 | Jaye et al. |
| 2009/0214637 A1 | 8/2009 | Musatov |
| 2009/0258925 A1 | 10/2009 | Wahlestedt |
| 2009/0318536 A1 | 12/2009 | Freier et al. |
| 2009/0326041 A1 | 12/2009 | Bhanot et al. |
| 2010/0105760 A1 | 4/2010 | Collard et al. |
| 2011/0274718 A1 | 11/2011 | During et al. |
| 2011/0288160 A1 | 11/2011 | During et al. |
| 2011/0319475 A1 | 12/2011 | Collard et al. |
| 2012/0208747 A1 | 8/2012 | Kim et al. |
| 2015/0031750 A1 | 1/2015 | Faghihi et al. |
| 2017/0211071 A1 | 7/2017 | Faghihi et al. |

FOREIGN PATENT DOCUMENTS

| | | | |
|---|---|---|---|
| EP | 0335451 A2 | 10/1989 | |
| EP | 0335451 A3 | 10/1989 | |
| EP | 0910399 B1 | 9/2002 | |
| EP | 2825648 A2 | 1/2015 | |
| EP | 2396038 B1 | 10/2015 | |
| WO | WO-8403564 A1 | 9/1984 | |
| WO | WO-9119735 A1 | 12/1991 | |
| WO | WO-9200091 A1 | 1/1992 | |
| WO | WO-9208796 A1 | 5/1992 | |
| WO | WO-9320242 A1 | 10/1993 | |
| WO | WO-9426887 A1 | 11/1994 | |
| WO | WO-9428143 A1 | 12/1994 | |
| WO | WO-9515373 A2 | 6/1995 | |
| WO | WO-9522618 A1 | 8/1995 | |
| WO | WO-9525116 A2 | 9/1995 | |
| WO | WO-9535505 A1 | 12/1995 | |
| WO | WO-9627663 A2 | 9/1996 | |
| WO | WO-9739120 A2 | 10/1997 | |
| WO | WO-9745135 A1 | 12/1997 | |
| WO | WO-9914226 A2 | 3/1999 | |
| WO | WO-9918952 A1 * | 4/1999 | ............. A61K 31/35 |
| WO | WO-9939352 A1 | 8/1999 | |
| WO | WO-0057837 A2 | 10/2000 | |
| WO | WO-0061770 A2 | 10/2000 | |
| WO | WO-0100669 A2 | 1/2001 | |
| WO | WO-0121631 A2 | 3/2001 | |
| WO | WO-0125488 A2 | 4/2001 | |
| WO | WO-0151630 A1 | 7/2001 | |
| WO | WO-02062840 A1 | 8/2002 | |
| WO | WO-02068688 A1 | 9/2002 | |
| WO | WO-02085308 A2 | 10/2002 | |
| WO | WO-2004016255 A1 | 2/2004 | |
| WO | WO-2004024079 A2 | 3/2004 | |
| WO | WO-2004030750 A1 | 4/2004 | |
| WO | WO-2004041838 A1 | 5/2004 | |
| WO | WO-2004104161 A2 | 12/2004 | |
| WO | WO-2005045034 A2 | 5/2005 | |
| WO | WO-2005070136 A2 | 8/2005 | |
| WO | WO-2005079862 A1 | 9/2005 | |
| WO | WO-2007028065 A2 | 3/2007 | |
| WO | WO-2007071182 A1 | 6/2007 | |
| WO | WO-2007087113 A2 | 8/2007 | |
| WO | WO-2007138023 A1 | 12/2007 | |
| WO | WO-2008057556 A2 | 5/2008 | |
| WO | WO-2008066672 A2 | 6/2008 | |
| WO | WO-2008087561 A2 | 7/2008 | |
| WO | WO-2009058970 A2 | 5/2009 | |
| WO | WO-2010002984 A1 | 1/2010 | |
| WO | WO-2010040571 A2 | 4/2010 | |
| WO | WO-2010054364 A1 | 5/2010 | |
| WO | WO-2010058227 A2 | 5/2010 | |
| WO | WO-2010093904 A2 | 8/2010 | |

(56) References Cited

FOREIGN PATENT DOCUMENTS

| WO | WO-2012068340 A2 | 5/2012 |
|----|------------------|--------|
| WO | WO-2013138374 A2 | 9/2013 |

OTHER PUBLICATIONS

Chan et al. The complexity of antisense transcription revealed by the study of developing male germ cells. Genomics 87:681-692 (2006).
Russia Patent Application No. 2014140112 Office Action dated Nov. 29, 2017.
Russia Patent Application No. 2014140112 Office Action dated Feb. 17, 2018.
Ausubel, Current Protocols in Molecular Biology vol. 1, 6.0.1-6.4.10 (1994).
Barak, et al., "A p-Arrestin/Green Fluorescent Protein Biosensor for Detecting G Protein-Coupled Receptor Activation," J. Biol. Chem. 272:27497-27500 (1997).
Barber, et al., "Delivery of membrane-impermeant fluorescent probes into living neural cell populations by lipotransfer," Neuroscience Letters 207:17-20 (1996).
Baum, "Solid-phase synthesis of benzodiazepines," C&EN News, Jan. 18, p. 33-34 (1993).
Bernstein, E., et al., "Role for a bidentate ribonuclease in the initiation step of RNA interference," Nature 409:363-366 (2001).
Boutla, A., et al., "Short 5'-phosphorylated double-stranded RNAs induce RNA interference in *Drosophila*," Curr. Biol. 11:1776-1780 (2001).
Boyd-Kimball, et al., "Proteomic Identification of Proteins Specifically Oxidized by Intracerebral Injection of Amyloid β-Peptide (1-42) into Rat Brain: Implications for Alzheimer's Disease," Neuroscience 132, 313-324 (2005).
Brazma & Vilo, "Gene expression data analysis," FEBS Lett., 480:17-24 (2000).
Bright, et al., "Chapter 6. Fluorescence Ratio Imaging Microscopy," Methods in Cell Biology vol. 30, Taylor and Wang (eds) p. 157-192 (1989).
Bright, et al., "Delivery of Macromolecules Into Adherent Cells via Electroporation for Use in Fluorescence Spectroscopic Imaging and Metabolic Studies," Cytometry 24:226-233 (1996).
Bright, et al., "Fluorescence Ratio Imaging Microscopy: Temporal and Spatial Measurements of Cytoplasmic pH," J. Cell Biology 104:1019-1033 (1989).
Campbell, et al., "Phosphonate Ester Synthesis Using a Modified Mitsunobu Condensation," J. Org. Chem. 59:658-660 (1994).
Caplen, N. J., et al., "Specific inhibition of gene expression by small double-stranded RNAs in invertebrate and vertebrate systems," PNAS 98(17):9742-9747 (2001).
Carninci, et al., "The transcriptional landscape of the mammalian genome," Science 309:1559-1563 (2005).
Carulli, et al., "High Throughput Analysis of Differential Gene Expression," J. Cell Biochem. Suppl., 3:286-296 (1998).
Cech, T., "Ribozymes and Their Medical Implications," American. Med Assoc. 260:3030-3035 (1988).
Celts, et al., "Gene expression profiling: monitoring transcription and translation products using DNA microarrays and proteomics," FEBS Lett., 480:2-16 (2000).
Chabala, J.C., "Solid-phase combinatorial chemistry and novel tagging methods for identifying leads," Curr Opin Biotechnol. 6:632-639 (1995).
Chen, et al., "Analogous Organic Synthesis of Small-Compound Libraries: Validation of Combinatorial Chemistry in Small-Molecule Synthesis," J. Amer. Chem. Soc. 116:2661-2662 (1994).
Chen, et al., "Expression of ssDNA in Mammalian Cells," BioTechniques 34:167-171 (2003).
Cheng, J. et al., "Transcriptional maps of 10 human chromosomes at 5-nucleotide resolution," Science 308:5725:1149-1154 (2005).
Chinese Patent Application No. 201380024874.4 First Office Action dated Feb. 2, 2016.
Chinese Patent Application No. 201380024874.4 Office Action dated Oct. 11, 2017.
Chinese Patent Application No. 2013800248744 Second Office Action dated Dec. 20, 2016.
Cho et al. An Unnatural Biopolymer. Science 261:1303-1305 (1993).
Christiensen, N.K. et al., "A Novel Class of Oligonucleotide Analogues Containing 2'-O,3'-C-Linked [3.2.0]Bicycloarabinonucleoside Monomers: Synthesis, Thermal Affinity Studies, and Molecular Modeling," J. Am. Chem. Soc., 120:5458-5463 (1998).
Cubitt, et al. , "Understanding, improving and using green fluorescent proteins," Trends in Biochemical Science 20:448-455 (1995).
Curiel et al. Adenovirus enhancement of transferrin-polylysine-mediated gene delivery. PNAS USA 88:8850-8854 (1991).
Dai et al., "SIRT1 Interacts With p73 and Suppresses p73-Dependent Transcriptional Activity," J Cell Physiol 210(1):161-165 (2007).
Davidson, et al., "A model system for in vivo gene transfer into the central nervous system using an adenoviral vector," Nat. Genet 3:219-223 (1993).
Davis, et al., "Direct Gene Transfer into Skeletal Muscle In Vivo: Factors Affecting Efficiency of Transfer and Stability of Expression," Hum Gene Ther 4:151-159 (1993).
De Mesmaeker, et al., "Antisense Oligonucleotides," Acc. Chem. Res. 28:366-374 (1995).
Deng, et al., "Small interfering RNA targeting the PINK I induces apoptosis in dopaminergic cells SH-SY5Y" Biochemical and Biophysical Research Communications, vol. 337, No. 4, pp. 1133-1138 (2005).
Dixon, et al., "Anthrax," New England J. Med. 341:815-826 (1999).
Dolle, "Discovery of Enzyme inhibitors through combinatorial chemistry," Mol Divers. 2:223-236 (1997).
Dykxhoom, et al., "Determinants of specific RNA interference-mediated silencing of human β-globin alleles differing by a single nucleotide polymorphism." PNAS, 103:15, 5953-5958 (2006).
Eguchi, et al., "Antisense RNA," Annu. Rev. Biochem 60:631-652 (1991).
Eichler, et al., "Generation and utilization of synthetic combinatorial libraries," Mol Med Today 1:174-180 (1995).
Eichler, et al., "Peptide Peptidomimetic and organic synthetic combinatorial libraries," Med Res Rev 15:481-496 (1995).
Englisch et al., 'Angewandle Chemie, International Edition', #613, P. A-115 (1991).
Espeseth, et al., A genome wide analysis of ubiquitin ligases in APP processing identifies a novel regulator of BACE1 mRNA levels, Mol. Cell Neurosci. 33: 227-235 (2006).
European Patent Application No. 06850393.7 Examination Report dated Oct. 18, 2011.
European Patent Application No. 13712635.5 Communication dated Jan. 13, 2016.
European Patent Application No. 13712635.5 Communication dated Jan. 19, 2017.
Faghihi et al., "Evidence for natural antisense transcript-mediated inhibition of microRNA function," Genome Biology 11:R56, 13 pgs (2010).
Faghihi et al., "Expression of a noncoding RNA is elevated in Alzheimer's disease and drives rapid feed-forward regulation of B-secretase expression," Nat. Med. 14(7):723-730 (2008).
Faghihi, M. & Wahlestedt, C., "RNA interference is not involved in natural antisense mediated regulation of gene expression in mammals," Genome Biol (2005).
Fauchere, et al., "Peptide and nonpeptide lead discovery using robotically synthesized soluble libraries," Can J. Physiol Pharmacol 75:683-689 (1997).
Felgner and Holm, "Cationic Liposome-Mediated Transfection," Bethesda Res. Lab Focus, 11:2:21 (1989).
Fields, et al., "How many genes in the human genome?" Nature Genetics 7:345-346 (1994).
Freier & Altman, "The ups and downs of nucleic acid duplex stability: structure-stability studies on chemically-modified DNA:RNA duplexes," Nucl. Acid Res., 25:22:4429-4443 (1997).
Fuchs, et al., "Identification of Differentially Expressed Genes by Mutually Subtracted RNA Fingerprinting," Anal. Biochem., 286:91-98 (2000).

(56) References Cited

OTHER PUBLICATIONS

Gebeyehu, G., et al., "Novel biotinylated nucleotide-analogs for labeling and colorimetric detection of DNA," Nucl. Acids Res. 15:4513 (1987).
Geller, A.I. et al., "An HSV-1 Vector Expressing Tyrosine Hydroxylase Causes Production and Release of L-DOPA from Cultured Rat Striatal Cells," J. Neurochem 64:487-496 (1995).
Geller, A.I., et al., "Infection of cultured central nervous system neurons with a defective herpes simplex virus 1 vector results in stable expression of *Escherichia coli* β-galactosidase," PNAS USA 87:1149-1153 (1990).
Geller, A.I. et al., "Long-term increases in neurotransmitter release from neuronal cells expressing a constitutively active adenylate cyclase from a herpes simplex virus type 1 vector," PNAS U.S.A. :90:7603-7607 (1993).
Genbank Accession NM 000559.2. "Homo sapiens hemoglobin, gamma A (HBG1), mRNA." Jan. 26, 2014. 2 pages.
Giuliano, et al., "Determination of Intracellular pH of BALB/c-3T3 Cells Using the Fluorescence of Pyranine," Anal. Biochem 167:362-371 (1987).
Giuliano, et al., "FLuorescent Protein Biosensors: Measurement of Molecular Dynamics in Living Cells," Ann. Rev. of Biophysics and Biomolecular Structure 24:405-434 (1995).
Giuliano, et al., "Light-Optical-Based Reagents for the Measurement and Manipulation of Ions, Metabolites, and Macromolecules in Living Cells," Methods in Neuroscience 27:1-16 (1995).
Going & Gusterson, "Molecular Pathology and Future Developments," Eur. J. Cancer, 35:1895-1904 (1999).
Hagihara, et al., "Vinylogous Polypeptides: An Alternate Peptide Backbone," J. Amer. Chem. Soc. 114:6568-6571 (1992).
Haussecker and Proudfoot, "Dicer-Dependent turnover of intergenic transcripts from the human β-globin gene cluster." Molecular and Cellular Biology, 25:21, 9724-9733 (2005).
Heller, et al., "Discovery and analysis of inflammatory disease-related genes using cDNA microarrays," PNAS U.S.A. 94:2150-2155 (1997).
Herdewin P., "Heterocyclic Modifications of Oligonucleotides and Antisense Technology," Antisense & Nucleic Acid Drug Dev., 10:297-310 (2000).
Hirschmann, et al. Nonpeptidal Peptidomimetics with β-D-Glucose Scaffolding. A Partial Somatostatin Agonist Bearing a Close Structural Relationship to a Potent, Selective Substance P Antagonist. J. Amer. Chem. Soc., 114:9217-9218 (1992).
Hobbs-DeWitt, et al., "Diversomers: An approach to nonpeptide, nonoligomeric chemical diversity," Proc. Nat. Acad. Sci. USA 90;6909-6913 (1993).
Houghton AN, Gold JS, Blachere NE, Immunity against cancer: lessons learned from melanoma,. Curr Opin Immunol 13:134-140 (2001).
"Single gene variation linked to obesity: Variation in the BDNF gene may affect brain's regulation of appetite, study suggests. Science Daily, published Oct. 29, 2015, 7 pages. http://www.sciencedaily.com/releases/2015/10/151029141133.htm".
International Search Report and Written Opinion dated Jan. 31, 2011 for PCT/US10/024079.
International Human Genome Sequencing Consortium "Finishing the euchromatic sequence of the human genome." Nature 431:7011:931-945 (2004).
International Preliminary Report on Patentability dated Sep. 25, 2014 for PCT/US2013/030589.
International Search Report and Written Opinion dated Feb. 7, 2011 for PCT/US10/026119.
International Search Report and Written Opinion dated Nov. 5, 2010 for PCT/US10/0247403.
International Search Report and Written Opinion dated Nov. 5, 2010 for PCT/US10/027394.
International Search Report and Written Opinion dated Oct. 28, 2013 for PCT/US2013/030589.
International Search Report dated Sep. 29, 2008 for PCT/US2006/062672.

Janda, K.D. "Tagged versus untagged libraries: Methods for the generation and screening of combinatorial chemical libraries," PNAS 91:10779-10785 (1994).
Janowski, et al., "Inhibiting gene expression at transcription start sites in chromosomal DNA with antigene RNAs," Nature Chemical Biology, 1(4):216-222 (2005).
Japanese Patent Application No. 2015-500527 Office Action dated Dec. 19, 2016.
Jungblut, et al., "Proteomics in human disease: Cancer, heart and infectious diseases," Electrophoresis 20:2100-2110 (1999).
Jurecic & Belmont, "Long-distance DD-PCR and cDNA microarrays," Curr. Opin. Microbiol., 3:316-321 (2000).
Kabanov et al. A new class of antivirals: antisense oligonucleotides combined with a hydrophobic substituent effectively inhibit influenza virus reproduction and synthesis of virus-specific proteins in MDCK cells. FEBS Lett 259:327-330 (1990).
Kaplitt, M.G., et al., "Long-term gene expression and phenotypic correction using adeno-associated virus vectors in the mammalian brain," Nat. Genet. 8:148-154 (1994).
Kapranov, P. et al., "Examples of the complex architecture of the human transcriptome revealed by RACE and high-density tiling arrays," Genome Res 15:7:987-997 (2005).
Katayama, S. et al., "Antisense Transcription in the Mammalian Transcriptome," Science 309:1564-1566 (2005).
Kawahara & Nishikura, "Extensive adenosine-to-inosine editing detected in Alu repeats of antisense RNAs reveals scarcity of sense-antisense duplex formation," Febs Lett 580:2301-2305 (2006).
Kay, et al., "Identification of enzyme inhibitors from phage-displayed combinatorial peptide libraries," Comb Chem High Throughput Screen 4:535-543 (2001).
Kenan, et al., "Exploring molecular diversity with combinatorial shape libraries," Trends Biochem Sci 19:57-64 (1994).
Kocerha, et al., "microRNAs in CNS disorders," Neuromolecular Med. 11(3):162-72 (2009).
Kornberg, A., DNA Replication, W.H. Freeman & Co., San Francisco, (1992) pp. 75-77 (1980).
Kraynack, et al. Small interfering RNAs containing full 2'-O-methylribonucleotide-modified sense strands display Argonaute2/eIF2C2-dependent activity. RNA. 12(1):163-76 (2006).
Larson, et al., "Rapid DNA Fingerprinting of Pathogens by Flow Cytometry," Cytometry, 41:203-208 (2000).
Larsson, et al., "High-throughput protein expression of cDNA products as a tool in functional genomics," J. Biotechnology., 80:143-157 (2000).
Le Gal La Salle et al., "An Adenovirus Vector for Gene Transfer into Neurons and Glia in the Brain," Science 259:988-990 (1993).
Lebl, et al., "One-bead-one-structure combinatorial libraries," Biopolymers 37:177-198 (1995).
Letsinger et al. Cholesteryl-conjugated oligonucleotides: Synthesis, properties, and activity as inhibitors of replication of human immunodeficiency virus in cell culture. PNAS 86:6553-6556 (1989).
Li et al., "Control of APP processing and Aβ generation level by BACE1 enzymatic activity and transcription," Faseb J 20; 285-292 (2006).
Li, et al., Increased plaque burden in brains of APP mutant MnSOD heterozygous knockout mice. J. Neurochem 89 1308-1312 (2004).
Liang, et al., "Parallel Synthesis and Screening of a Solid Phase Carbohydrate Library," Science 274:1520-1522 (1996).
Luther, "Role of endogenous antisense RNA in cardiac gene regulation," J. Mol. Med. 83:26-32 (2005).
Madden, et al., "Serial analysis of gene expression: from gene discovery to target identification," Drug Discov. Today 5:415-425 (2000).
Magistri et al., "Regulation of chromatin structure by long noncoding RNAs: focus on natural antisense transcripts." Trends in Genetics, 28:8, 389-396, 2012.
Makalowska I, Lin CF, Makalowski W., "Overlapping genes in vertebrate genomes," Comput Biol. Chem 29:1:1-12 (2005).
Mannino and Gould-Fogerite, "Liposome Mediated Gene Transfer," BioTechniques 6:682-690 (1988).
Manoharan et al. Chemical Modifications to Improve Uptake and Bioavailability of Antisense Oligonucleotides. Ann. N.Y. Acad. Scie 660:306-309 (1992).

(56) References Cited

OTHER PUBLICATIONS

Manoharan et al. Cholic Acid-Oligonucleotide Conjugates for Antisense Applications. Bioorg. Med. Chem. Let 4:1053-1060 (1994).
Manoharan et al. Introduction of a Lipophilic Thioether in the Minor Groove of Nucleic Acids for Antisense Applications. Bioorg. Med. Chem. Let 3:2765-2770 (1993).
Manoharan et al. Lipidic Nucleic Acids. Tetrahedron Lett 36:3651-3654 (1995).
Manoharan et al. Oligonucleotide Conjugates: Alteration of the Pharmacokinetic Properties of Antisense Agents. Nucleosides & Nucleotides 14:969-973 (1995).
Manoharan, M., "2'-Carbohydrate modifications in antisense oligonucleotide therapy: importance of conformation, configurationj and conjugation," Biochemica et Biophysica Acta 1489:117-139 (1999).
Mattick, J. S. "RNA regulation: a new genetics?" Nat. Rev. Genet 5:4:316-323 (2004).
Maurer, R.A., "Cationic Liposome-Mediated Transfection of Primary Cultures of Rat Pituitary Cells," Bethesda Res. Lab. Focus 11:2:25 (1989).
Mcneil in Methods in Cell Biology vol. 29, Taylor and Wang (eds.) p. 153-173 (1989).
Modarresi et al., "Inhibition of natural antisense transcripts in vivo results in gene-specific transcriptional upregulation." Nature Biotechnology. 30:5, p. 453-459, 2012.
Modarresi et al., "Knockdown of BACE1-AS Nonprotein-Coding Transcript Modulates Beta-Amyloid Related Hippocampal Neurogenesis," International Journ. of Alzeheimers, vol. 2011, Article ID 929042, 11 pgs.
Morelli et al., "The antisense bcl-2-IgH transcript is an optimal target for synthetic oligonucleotides," PNAS USA 94:8150-8155 (1997).
Mou et al., Human obesity associated with an intronic SNP in the brain-derived neurotropic factor locus. Cell Reports, 13:1-8 (2015).
Nielsen, et al., "Sequence-Selective Recognition of DNA by Strand Displacement with a Thymine-Substituted Polyamide," Science 254:1497-1500 (1991).
NIH Researchers link single gene variation to obesity. News Release published Oct. 29, 2015, 3 pages.
Oberhauser et al. Effective incorporation of 2'-O-methyl-oligoribonucleotides into liposomes and enhanced cell association through modification with thiocholesterol. Nucl. Acids Res. 20:533-538 (1992).
Orgel, Selection in vitro. Proc. R. Soc. London, B 205, 435-442 (1979).
Petit, et al., "Wild-type PINK1 prevents basal and induced neuronal apoptsis, a protective effect abrogated by Parkinson disease-related mutations," Journ. Biol. Chem. vol. 280, No. 40, pp. 34025-34032 (2005).
Prasanth, et al., "Regulating Gene Expression through RNA Nuclear Retention," Cell 123, 249-263 (2005).
Prashar & Weissman, "READS: A Method for Display of 3'-End Fragments of Restriction Enzyme-Digested cDNAs for Analysis of Differential Gene Expression," Methods Enzymol., 303:258-272 (1999).
Pruunsild et al., "Dissecting the human BDNF locus: Bidirectional transcription, complex splicing, and multiple promotors." Genomics, Academic Press, San Diego, CA, 90:3, 397-406 (2007).
Quantin et al. Adenovirus as an expression vector in muscle cells in vivo. PNAS USA 89(7):2581-2584 (1992).
"Robb et al., Post-transcriptional regulation of endothelial nitric-oxide synthase by an overlapping antisense mRNA transcript. The Journal of Biological Chemistry, 279(36): 37982-37996 (2004)".
Robb, et al. Post-transcriptional regulation of endothelial nitric-oxide synthase by an overlapping antisense mRNA transcript. J Biol Chem. 279(36):37982-96 (2004).
Rosenfeld, et al., "In Vivo Transfer of the Human Cystic Fibrosis Transmembrane Conductance Regulator Gene to the Airway Epithelium," Cell, 68:143-155 (1992).
Rosok and Sioud, "Systematic identification of sense-antisense transcripts in mammalian cells," Nature Biotech. 22(1):104-108 (2004).
Russian Patent Application No. 2014140112 Office Action dated Oct. 24, 2016.
Saison-Behmoaras et al. Short modified antisense oligonucleotides directed against Ha-ras point mutation induce selective cleavage of the mRNA and inhibit T24 cells proliferation. EMBO J. 10:1111-1118 (1991).
Sanghvi, Y.S., in Crooke, S.T. and Lebleu, B., eds., Antisense Research and Applications, CRC Press, Boca Raton, p. 276-278 (1993).
Scheele, et al., "The human PINK1 locus is regulated in vivo by a non-coding natural antisense Rna during modulation of mitochondrial function," BMC Genomics, vol. 8, No. 1, p. 74 (2007).
Schena, et al., "Parallel human genome analysis: Microarray-based expression monitoring of 1000 genes," PNAS 93:10614-10619 (1996).
Shea et al. Synthesis, hybridization properties and antiviral activity of lipid-oligodeoxynucleotide conjugates. Nucl. Acids Res 18:3777-3783 (1990).
Shen et al., "Modification of globin gene expression by RNA targeting strategies." Experimental Hematology, vol. 35, 1209-1218 (2007).
Shimomura, et al., "Semi-synthetic aequorin," J. of Biochemistry (Tokyo) 251:405-410 (1988).
Singer, et al., "Targeting BACE1 with siRNAs ameliorates Alzheimer disease neuropathology in a transgenic model," Nat Neurosci 8:1343-1349 (2005).
Smith and Waterman, Comparison of Biosequences. Adv. Appl. Math., 2:482-489 (1981).
Southwick, et al., "Cyanine Dye Labeling Reagents-Carboxymethylindocyanine Succinimidyl Esters," Cytometry 11:418-430 (1990).
Stratford-Perricadet, et al., "Widespread Long-term Gene Transfer to Mouse Skeletal Muscles and Heart," J. Clin. Invest., 90:626-630 (1992).
Sullenger, et al., "Overexpression of TAR sequences Renders Cells Resistant to Human Immunodeficiency Virus Replication," Cell63:601-608 (1990).
Sun et al., "Downregulation of Sirt1 by antisense oligonucleotides induces apoptosis and enhances radiation sensitization in A549 lung cancer cells." Lung Cancer 58(1):21-29 (2007).
Sutcliffe, et al., "TOGA: An automated parsing technology for analyzing expression of nearly all genes," PNAS, 97:1976-1981 (2000).
Sutton, et al., "TIGR Assembler: A New Tool for Assembling Large Shotgun Sequencing Projects," Genome Science & Tech., 1:9-19 (1995).
Svinarchuk et al. Inhibition of HIV proliferation in MT-4 cells by antisense oligonucleotide conjugated to lipophilic groups. Biochimie 75:49-54 (1993).
Tamagno, et al., "The various aggregation states of β-amyloid 1-42 mediate different effects on oxidative stress, neurodegeneration, and BACE-1 expression," Free Radic Biot Med 41:202-212 (2006).
Thakker, D.R., et al., "siRNA-mediated knockdown of the serotonin transporter in the adult mouse brain," Mol Psychiatry 10:782-789 (2005).
Thakker, et al., "Neurochemical and behavioral consequences of widespread gene knockdown in the adult mouse brain by using nonviral RNA interference," PNAS 101:17270-17275 (2004).
Thomas et al., "Intracellular pH Measurements in Ehrlich Ascites Tumor Cells Utilizing Spectroscopic Probes Generated in Situ," Biochemistry 18:2210-2218 (1979).
Thompson, et al., "Synthesis and Applications of Small Molecule Libraries" Chem Rev 96:555-600 (1996).
To, Ky, "Identification of Differential Gene Expressionm by High Throughput Analysis," Comb. Chem. High Throughput Screen 3:235-241 (2000).
Tong, et al., "Oxidative stress potentiates BACE1 gene expression," Neural Transm 112, 455-469 (2005).
Toulme, J.J., "New candidates for true antisense," Nature Biotechnology 19:17-18 (2001).

(56) References Cited

OTHER PUBLICATIONS

Tsien in Methods in Cell Biology vol. 30 Taylor and Wang (eds) p. 127-156 (1989).
Uhlenbeck, O. C., A small catalytic oligoribonucleotide. Nature, 328: 596-600 (1987).
Ulhman, E., "Recent advances in the medical chemistry of antisense oligonucleotide," Current Opinions in Drug Discovery & Development 3:203-213 (2000).
U.S. Appl. No. 14/384,659 Office Action dated Jan. 8, 2016.
U.S. Appl. No. 12/159,607 Office Action dated Aug. 25, 2010.
U.S. Appl. No. 12/159,607 Office Action dated Jan. 27, 2012.
U.S. Appl. No. 12/159,607 Office Action dated Jan. 7, 2010.
U.S. Appl. No. 12/159,607 Office Action dated Jun. 13, 2011.
U.S. Appl. No. 13/563,581 Office Action dated Jul. 27, 2015.
U.S. Appl. No. 13/563,581 Office Action dated Mar. 24, 2016.
U.S. Appl. No. 14/384,659 Office Action dated Jul. 7, 2016.
U.S. Appl. No. 14/723,740 Office Action dated Jan. 17, 2017.
Van Den Eynde BJ, "T cell defined tumor antigens," Curr Opin Immunol 9:684-693 (1997).
Van Der Bruggen, et al., "Tumor-specific shared antigenic peptides recognized by human T cells," Immunol Rev188:51-64 (2002).
Vanhee-Brossolet and Vaquero, "Do natural antisense transcripts make sense in eukaryotes?" Gene 211:1-9 (1998).
Varela et al., Natural antisense makes sense for gene-specific activation in brain. Molecular Therapy-Nucleic Acids, 1:e24, 4 pages, 2012.
Vassar, Beta-Secretase (BACE) as a drug target for alzheimer's disease. Advanced Drug Delivery Reviews, 54:1589-1602 (2002).
Vaughn, et al., "Human Antibodies with Sub-nanomolar Affinities Isolated from a Large Non-immunized Phage Display Library," Nature Biotechnology, 14:3:309-314 (1996).
Velculescu, et al., "Serial Analysis of Gene Expression," Science 270:484-487 (1995).
Wahlestedt, C., "Antisense oligonucleotide strategies in neuropharmacology," Trends Pharmacol Sci 15:2:42-46 (1994).
Wahlestedt, "Natural antisense and noncoding RNA transcripts as potential drug targets," Drug Discovery Today 11 (11/12):503-508 (2006).
Walsh, et al., The role of cell-derived oligomers of Aβ in Alzheimer's disease and avenues for therapeutic intervention, Biochem Soc Trans 33: 1087-1090 (2005).
Wang, B.B. et al., "Identification of a nuclear-specific cyclophilin which interacts with the proteinase inhibitor eglin c," Biochem J. 314 (Pt 1) 313-319 (1996).
Wiesenhofer et al., "Glial cell line-derived neurotrophic factor (GDNP) is a proliferation factor for rat C6 glioma cells: evidence from antisense experiments," Antisense & Nucleic Acid Drug Development 10(5):311-321 (2000).
Xue, et al., "Hypoxia and reoxygenation increased BACE1 mRNA and protein levels in human neuroblastoma SH-SY5Y cells," Neurosci Lett 405,231-235 (2006).
Yamada, et al., "Endothelial Nitric-oxide Synthase Antisense (NOS3AS) Gene Encodes an Autophagy-related Protein (APG9-like2) Highly Expressed in Trophoblast," Journ. Biol. Chem. vol. 280, No. 18 pp. 18283-18290 (2005).
Yang, et al., "Cellular and Humoral Immune Responses to Viral Antigens Create Barriers to Lung-Directed Gene Therapy with Recombinant Adenoviruses," J. Virol 69:2004-2015 (1995).
Japanese Patent Application No. 2015-500527 Decision of Rejection dated Oct. 4, 2017.
Tanila, H. The role of BDNF in Alzheimer's Disease. Neurobiology of Disease, 97:114-118, 2017.
U.S. Appl. No. 15/398,630 dated Oct. 19, 2017.
Canadian Patent Application No. 2,867,262 Office Action dated Jan. 10, 2019.
Chen H: Exploiting the intron-splicing mechanism of insect cells to produce viral vectors harboring toxic genes for suicide gene therapy; Molecular Therapy—Nucleic Acids 1:e57 (2012).
Japanese Patent Application No. 2018-016012 First Office Action dated Jan. 15, 2019.

\* cited by examiner

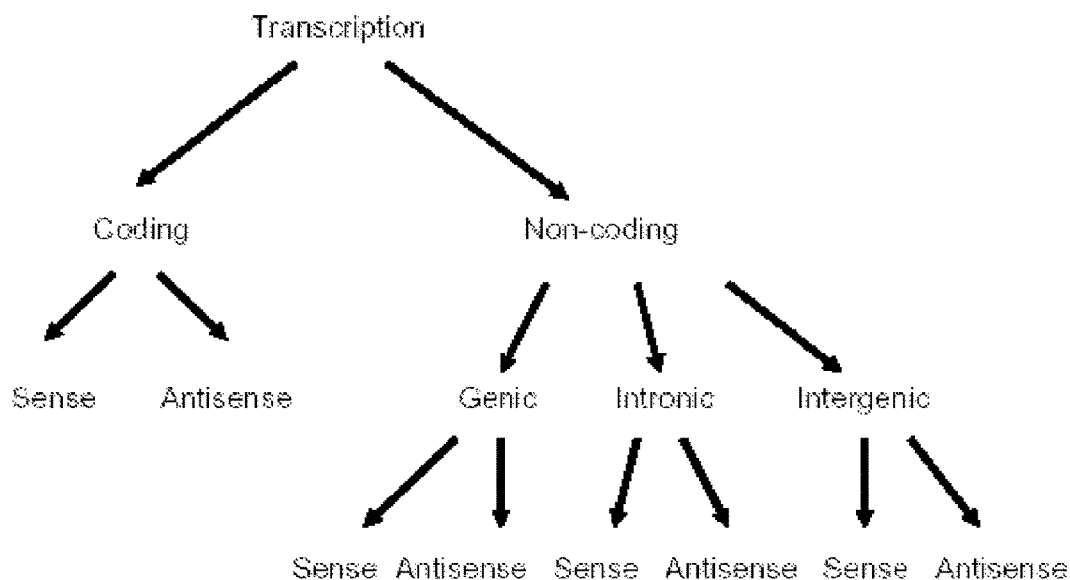
FIGURE 1A
(1) Head-to-head (convergent):
(2) Tail-to-tail (divergent):
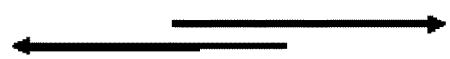
(3) Fully overlapping:
FIGURE 1B

Discordant regulation:
 Antisense transcript ↓ ⟹ ↑ Sense transcript

FIGURE 2A

Concordant regulation:
 Sense transcript ↓
 Antisense transcript ↓ } ↓↓ Sense transcript

FIGURE 2B

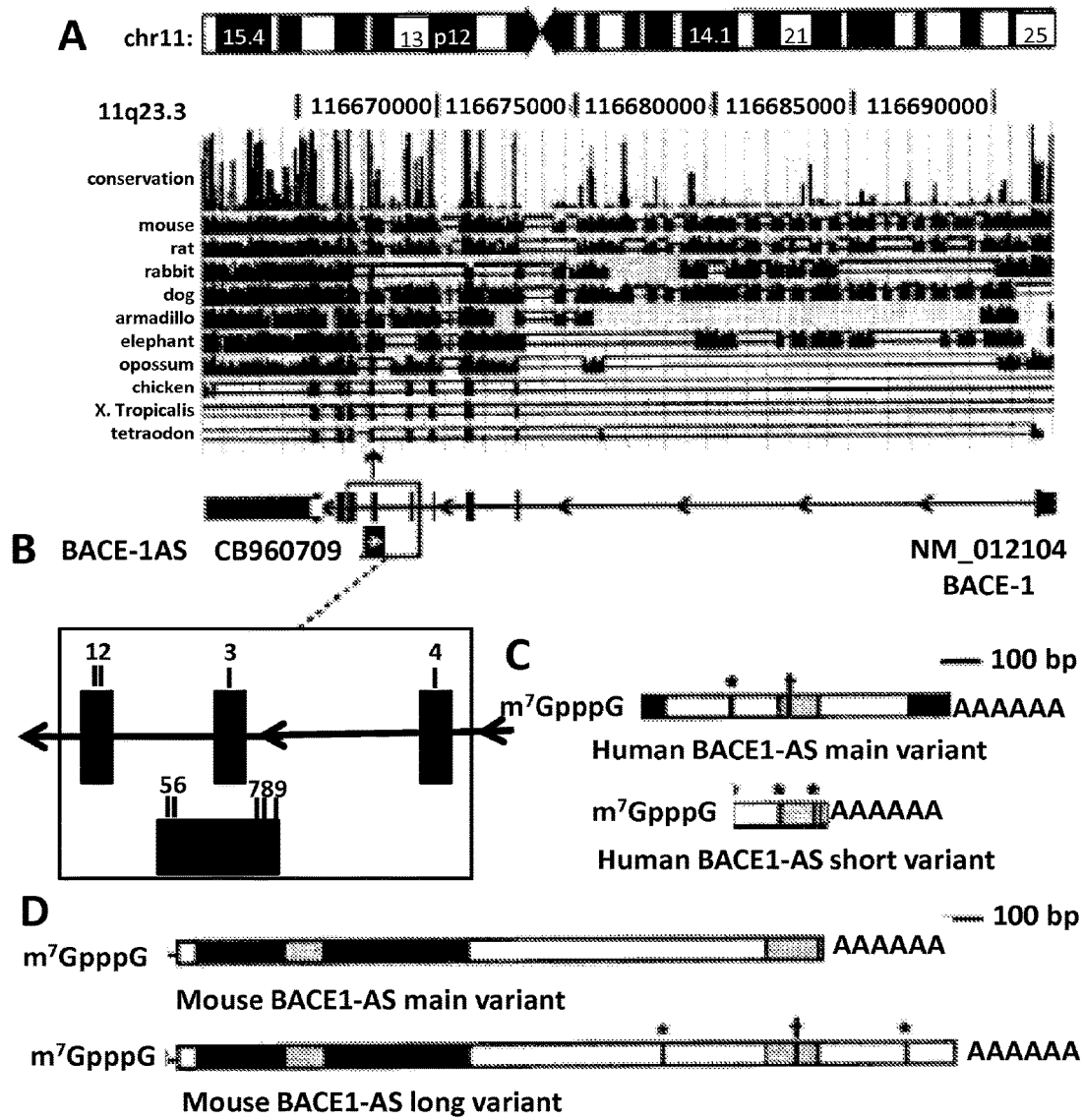
FIGURES 12A-D

NATURAL ANTISENSE AND NON-CODING RNA TRANSCRIPTS AS DRUG TARGETS

CROSS-REFERENCE TO RELATED APPLICATIONS

This application is a divisional of U.S. application Ser. No. 13/563,581, filed Jul. 31, 2012, which is a continuation of U.S. application Ser. No. 12/159,607, filed Dec. 3, 2008, which is a 371 U.S. National Phase Application of PCT/US2006/062672, filed Dec. 28, 2006, which claims the benefit of U.S. Application No. 60/754,463, filed Dec. 28, 2005; all of which are incorporated herein by reference in their entirety.

FIELD OF THE INVENTION

The invention provides compositions and methods for highly selective targeting of heterologous nucleic acid sequences. The oligonucleotides are siRNA's which bind in a sequence dependent manner to their target genes and regulate expression of undesired nucleic acid sequences in a target cell. Moreover, siRNA's can specifically and selectively kill either bacterial or human cells if the target is present in their genomes.

BACKGROUND

The past few years have seen a significant increase in our understanding of the complexity of mammalian transcription and many novel ribonucleic acid (RNA) transcripts have been detected. This has partly come as a surprise since the total number of conventional (protein coding) genes in the human genome (around 20,000-25,000) is much lower than anticipated a few years ago, and of the same magnitude as the number of genes in simpler organisms such as *Drosophila melanogaster* or *Caenorhabditis elegans* (Finishing the euchromatic sequence of the human genome. *Nature* 431 (7011):931-945 (2004)).

Two major transcriptomics efforts have in a complementary manner led the way in establishing an emerging modified view of mammalian transcription. First, the international FANTOM (Functional Annotation of the Transcriptome of Mammals) has for several years produced and analyzed massive amounts of complementary DNA (cDNA) sequencing data primarily from mouse but also from human cells and tissues (Carninci, P. et al. (2005) *Science* 309 (5740), 1559-1563; Katayama, S. et al. (2005) *Science* 309 (5740), 1564-1566). Second, independently, high density ("tiling") microarray experiments have provided complementary evidence that transcription occurs extensively throughout the human genome and that there exist many unannotated transcripts of unknown function (Cheng, J. et al. (2005). *Science* 308 (5725), 1149-1154; Kapranov, P. et al. (2005) *Genome Res* 15 (7), 987-997).

RNAs can be classified into (1) messenger RNAs (mRNAs), which are translated into proteins, and (2) non-protein-coding RNAs (ncRNAs). Until recently, it was thought that there are only small numbers of ncRNAs (e.g., tRNAs, rRNAs and spliceosomal RNAs) which all would relate to protein synthesis or function. Moreover, until a few years ago there were no systematic efforts to identify novel ncRNA transcripts and elucidate their functions.

SUMMARY

Sequence specific siRNA bind to a target nucleic acid molecule, and regulating expression of a gene expression product. Methods are provided wherein up-regulation or inhibition of targeted nucleic acids are effective in the treatment of abnormal cell growth, neurological disorders, aberrant cell regulation, diseases and the like. Drug discovery strategies are encompassed within the invention.

In a preferred embodiment, a method of up-regulating gene expression comprises targeting a nucleic acid molecule to an anti-sense transcript of a sense strand, wherein the nucleic acid molecule targeting the anti-sense transcript is complementary to the anti-sense strand; and, binding of the nucleic acid to the anti-sense transcript, thereby, elevating expression of the sense strand; and up-regulating expression of the gene. Preferably, binding of the nucleic acid molecule to the anti-sense strand is effective under high, medium or low stringency conditions. Any disease, abnormality (congenital or otherwise) tumor, disease caused by pathogens (e.g. prions, viruses such as tumor causing viruses) and the like; molecular targets, e.g. both intra- and extra-cellular molecules (e.g. receptor, enzyme, cytokine transcripts), can be treated by designing molecules that target desired sense and/or antisense loci. The sequence specific RNA molecules can be designed so that they target overlapping sequences and also target the complementary strands.

In another preferred embodiment, the nucleic acid molecule is an RNA molecule and comprises at least one of SEQ ID NOs: 1-67.

In another preferred embodiment, a method of inhibiting gene expression comprises targeting a nucleic acid molecule to an anti-sense transcript and sense strand transcript, wherein the nucleic acid molecule targeting the anti-sense transcript is complementary to the anti-sense strand and the nucleic acid molecule targeting the sense transcript is complementary to the sense strand; and, binding of the nucleic acid to the anti-sense and sense transcript, thereby, inhibiting gene expression. Preferably, the nucleic acid molecule is an RNA molecule and the nucleic acid molecules targeting the anti-sense and sense transcripts bind said transcripts in convergent, divergent orientations with respect to each other and/or are overlapping.

In another preferred embodiment, the nucleic acid molecule is at least one of SEQ ID NO's: 4-8 and the targeted nucleic acid is coding or non-coding transcript.

In preferred embodiments the targeted genes comprise: CD97, TS-α, C/EBP delta, CDC23, PINK1, HIF1α, Gnbp3g, Adrenomedullin AM1 receptor, 6330439J10 (3-oxoacid CoA transferase), CtpW85 (Cathepsin W), Ddx-39, rTS-α, I530027A02, Kif20a, PINK-AS, aHIF1α, Gnbp3g-AS, AdmR-AS, A230019L24, or CtpW-AS. Preferably, the targeted nucleic acid comprises nucleic acid sequences PINK-AS, aHIF1α, Gnbp3g-AS, AdmR-AS, A230019L24, or CtpW-AS. Both coding and non-coding sequences, transcripts can be targeted, and/or overlapping sequences on both the 5'-3' and the complementary 3'-5' sequences.

In preferred embodiments, the targeted non-coding nucleic acid comprises nucleic acid sequences CD97, TS-α, C/EBP delta, CDC23, PINK1, HIF1α, Gnbp3g, Adrenomedullin AM1 receptor, 6330439J10 (3-oxoacid CoA transferase), CtpW85 (Cathepsin W), Ddx-39, rTS-α, I530027A02, or Kif20a.

In another preferred embodiment a pharmaceutical composition comprises at least one of SEQ ID NO's: 1-67 and variants thereof.

In yet another preferred embodiment, an isolated nucleic acid comprises any one of SEQ ID NO's: 1-67 and variants thereof.

In another preferred embodiment, a composition comprises nucleic acid sequences targeting at least one gene and/or transcript comprising CD97, TS-α, C/EBP delta, CDC23, PINK1, HIF1α, Gnbp3g, Adrenomedullin AM1 receptor, 6330439J10 (3-oxoacid CoA transferase), CtpW85 (Cathepsin W), Ddx-39, rTS-α, I530027A02, Kif20a, PINK-AS, aHIF1α, Gnbp3g-AS, AdmR-AS, A230019L24, or CtpW-AS. The targeted loci can be overlapping sequences and/or targeting both the sense strand and the antisense strand. In other aspects, both the coding and non-coding sequences are targeted.

In a preferred embodiment, a method of treating Parkinson's Disease comprises administering to a patient in need thereof at least one of SEQ ID NO: 1-3.

In another preferred embodiment a pharmaceutical composition comprises at least one nucleic acid molecule and variants thereof of SEQ ID NOS: 1-67 in a pharmaceutically acceptable carrier.

In another preferred embodiment, the nucleic acid molecules comprise siRNA molecules targeting overlapping regions of a sense/antisense locus. For example, a pharmaceutical composition for treating Alzheimer's disease target BACE transcripts. The nucleic acid molecules can be designed to target overlapping sequences or loci of BACE transcripts. These molecules specific for overlapping targets in Alzheimer's disease treatment comprise SEQ ID NOS: 41-43 and SEQ ID NOS: 44-45 and variants thereof.

In another preferred embodiment, an expression vector comprises any one or more of SEQ ID NOS: 1-67 and variants thereof.

In another preferred embodiment, an isolated peptide is encoded by any one or more of SEQ ID NOS: 1-67 and variants thereof.

In another preferred embodiment, an isolated antibody is specific for BACE-1 mRNA, BACE-1-AS RNA, SEQ ID NOS: 1-67 and peptides thereof.

In another preferred embodiment, a method of treating neurological disorders comprises administering to a patient in need thereof at least one of SEQ ID NO's: 4-8; 40-61 and 64-67 and variants thereof. The method further embodies administering SEQ ID NOS: 4-8; 40-61, 64-67 in combinations targeting overlapping regions of a sense/antisense locus.

In another preferred embodiment, varying combinations of at least two of SEQ ID NOS: 4-8, 40-61, 64-67 and variants thereof are administered to a patient over a course of treatment. Examples of neurological disorders include, but not limited to Alzheimer's Disease, Aphasia, Bell's Palsy, Creutzfeldt-Jakob Disease, Epilepsy, Encephalitis, Huntington's Disease, Neuromuscular Disorders Neuro-oncology, Neuro-immunology, Neuro-otology, Pain, Phobia, Sleep Disorders, Tourette's Syndrome, Parkinson's Disease and other movement disorders.

In another preferred embodiment, a method of up-regulating gene expression comprises targeting a nucleic acid molecule to an anti-sense transcript of a sense strand, wherein the nucleic acid molecule targeting the anti-sense transcript is complementary to the anti-sense strand; and, binding of the nucleic acid to the anti-sense transcript; wherein, expression of the sense strand is elevated and expression of the gene is up-regulated. Preferably, the nucleic acid molecule is an interference RNA molecule.

In a preferred embodiment, the nucleic acid molecule is at least one of SEQ ID NOs: 1-3; 4-32, 40-61, 64-67 and variants thereof. In one aspect, SEQ ID NO's: 1-3; 4-32, 40-61, 64-67 nucleic acid molecules and variants thereof, comprise at least one modified nucleobase.

In another preferred embodiment, a method of inhibiting gene expression comprises targeting a nucleic acid molecule to an anti-sense transcript and sense strand transcript, wherein the nucleic acid molecule targeting the anti-sense transcript is complementary to the anti-sense strand and the nucleic acid molecule targeting the sense transcript is complementary to the sense strand; and, binding of the nucleic acid to the anti-sense and sense transcript; wherein, gene expression is inhibited.

In a preferred embodiment, the nucleic acid molecules targeting the anti-sense and sense transcripts bind said transcripts convergent, divergent orientations with respect to each other or are overlapping. Preferably, the targeted nucleic acid is coding and/or non-coding transcript. Examples of targeted genes comprise: CD97, TS-α, C/EBP delta, CDC23, PINK1, HIF1α, Gnbp3g, Adrenomedullin AM1 receptor, 6330439J10 (3-oxoacid CoA transferase), CtpW85 (Cathepsin W), Ddx-39, rTS-α, I530027A02, Kif20a, PINK-AS, aHIF1α, Gnbp3g-AS, AdmR-AS, A230019L24, BACE or CtpW-AS. Examples of targeted coding nucleic acid comprise nucleic acid sequences PINK-AS, aHIF1α, Gnbp3g-AS, AdmR-AS, A230019L24, or CtpW-AS. Examples of targeted non-coding nucleic acid comprise nucleic acid sequences CD97, TS-α, C/EBP delta, CDC23, PINK1, HIF1α, Gnbp3g, Adrenomedullin AM1 receptor, 6330439J10 (3-oxoacid CoA transferase), CtpW85 (Cathepsin W), Ddx-39, rTS-α, I530027A02, or Kif20a.

In another preferred embodiment, treating age related macular degeneration comprises administering to a patient at least one of SEQ ID NO's: 1-67 and variants thereof.

In another preferred embodiment, a composition comprises nucleic acid sequences targeting overlapping sequences, coding- and non-coding of any one of CD97, TS-α, C/EBP delta, CDC23, PINK1, HIF1α, Gnbp3g, Adrenomedullin AM1 receptor, 6330439J10 (3-oxoacid CoA transferase), CtpW85 (Cathepsin W), Ddx-39, rTS-α, I530027A02, Kif20a, PINK-AS, aHIF1α, Gnbp3g-AS, AdmR-AS, A230019L24, BACE or CtpW-AS.

Other aspects of the invention are described infra.

BRIEF DESCRIPTION OF THE DRAWINGS

The invention is pointed out with particularity in the appended claims. The above and further advantages of this invention may be better understood by referring to the following description taken in conjunction with the accompanying drawings, in which:

FIGS. 1A and 1B is a schematic representation showing antisense transcription basics. FIG. 1A shows how antisense transcripts can be generated within the mammalian transcriptome. FIG. 1B shows that there are three possibilities with respect to overlap of antisense transcript with sense transcript.

FIGS. 2A-2B are a schematic representation showing two possibilities to alter sense transcript levels by invoking antisense knockdown (e.g., by use of siRNA). FIG. 2A represents the case where regulation is dicordant while FIG. 2B illustrates concomitant knockdown of both sense and the corresponding antisense transcript.

FIGS. 12A-12D re schematic representations showing the genomic organization of the human BACE-1 locus on human chromosome 11q 23.3 locus showing (FIG. 12A) genomic location of the BACE-1 mRNA and BACE-1-AS and strong conservation patterns of both transcript to several other species including mouse. BACE-1 transcribed from the negative strand of chromosome 11 and BACE-1-AS is transcribed from positive strand of chromosome 11 and it covers Exon-6 of the BACE-1. FIG. 12B shows the direction of transcription and overlap region between BACE-1 and BACE-1-AS in a larger view. Sites numbered 1, 2, and 4 are the BACE-1 siRNA target site and site 3 is the Northern blot probe site witch is in the overlap region and can detect both transcripts. Sites 2 and 5 also represent the FISH probe site for the sense and antisense respectively. Sites 6, 7 and 8 are the target site of the BACE-1-AS siRNA which are all in nonoverlapping part of the AS transcript. Sites 5 and 9 represent the primer site for 3' and 5' RACE respectively. FIGS. 12C and 12D depict RACE sequencing data of the BACE-1-AS from human and mouse brain respectively (16 clones each). Sequencing data revealed that antisense transcript contains cap structure and poly-A tail and undergoes differential splicing in both human and mouse. The yellow highlighted parts are overlap region to the BACE-1 sense transcript and green highlighted regions are new from our sequencing data, they did not exist in genome databases before. Point mismatches to the genomic sequence are indicated by stars (*) for A to G and crosses (†) for C to T changes.

FIG. 13A shows BACE-1 mRNA reduced by transfection with BACE-1 (S-a) siRNA, without significant change in BACE-1-AS level. Targeting BACE-1-AS transcripts, with three different siRNA, (AS-a, AS-b and AS-c) caused significant down regulation ($P<0.0001$) of both BACE-1 and BACE-1-AS transcript. 20 nM of siRNAs targeting non-overlapping part of transcripts were transfected in neuroblastoma cells (SH-SY5Y). All samples were normalized to 18s rRNA and graphed as the percent of each mRNA to the control negative siRNA sample. FIG. 13B shows ELISA detection of amyloid Aβ1-42 protein. Supernatant of the HEK-SW cells, after transfection with 20 nM of siRNA for BACE-1 (S-a), BACE-1-AS (AS-a), or both, were analyzed for amyloid Aβ1-42 protein. Results were plotted to the control siRNA transfected cells. Aβ1-42 protein was significantly downregulated ($P<0.0001$) with siRNA targeting BACE-1 or BACE-1-AS. Combination of both siRNA (10 nM of each) caused more significant downregulation ($P<0.001$).

FIG. 14A: dorso-medial prefrontal cortex (PFC), FIG. 14B: ventral hippocampus, FIG. 14C: dorsal hippocampus, FIG. 14D: dorsal striatum and FIG. 14E: cerebellum. The siRNAs directed against either BACE-1 or BACE-1-AS transcript resulted in a concomitant decrease in both BACE-1 and BACE-1-AS levels compared with control-treated groups (***=$P<0.0001$). Both transcripts in cerebellum (e) were unchanged ($P=0.1518$), as expected for a tissue which is not directly connected to the third ventricle of the brain.

FIG. 15A is a scan of photographs showing nuclear vs. cytoplasmic distribution of BACE-1 and BACE-1-AS RNA; In RNA-FISH images from SH-SY5Y, neuroblastoma cells upper panels left to right show DAPI nuclear stain, BACE-1 mRNA signals (Alexa Flour 594) covering whole cell, and overlay of both. Lower panels left to right, show DAPI nuclear stain, BACE-1-AS signals (Alexa flour 488), which is detectable mainly inside the nucleus and overlay of both. RT-PCR data revealed that, BACE-1-AS transcript is about 30 times more abundant in the nucleus than cytoplasm of the SH-SY5Y cells, while β-Actin and BACE-1 mRNA (sense) are nearly equal in both compartments. FIG. 15B are scans of photographs showing the observed nuclear retention pattern of BACE-1-AS substantially disappears upon exposure of the SH-SY5Y cells to a hyperosmotic shock with 30 nM of KCl for 5 minutes. When the cells were washed with PBS and returned back to regular media for one hour, the nuclear retention were restored again. Images show translocation of BACE-1-AS signals from nucleus to cytoplasm of SH-SY5Y cells upon exposure to KCl for 5 min, from left to right are DAPI nuclear stain, BACE-1-AS signals detectable from entire cells and overlay of both.

FIG. 15C are scans of photographs showing synthetic Aβ 1-42 peptides utilized as a different stressor for monitoring changes in nuclear retention of the BACE-1-AS. The SH-SY5Y cells were exposed to 1 µM of Aβ 1-42 for 2 hours and BACE-1-AS were shown to leave the nucleus. The relocation was recovered upon washing of the peptides and maintaining the cells on regular media for one hour. In set panels depicting relocation of the BACE-1-AS signals upon the same exposure, from left to right are DAPI nuclear stain, BACE-1-AS and overlay of both. In FIG. 15D, 7PA2-CHO cells were previously shown to overproduce Aβ 1-42 dimers and oligomers. The conditioned media of these cells and control parental CHO cells were collected and substituted with the regular media of the SH-SY5Y cells for two hours. Importantly, only conditioned media of 7PA2-CHO cells were able to relocate BACE-1-AS transcript from nucleus to cytoplasm. In set panels show the same relocation of BACE-1-AS upon incubation with 7PA2 condition media. From left to right, are DAPI nuclear stain, BACE-1-AS and overlay of both signals. FIG. 15E are graphs showing human Aβ 1-42 peptide is significantly elevated in brain of APP-tg mice comparing to wildtype as it appear from HTRF assay. FIG. 15F is a graph showing elevated level of Aβ 1-42, similar to in vitro experiments caused elevation of BACE-1-AS by 50% (P<0.0001) followed by concordant elevation of BACE-1. The increased level of BACE-1-AS was more than BACE-1 (P<0.001).

FIGS. 16A-16E are graphs showing cyclophilin-60 involvement in BACE-1-AS localization/regulation and stability of BACE-1 and BACE-1-AS transcripts. Effective knock-down of Cyp-60 in HEK-293T cells causes (FIG. 16A) significant downregulation (P<0.001) of BACE-1 and BACE-1-AS. FIG. 16B: After treatment of HEK293T cells with Cyp-60 siRNA, downregulation of the BACE-1-AS occurs in earlier time point, starting at 6 h post-transfection. FIG. 16C: Cyp-60 siRNA treatment also significantly reduced (P<0.0001) nuclear retention of BACE-1-AS. FIG. 16D: Stability of BACE-1 and BACE-1-AS transcripts over time are measured by real-time PCR in HEK-293T cells after stopping new RNA synthesis with α-amanitin. BACE-1-AS had a shorter half life than BACE-1 and β-Actin. 18srRNA which is a product of RNA polymerase III is unchanged and utilized as an endogenous control. FIG. 16E: Incubation of SH-SY5Y cells with condition media of the 7PA2 cells, which causes translocation of BACE-1-AS into cytoplasm, had a significant increase (P<0.001) in BACE-1 stability.

DETAILED DESCRIPTION

Figure 3A:
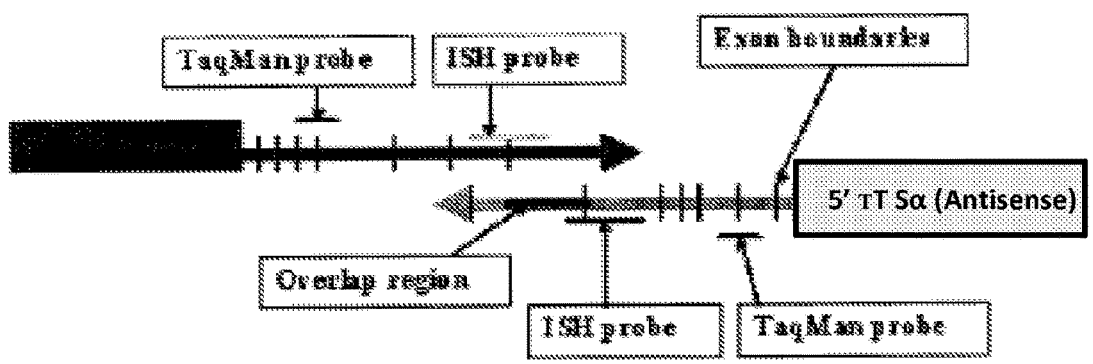
FIG. 3A is a schematic presentation of Thymidylate Synthase (TS-sense) and rTSα antisense mRNA. Exon boundaries are marked by transverse bars. The location of probes used for both TaqMan and in situ hybridization probes as well as the 3' overlap region of both S-AS mRNA are also indicated.

Small interfering RNA (siRNA) knock down antisense transcripts, and regulate the expression of their sense partners. This regulation can either be discordant (antisense knockdown results in sense transcript elevation) or concordant (antisense knockdown results in concomitant sense transcript reduction). New pharmacological strategies based on the knockdown of antisense RNA transcripts by siRNA (or another RNA targeting principle) are provided. In the case of discordant regulation, knockdown of antisense transcript elevates the expression of the conventional (sense) gene thereby conceivably mimicking agonist/activator action. In the case of concordant regulation, concomitant knockdown of antisense as well as sense transcripts results in synergistic reduction of the conventional (sense) gene expression.

Definitions

Unless defined otherwise, all technical and scientific terms herein have the same meaning as commonly understood by one of ordinary skill in the art to which this invention belongs. Although any methods and materials, similar or equivalent to those described herein, can be used in the practice or testing of the present invention, the preferred methods and materials are described herein.

As used herein, the singular forms "a," "an," and "the" include plural referents unless the context clearly dictates otherwise.

As used herein, the term "oligonucleotide specific for" refers to an oligonucleotide having a sequence (i) capable of forming a stable complex with a portion of the targeted gene, or (ii) capable of forming a stable duplex with a portion of a mRNA transcript of the targeted gene.

As used herein, the terms "oligonucleotide," "siRNA," "siRNA oligonucleotide," and "siRNA's" are used interchangeably throughout the specification and include linear or circular oligomers of natural and/or modified monomers or linkages, including deoxyribonucleosides, ribonucleosides, substituted and alpha-anomeric forms thereof, peptide nucleic acids (PNA), ed nucleic acids (LNA), phosphorothioate, methylphosphonate, and the like. Oligonucleotides are capable of specifically binding to a target polynucleotide by way of a regular pattern of monomer-to-monomer interactions, such as Watson-Crick type of base pairing, Hoogsteen or reverse Hoogsteen types of base pairing, or the like.

The oligonucleotide may be "chimeric," that is, composed of different regions. In the context of this invention "chimeric" compounds are oligonucleotides, which contain two or more chemical regions, for example, DNA region(s), RNA region(s), PNA region(s) etc. Each chemical region is made up of at least one monomer unit, i.e., a nucleotide in the case of an oligonucleotide compound. These oligonucleotides typically comprise at least one region wherein the oligonucleotide is modified in order to exhibit one or more desired properties. The desired properties of the oligonucleotide include, but are not limited, for example, to increased resistance to nuclease degradation, increased cellular uptake, and/or increased binding affinity for the target nucleic acid. Different regions of the oligonucleotide may therefore have different properties. The chimeric oligonucleotides of the present invention can be formed as mixed structures of two or more oligonucleotides, modified oligonucleotides, oligonucleosides and/or oligonucleotide analogs as described above.

The oligonucleotide can be composed of regions that can be linked in "register," that is, when the monomers are linked consecutively, as in native DNA, or linked via spacers. The spacers are intended to constitute a covalent "bridge" between the regions and have in preferred cases a length not exceeding about 100 carbon atoms. The spacers may carry different functionalities, for example, having positive or negative charge, carry special nucleic acid binding properties (intercalators, groove binders, toxins, fluorophors etc.), being lipophilic, inducing special secondary structures like, for example, alanine containing peptides that induce alpha-helices.

As used herein, the term "monomers" typically indicates monomers linked by phosphodiester bonds or analogs thereof to form oligonucleotides ranging in size from a few monomeric units, e.g., from about 3-4, to about several hundreds of monomeric units. Analogs of phosphodiester linkages include: phosphorothioate, phosphorodithioate, methylphosphornates, phosphoroselenoate, phosphoramidate, and the like, as more fully described below.

In the present context, the terms "nucleobase" covers naturally occurring nucleobases as well as non-naturally occurring nucleobases. It should be clear to the person skilled in the art that various nucleobases which previously have been considered "non-naturally occurring" have subsequently been found in nature. Thus, "nucleobase" includes not only the known purine and pyrimidine heterocycles, but also heterocyclic analogues and tautomers thereof. Illustrative examples of nucleobases are adenine, guanine, thymine, cytosine, uracil, purine, xanthine, diaminopurine, 8-oxo-$N^6$-methyladenine, 7-deazaxanthine, 7-deazaguanine, $N^4,N^4$-ethanocytosin, $N^6,N^6$-ethano-2,6-diaminopurine, 5-methylcytosine, 5-($C^3$-$C^6$)-alkynylcytosine, 5-fluorouracil, 5-bromouracil, pseudoisocytosine, 2-hydroxy-5-methyl-4-triazolopyridin, isocytosine, isoguanin, inosine and the "non-naturally occurring" nucleobases described in Benner et al., U.S. Pat. No. 5,432,272. The term "nucleobase" is intended to cover every and all of these examples as well as analogues and tautomers thereof. Especially interesting nucleobases are adenine, guanine, thymine, cytosine, and uracil, which are considered as the naturally occurring nucleobases in relation to therapeutic and diagnostic application in humans.

As used herein, "nucleoside" includes the natural nucleosides, including 2'-deoxy and 2'-hydroxyl forms, e.g., as described in Kornberg and Baker, DNA Replication, 2nd Ed. (Freeman, San Francisco, 1992).

"Analogs" in reference to nucleosides includes synthetic nucleosides having modified base moieties and/or modified sugar moieties, e.g., described generally by Scheit, Nucleotide Analogs, John Wiley, New York, 1980; Freier & Altmann, *Nucl. Acid. Res.*, 1997, 25(22), 4429-4443, Toulmé, J. J., *Nature* Biotechnology 19:17-18 (2001); Manoharan M., *Biochemica et Biophysica Acta* 1489:117-139(1999); Freier S., M., *Nucleic Acid Research*, 25:4429-4443 (1997), Uhlman, E., *Drug Discovery & Development*, 3: 203-213 (2000), Herdewin P., *Antisense & Nucleic Acid Drug Dev.*, 10:297-310 (2000),; 2'-0, 3'-C-linked [3.2.0] bicycloarabinonucleosides (see e.g. N. K Christiensen., et al, *J. Am. Chem. Soc.*, 120: 5458-5463 (1998). Such analogs include synthetic nucleosides designed to enhance binding properties, e.g., duplex or triplex stability, specificity, or the like.

The term "stability" in reference to duplex or triplex formation generally designates how tightly an antisense oligonucleotide binds to its intended target sequence; more particularly, "stability" designates the free energy of formation of the duplex or triplex under physiological conditions. Melting temperature under a standard set of conditions, e.g., as described below, is a convenient measure of duplex and/or triplex stability. Preferably, oligonucleotides of the invention are selected that have melting temperatures of at least 45° C. when measured in 100 mM NaCl, 0.1 mM EDTA and 10 mM phosphate buffer aqueous solution, pH 7.0 at a strand concentration of both the oligonucleotide and the target nucleic acid of 1.5 µM. Thus, when used under physiological conditions, duplex or triplex formation will be substantially favored over the state in which the antigen and its target are dissociated. It is understood that a stable duplex or triplex may in some embodiments include mismatches between base pairs and/or among base triplets in the case of triplexes. Preferably, modified oligonucleotides, e.g. comprising LNA units, of the invention form perfectly matched duplexes and/or triplexes with their target nucleic acids.

As used herein, the term "downstream" when used in reference to a direction along a nucleotide sequence means in the direction from the 5' to the 3' end. Similarly, the term "upstream" means in the direction from the 3' to the 5' end.

As used herein, the term "gene" means the gene and all currently known variants thereof and any further variants which may be elucidated.

As used herein, "variant" of polypeptides refers to an amino acid sequence that is altered by one or more amino acid residues. The variant may have "conservative" changes, wherein a substituted amino acid has similar structural or chemical properties (e.g., replacement of leucine with isoleucine). More rarely, a variant may have "nonconservative" changes (e.g., replacement of glycine with tryptophan). Analogous minor variations may also include amino acid deletions or insertions, or both. Guidance in determining which amino acid residues may be substituted, inserted, or deleted without abolishing biological activity may be found using computer programs well known in the art, for example, LASERGENE software (DNASTAR).

The term "variant," when used in the context of a polynucleotide sequence, may encompass a polynucleotide sequence related to a wild type gene. This definition may also include, for example, "allelic," "splice," "species," or "polymorphic" variants. A splice variant may have significant identity to a reference molecule, but will generally have a greater or lesser number of polynucleotides due to alternate splicing of exons during mRNA processing. The corresponding polypeptide may possess additional functional domains or an absence of domains. Species variants are polynucleotide sequences that vary from one species to another. Of particular utility in the invention are variants of wild type target gene products. Variants may result from at least one mutation in the nucleic acid sequence and may result in altered mRNAs or in polypeptides whose structure or function may or may not be altered. Any given natural or recombinant gene may have none, one, or many allelic forms. Common mutational changes that give rise to variants are generally ascribed to natural deletions, additions, or substitutions of nucleotides. Each of these types of changes may occur alone, or in combination with the others, one or more times in a given sequence.

The resulting polypeptides generally will have significant amino acid identity relative to each other. A polymorphic variant is a variation in the polynucleotide sequence of a particular gene between individuals of a given species. Polymorphic variants also may encompass "single nucleotide polymorphisms" (SNPs) or single base mutations in which the polynucleotide sequence varies by one base. The presence of SNPs may be indicative of, for example, a certain population with a propensity for a disease state, that is susceptibility versus resistance.

As used herein, the term "mRNA" means the presently known mRNA transcript(s) of a targeted gene, and any further transcripts which may be elucidated.

By "desired RNA" molecule is meant any foreign RNA molecule which is useful from a therapeutic, diagnostic, or other viewpoint. Such molecules include antisense RNA molecules, decoy RNA molecules, enzymatic RNA, therapeutic editing RNA and agonist and antagonist RNA.

By "antisense RNA" is meant a non-enzymatic RNA molecule that binds to another RNA (target RNA) by means of RNA-RNA interactions and alters the activity of the target RNA (Eguchi et al., 1991 *Annu. Rev. Biochem.* 60, 631-652).

RNA interference "RNAi" is mediated by double stranded RNA (dsRNA) molecules that have sequence-specific homology to their "target" nucleic acid sequences (Caplen, N. J., et al., *Proc. Natl. Acad. Sci. USA* 98:9742-9747 (2001)). Biochemical studies in *Drosophila* cell-free lysates indicate that, in certain embodiments of the present invention, the mediators of RNA-dependent gene silencing are 21-25 nucleotide "small interfering" RNA duplexes (siRNAs). Accordingly, siRNA molecules are suitably used in methods of the present invention. The siRNAs are derived from the processing of dsRNA by an RNase enzyme known as Dicer (Bernstein, E., et al., *Nature* 409:363-366 (2001)). siRNA duplex products are recruited into a multi-protein siRNA complex termed RISC (RNA Induced Silencing Complex). Without wishing to be bound by any particular theory, a RISC is then believed to be guided to a target nucleic acid (suitably mRNA), where the siRNA duplex interacts in a sequence-specific way to mediate cleavage in a catalytic fashion (Bernstein, E., et al., *Nature* 409:363-366 (2001); Boutla, A., et al., *Curr. Biol.* 11:1776-1780 (2001)). Small interfering RNAs that can be used in accordance with the present invention can be synthesized and used according to procedures that are well known in the art and that will be familiar to the ordinarily skilled artisan. Small interfering RNAs for use in the methods of the present invention suitably comprise between about 0 to about 50 nucleotides (nt). In examples of nonlimiting embodiments, siRNAs can comprise about 5 to about 40 nt, about 5 to about 30 nt, about 10 to about 30 nt, about 15 to about 25 nt, or about 20-25 nucleotides. Selection of appropriate RNAi is facilitated by using computer programs that automatically align nucleic acid sequences and indicate regions of identity or homology. Such programs are used to compare nucleic acid sequences obtained, for example, by searching databases such as GenBank or by sequencing PCR products. Comparison of nucleic acid sequences from a range of species allows the selection of nucleic acid sequences that display an appropriate degree of identity between species. In the case of genes that have not been sequenced, Southern blots are performed to allow a determination of the degree of identity between genes in target species and other species. By performing Southern blots at varying degrees of stringency, as is well known in the art, it is possible to obtain an approximate measure of identity. These procedures allow the selection of RNAi that exhibit a high degree of complementarity to target nucleic acid sequences in a subject to be controlled and a lower degree of complementarity to corresponding nucleic acid sequences in other species. One skilled in the art will realize that there is considerable latitude in selecting appropriate regions of genes for use in the present invention.

By "enzymatic RNA" is meant an RNA molecule with enzymatic activity (Cech, 1988 *J. American. Med. Assoc.* 260, 3030-3035). Enzymatic nucleic acids (ribozymes) act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through base-pairing, and once bound to the correct site, acts enzymatically to cut the target RNA.

By "decoy RNA" is meant an RNA molecule that mimics the natural binding domain for a ligand. The decoy RNA therefore competes with natural binding target for the binding of a specific ligand. For example, it has been shown that over-expression of HIV trans-activation response (TAR) RNA can act as a "decoy" and efficiently binds HIV tat protein, thereby preventing it from binding to TAR sequences encoded in the HIV RNA (Sullenger et al., 1990, *Cell*, 63, 601-608). This is meant to be a specific example. Those in the art will recognize that this is but one example, and other embodiments can be readily generated using techniques generally known in the art.

The term, "complementary" means that two sequences are complementary when the sequence of one can bind to the sequence of the other in an anti-parallel sense wherein the 3'-end of each sequence binds to the 5'-end of the other sequence and each A, T(U), G, and C of one sequence is then aligned with a T(U), A, C, and G, respectively, of the other sequence. Normally, the complementary sequence of the oligonucleotide has at least 80% or 90%, preferably 95%, most preferably 100%, complementarity to a defined sequence. Preferably, alleles or variants thereof can be identified. A BLAST program also can be employed to assess such sequence identity.

The term "complementary sequence" as it refers to a polynucleotide sequence, relates to the base sequence in another nucleic acid molecule by the base-pairing rules. More particularly, the term or like term refers to the hybridization or base pairing between nucleotides or nucleic acids, such as, for instance, between the two strands of a double stranded DNA molecule or between an oligonucleotide primer and a primer binding site on a single stranded nucleic acid to be sequenced or amplified. Complementary nucleotides are, generally, A and T (or A and U), or C and G. Two single stranded RNA or DNA molecules are said to be substantially complementary when the nucleotides of one strand, optimally aligned and compared and with appropriate nucleotide insertions or deletions, pair with at least about 95% of the nucleotides of the other strand, usually at least about 98%, and more preferably from about 99% to about 100%. Complementary polynucleotide sequences can be identified by a variety of approaches including use of well-known computer algorithms and software, for example the BLAST program.

The term "stability" in reference to duplex or triplex formation generally designates how tightly an antisense oligonucleotide binds to its intended target sequence; more particularly, "stability" designates the free energy of formation of the duplex or triplex under physiological conditions. Melting temperature under a standard set of conditions, e.g., as described below, is a convenient measure of duplex and/or triplex stability. Preferably, oligonucleotides of the invention are selected that have melting temperatures of at least 45° C. when measured in 100 mM NaCl, 0.1 mM EDTA and 10 mM phosphate buffer aqueous solution, pH 7.0 at a strand concentration of both the oligonucleotide and the target nucleic acid of 1.5 µM. Thus, when used under physiological conditions, duplex or triplex formation will be substantially favored over the state in which the antigen and its target are dissociated. It is understood that a stable duplex or triplex may in some embodiments include mismatches between base pairs and/or among base triplets in the case of triplexes. Preferably, modified oligonucleotides, e.g. comprising LNA units, of the invention form perfectly matched duplexes and/or triplexes with their target nucleic acids.

As used herein, the term "Thermal Melting Point (Tm)" refers to the temperature, under defined ionic strength, pH, and nucleic acid concentration, at which 50% of the oligonucleotides complementary to the target sequence hybridize to the target sequence at equilibrium. As the target sequences are generally present in excess, at Tm, 50% of the oligonucleotides are occupied at equilibrium). Typically, stringent conditions will be those in which the salt concentration is at least about 0.01 to 1.0 M Na ion concentration (or other salts) at pH 7.0 to 8.3 and the temperature is at least about 30° C. for short oligonucleotides (e.g., 10 to 50 nucleotide). Stringent conditions may also be achieved with the addition of destabilizing agents such as formamide.

The term "stringent conditions" refers to conditions under which an oligonucleotide will hybridize to its target subsequence, but with only insubstantial hybridization to other sequences or to other sequences such that the difference may be identified. Stringent conditions are sequence-dependent and will be different in different circumstances. Longer sequences hybridize specifically at higher temperatures. Generally, stringent conditions are selected to be about 5° C. lower than the thermal melting point (Tm) for the specific sequence at a defined ionic strength and pH.

The term "target nucleic acid" refers to a nucleic acid (often derived from a biological sample), to which the oligonucleotide is designed to specifically hybridize. It is either the presence or absence of the target nucleic acid that is to be detected, or the amount of the target nucleic acid that is to be quantified. The target nucleic acid has a sequence that is complementary to the nucleic acid sequence of the corresponding oligonucleotide directed to the target. The term target nucleic acid may refer to the specific subsequence of a larger nucleic acid to which the oligonucleotide is directed or to the overall sequence (e.g., gene or mRNA) whose expression level it is desired to detect. The difference in usage will be apparent from context.

As used herein, a "pharmaceutically acceptable" component/carrier etc is one that is suitable for use with humans and/or animals without undue adverse side effects (such as toxicity, irritation, and allergic response) commensurate with a reasonable benefit/risk ratio.

As used herein, the term "safe and effective amount" refers to the quantity of a component which is sufficient to yield a desired therapeutic response without undue adverse side effects (such as toxicity, irritation, or allergic response) commensurate with a reasonable benefit/risk ratio when used in the manner of this invention. By "therapeutically effective amount" is meant an amount of a compound of the present invention effective to yield the desired therapeutic response. For example, an amount effective to delay the growth of or to cause a cancer, either a sarcoma or lymphoma, or to shrink the cancer or prevent metastasis. The specific safe and effective amount or therapeutically effective amount will vary with such factors as the particular condition being treated, the physical condition of the patient, the type of mammal or animal being treated, the duration of the treatment, the nature of concurrent therapy (if any), and the specific formulations employed and the structure of the compounds or its derivatives.

As used herein, a "pharmaceutical salt" include, but are not limited to, mineral or organic acid salts of basic residues such as amines; alkali or organic salts of acidic residues such as carboxylic acids. Preferably the salts are made using an organic or inorganic acid. These preferred acid salts are chlorides, bromides, sulfates, nitrates, phosphates, sulfonates, formates, tartrates, maleates, malates, citrates, benzoates, salicylates, ascorbates, and the like. The most preferred salt is the hydrochloride salt.

As used herein, "cancer" refers to all types of cancer or neoplasm or malignant tumors found in mammals, including, but not limited to: leukemias, lymphomas, melanomas, carcinomas and sarcomas. Examples of cancers are cancer of the brain, breast, pancreas, cervix, colon, head & neck, kidney, lung, non-small cell lung, melanoma, mesothelioma, ovary, sarcoma, stomach, uterus and Medulloblastoma.

Additional cancers which can be treated with siRNA's according to the invention include, for example, Hodgkin's Disease, Non-Hodgkin's Lymphoma, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, cervical cancer, endometrial cancer, adrenal cortical cancer, and prostate cancer. Cancers can also be the result of pathogens e.g. cervical cancer and human papilloma viruses. Therefore, in one embodiment, treatment of disease includes treating abnormalities induced by pathogens.

A "heterologous" component refers to a component that is introduced into or produced within a different entity from that in which it is naturally located. For example, a polynucleotide derived from one organism and introduced by genetic engineering techniques into a different organism is a heterologous polynucleotide which, if expressed, can encode a heterologous polypeptide. Similarly, a promoter or enhancer that is removed from its native coding sequence and operably linked to a different coding sequence is a heterologous promoter or enhancer.

A "promoter," as used herein, refers to a polynucleotide sequence that controls transcription of a gene or coding sequence to which it is operably linked. A large number of promoters, including constitutive, inducible and repressible promoters, from a variety of different sources, are well known in the art and are available as or within cloned polynucleotide sequences (from, e.g., depositories such as the ATCC as well as other commercial or individual sources).

An "enhancer," as used herein, refers to a polynucleotide sequence that enhances transcription of a gene or coding sequence to which it is operably linked. A large number of enhancers, from a variety of different sources are well known in the art and available as or within cloned polynucleotide sequences (from, e.g., depositories such as the ATCC as well as other commercial or individual sources). A number of polynucleotides comprising promoter sequences (such as the commonly-used CMV promoter) also comprise enhancer sequences.

"Operably linked" refers to a juxtaposition, wherein the components so described are in a relationship permitting them to function in their intended manner. A promoter is operably linked to a coding sequence if the promoter controls transcription of the coding sequence. Although an operably linked promoter is generally located upstream of the coding sequence, it is not necessarily contiguous with it. An enhancer is operably linked to a coding sequence if the enhancer increases transcription of the coding sequence. Operably linked enhancers can be located upstream, within or downstream of coding sequences. A polyadenylation sequence is operably linked to a coding sequence if it is located at the downstream end of the coding sequence such that transcription proceeds through the coding sequence into the polyadenylation sequence.

A "replicon" refers to a polynucleotide comprising an origin of replication which allows for replication of the polynucleotide in an appropriate host cell. Examples include replicons of a target cell into which a heterologous nucleic acid might be integrated (e.g., nuclear and mitochondrial chromosomes), as well as extrachromosomal replicons (such as replicating plasmids and episomes).

"Gene delivery," "gene transfer," and the like as used herein, are terms referring to the introduction of an exogenous polynucleotide (sometimes referred to as a "transgene products") into a host cell, irrespective of the method used for the introduction. Such methods include a variety of well-known techniques such as vector-mediated gene transfer (by, e.g., viral infection/transfection, or various other protein-based or lipid-based gene delivery complexes) as well as techniques facilitating the delivery of "naked" polynucleotides (such as electroporation, "gene gun" delivery and various other techniques used for the introduction of polynucleotides). The introduced polynucleotide may be stably or transiently maintained in the host cell. Stable maintenance typically requires that the introduced polynucleotide either contains an origin of replication compatible with the host cell or integrates into a replicon of the host cell such as an extrachromosomal replicon (e.g., a plasmid) or a nuclear or mitochondrial chromosome. A number of vectors are known to be capable of mediating transfer of gene products to mammalian cells, as is known in the art and described herein.

"In vivo" gene delivery, gene transfer, gene therapy and the like as used herein, are terms referring to the introduction of a vector comprising an exogenous polynucleotide directly into the body of an organism, such as a human or non-human mammal, whereby the exogenous polynucleotide is introduced to a cell of such organism in vivo.

A cell is "transduced" by a nucleic acid when the nucleic acid is translocated into the cell from the extracellular environment. Any method of transferring a nucleic acid into the cell may be used; the term, unless otherwise indicated, does not imply any particular method of delivering a nucleic acid into a cell. A cell is "transformed" by a nucleic acid when the nucleic acid is transduced into the cell and stably replicated. A vector includes a nucleic acid (ordinarily RNA or DNA) to be expressed by the cell. A vector optionally includes materials to aid in achieving entry of the nucleic acid into the cell, such as a viral particle, liposome, protein coating or the like. A "cell transduction vector" is a vector which encodes a nucleic acid capable of stable replication and expression in a cell once the nucleic acid is transduced into the cell.

As used herein, a "target cell" or "recipient cell" refers to an individual cell or cell which is desired to be, or has been, a recipient of exogenous nucleic acid molecules, polynucleotides and/or proteins. The term is also intended to include progeny of a single cell.

A "vector" (sometimes referred to as gene delivery or gene transfer "vehicle") refers to a macromolecule or complex of molecules comprising a polynucleotide to be delivered to a host cell, either in vitro or in vivo. The polynucleotide to be delivered may comprise a coding sequence of interest in gene therapy. Vectors include, for example, viral vectors (such as adenoviruses ("Ad"), adeno-associated viruses (AAV), and retroviruses), liposomes and other lipid-containing complexes, and other macromolecular complexes capable of mediating delivery of a polynucleotide to a host cell. Vectors can also comprise other components or functionalities that further modulate gene delivery and/or gene expression, or that otherwise provide beneficial properties to the targeted cells. As described and illustrated in more detail below, such other components include, for example, components that influence binding or targeting to cells (including components that mediate cell-type or tissue-specific binding); components that influence uptake of the vector nucleic acid by the cell; components that influence localization of the polynucleotide within the cell after uptake (such as agents mediating nuclear localization); and components that influence expression of the polynucleotide. Such components also might include markers, such as detectable and/or selectable markers that can be used to detect or select for cells that have taken up and are expressing the nucleic acid delivered by the vector. Such components can be provided as a natural feature of the vector (such as the use of certain viral vectors which have components or functionalities mediating binding and uptake), or vectors can be modified to provide such functionalities. Other vectors include those described by Chen et al; *BioTechniques,* 34: 167-171 (2003). A large variety of such vectors are known in the art and are generally available.

A "recombinant viral vector" refers to a viral vector comprising one or more heterologous gene products or sequences. Since many viral vectors exhibit size-constraints associated with packaging, the heterologous gene products or sequences are typically introduced by replacing one or more portions of the viral genome. Such viruses may become replication-defective, requiring the deleted function(s) to be provided in trans during viral replication and encapsidation (by using, e.g., a helper virus or a packaging cell line carrying gene products necessary for replication and/or encapsidation). Modified viral vectors in which a polynucleotide to be delivered is carried on the outside of the viral particle have also been described (see, e.g., Curiel, D T, et al. *PNAS* 88: 8850-8854, 1991).

Viral "packaging" as used herein refers to a series of intracellular events that results in the synthesis and assembly of a viral vector. Packaging typically involves the replication of the "pro-viral genome," or a recombinant pro-vector typically referred to as a "vector plasmid" (which is a recombinant polynucleotide than can be packaged in an manner analogous to a viral genome, typically as a result of being flanked by appropriate viral "packaging sequences"), followed by encapsidation or other coating of the nucleic acid. Thus, when a suitable vector plasmid is introduced into a packaging cell line under appropriate conditions, it can be replicated and assembled into a viral particle. Viral "rep" and "cap" gene products, found in many viral genomes, are gene products encoding replication and encapsidation proteins, respectively. A "replication-defective" or "replication-incompetent" viral vector refers to a viral vector in which one or more functions necessary for replication and/or packaging are missing or altered, rendering the viral vector incapable of initiating viral replication following uptake by a host cell. To produce stocks of such replication-defective viral vectors, the virus or pro-viral nucleic acid can be introduced into a "packaging cell line" that has been modified to contain gene products encoding the missing functions which can be supplied in trans). For example, such packaging gene products can be stably integrated into a replicon of the packaging cell line or they can be introduced by transfection with a "packaging plasmid" or helper virus carrying gene products encoding the missing functions.

A "detectable marker gene" is a gene that allows cells carrying the gene to be specifically detected (e.g., distinguished from cells which do not carry the marker gene). A large variety of such marker gene products are known in the art. Preferred examples thereof include detectable marker gene products which encode proteins appearing on cellular surfaces, thereby facilitating simplified and rapid detection and/or cellular sorting. By way of illustration, the lacZ gene encoding beta-galactosidase can be used as a detectable marker, allowing cells transduced with a vector carrying the lacZ gene to be detected by staining.

A "selectable marker gene" is a gene that allows cells carrying the gene to be specifically selected for or against, in the presence of a corresponding selective agent. By way of illustration, an antibiotic resistance gene can be used as a positive selectable marker gene that allows a host cell to be positively selected for in the presence of the corresponding antibiotic. Selectable markers can be positive, negative or bifunctional. Positive selectable markers allow selection for cells carrying the marker, whereas negative selectable markers allow cells carrying the marker to be selectively eliminated. A variety of such marker gene products have been described, including bifunctional (i.e. positive/negative) markers (see, e.g., WO 92/08796, published May 29, 1992, and WO 94/28143, published Dec. 8, 1994). Such marker gene products can provide an added measure of control that can be advantageous in gene therapy contexts.

"Diagnostic" or "diagnosed" means identifying the presence or nature of a pathologic condition. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay, are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

The terms "patient" or "individual" are used interchangeably herein, and refers to a mammalian subject to be treated, with human patients being preferred. In some cases, the methods of the invention find use in experimental animals, in veterinary application, and in the development of animal models for disease, including, but not limited to, rodents including mice, rats, and hamsters; and primates.

"Treatment" is an intervention performed with the intention of preventing the development or altering the pathology or symptoms of a disorder. Accordingly, "treatment" refers to both therapeutic treatment and prophylactic or preventative measures. "Treatment" may also be specified as palliative care. Those in need of treatment include those already with the disorder as well as those in which the disorder is to be prevented. In tumor (e.g., cancer) treatment, a therapeutic agent may directly decrease the pathology of tumor cells, or render the tumor cells more susceptible to treatment by other therapeutic agents, e.g., radiation and/or chemotherapy.

The "treatment of neoplastic disease, neoplastic cells, cancer", refers to an amount of the oligonucleotides, vectors and/or peptides, described throughout the specification and in the Examples which follow, capable of invoking one or more of the following effects: (1) inhibition, to some extent, of tumor growth, including, (i) slowing down and (ii) complete growth arrest; (2) reduction in the number of tumor cells; (3) maintaining tumor size; (4) reduction in tumor size; (5) inhibition, including (i) reduction, (ii) slowing down or (iii) complete prevention of tumor cell infiltration into peripheral organs; (6) inhibition, including (i) reduction, (ii) slowing down or (iii) complete prevention of metastasis; (7) enhancement of anti-tumor immune response, which may result in (i) maintaining tumor size, (ii) reducing tumor size, (iii) slowing the growth of a tumor, (iv) reducing, slowing or preventing invasion or (v) reducing, slowing or preventing metastasis; and/or (8) relief, to some extent, of one or more symptoms associated with the disorder.

Treatment of an individual suffering from an infectious disease organism refers to a decrease and elimination of the disease organism from an individual. For example, a decrease of viral particles as measured by plaque forming units or other automated diagnostic methods such as ELISA etc.

"Neural (neuronal, neurological) defects, disorders or diseases" as used herein refers to any neurological disorder or disease, including but not limited to neurodegenerative disorders (e.g. Parkinson's; Alzheimer's) or autoimmune disorders (e.g. multiple sclerosis) of the central nervous system; memory loss; long term and short term memory disorders; learning disorders; autism, depression, benign forgetfulness, childhood learning disorders, close head injury, and attention deficit disorder; autoimmune disorders of the brain, neuronal reaction to viral infection; brain damage; depression; psychiatric disorders such as bi-polarism, schizophrenia and the like; narcolepsy/sleep disorders (including circadian rhythm disorders, insomnia and narcolepsy); severance of nerves or nerve damage; severance of the cerebrospinal nerve cord (CNS) and any damage to brain or nerve cells; neurological deficits associated with AIDS; tics (e.g. Giles de la Tourette's syndrome); Huntington's chorea, schizophrenia, traumatic brain injury, tinnitus, neuralgia, especially trigeminal neuralgia, neuropathic pain, inappropriate neuronal activity resulting in neurodysthesias in diseases such as diabetes, MS and motor neuron disease, ataxias, muscular rigidity (spasticity) and temporomandibular joint dysfunction; Reward Deficiency Syndrome (RDS) behaviors in a subject; neurotoxicity caused by alcohol or substance abuse (e.g. ecstacy, methamphetamine, etc.). Other diseases include, but not limited to: Aphasia, Bell's Palsy, Creutzfeldt-Jakob Disease, Epilepsy, Encephalitis, Huntington's Disease, Neuromuscular Disorders Neuro-oncology, Neuro-immunology, Neuro-otology, Pain, Phobia, Sleep Disorders, and other movement disorders Other degenerative disorders include, for example, age related macular degeneration.

Target Nucleic Acids

The Concept of Non-Coding RNA (ncRNA): The central dogma of molecular biology has for over half a century stated that genetic information encoded in DNA is transcribed to form intermediary molecules of RNA, which are in turn translated into amino acids that make up proteins. The prevailing assumption has been that genes are directly related to proteins ("one gene-one protein"). In the past few years, we have come to realize that the complexity at the RNA level is far greater than previously assumed. Such complexity is largely due to non-coding transcripts (as well as alternative splicing phenomena) and is particularly apparent in eukaryotes (Mattick, J. S. (2004) RNA regulation: a new genetics? Nat Rev Genet 5 (4), 316-323).

ncRNAs comprise microRNAs, antisense transcripts and other Transcriptional Units (TU) containing a high density of stop codons and lacking any extensive "Open Reading Frame". Many ncRNAs appear to start from initiation sites in 3' untranslated regions (3'UTRs) of protein-coding loci. ncRNAs are often rare and at least half of the ncRNAs that have been sequenced by the FANTOM consortium seem not to be polyadenylated. Most researchers have for obvious reasons focused on polyadenylated mRNAs that are processed and exported to the cytoplasm. Recently, it was shown that the set of non-polyadenylated nuclear RNAs may be very large, and that many such transcripts arise from so-called intergenic regions (Cheng, J. et al. (2005) Transcriptional maps of 10 human chromosomes at 5-nucleotide resolution. Science 308 (5725), 1149-1154; Kapranov, P. et al. (2005) Examples of the complex architecture of the human transcriptome revealed by RACE and high-density tiling arrays. Genome Res 15 (7), 987-997); see also FIG. 1A.

The concept of ncRNA is still somewhat controversial largely because they share some but not all of the features of conventional coding RNA. It appears that some ncRNAs are highly conserved even in distant species. The large majority of ncRNAs analyzed by Carninci et al. (Carninci, P. et al. (2005) The transcriptional landscape of the mammalian genome. Science 309 (5740), 1559-1563) displayed positional conservation across species. In considering function, it is conceivable that the act of transcription from the particular location is either important or a consequence of genomic structure or sequence. The non-coding transcript may indeed function through some kind of sequence-specific interaction with the DNA sequence from which it is derived, or it may have other target(s). Interestingly, ncRNA transcripts seem to be evolving rapidly and the fact that they often are not well conserved does not necessarily mean that they lack function. There are at least four web-accessible databases on ncRNA (see Table 1).

TABLE 1

Databases containing non-coding RNA sequences

| Name | Reference Information |
|---|---|
| RNAdb | Pang, et al., 2005, RNAdb - a comprehensive mammalian noncoding RNA database, Nucleic Acids Research 33 (Database Issue): D125-D130 |
| Rfam | Gardner, et al., 2008, Rfam: updates to the RNA families database, Nucleic Acids Research doi: 10.1093/nar/gkn766<br>Griffiths-Jones, et al., 2003, Rfam: an RNA family database, Nucleic Acids Research Jan 1; 31(1): 439-41 |
| NONCODE | Liu, et al., 2005, NONCODE: an integrated knowledge database of non-coding RNAs Nucleic Acids Research, Vol. 33, Database issue D112-D115 |

TABLE 1-continued

Databases containing non-coding RNA sequences

| Name | Reference Information |
|---|---|
| ncRNADB | Szymanski, et al., 2007, Noncoding RNAs database (ncRNAdb), Nucleic Acids Research Jan; 35 (Database issue): D162-4. Epub 2006 Dec 14. |

The most common mechanism by which ncRNAs regulate gene expression is by base-pairing with target transcripts. The RNAs that function by base pairing can be grouped into (1) cis-encoded RNAs that are encoded at the same genetic location, but on the opposite strand to the RNAs they act upon and therefore display perfect complementarity to their target, and (2) trans-encoded RNAs that are encoded at a chromosomal location distinct from the RNAs they act upon and generally do not exhibit perfect base-pairing potential with their targets.

Antisense Transcription: Antisense transcripts can derive from coding as well as noncoding RNA (FIG. 1A). Strikingly, antisense transcription in mammals is far more prevalent than what could have been anticipated only a few years ago. Very recently, Katayama et al. (Katayama, S. et al. (2005) Antisense transcription in the mammalian transcriptome. Science 309 (5740), 1564-1566) showed that in mice, more than 72% of an genome-mapped transcriptional units (43,553) overlap with some cDNA, 5' or 3' expressed sequence tag (EST) sequence, or tag or tag-pair region mapped to the opposite strand. There is currently no reason to assume that the situation would be very different in humans.

It has, however, been argued that this transcriptional activity is largely "unintentional," representing "leakage" of the RNA transcription machinery. To the latter end, it has been demonstrated that antisense transcript pairs are considerably more likely to preserve their genomic organization throughout evolution as compared to non-antisense pairs. Moreover, expression analysis using strand-specific and conventional microarrays have indicated marked fluctuation in expression levels of sense-antisense pairs among various mouse tissues. It appears that large amounts of multiple-sized transcripts are expressed from the sense-antisense loci and that these tend to lack polyadenylated tails and exhibit nuclear localization.

There appear to exist three basic types of sense-antisense pairs: (1) head-to-head or divergent, (2) tail-to-tail or convergent, and (3) fully overlapping. The divergent (head-to-head) classes are the most prevalent (FIG. 1B).

A key functional question is whether natural antisense pairs could form a basis for endogenous RNA interference (RNAi). The very widespread occurrence of RNAi-based mechanisms in different biological systems and recent evidence demonstrating that at least in some species, a part of the RNAi pathway may occur in the nuclear compartment suggest a possible role for this process in antisense-mediated gene repression. According to this view, double stranded RNAs (dsRNAs) would be cleaved into siRNAs by Dicer or other RNaseIII family members. However, we have recently demonstrated that RNA regulation by natural antisense transcripts occurs through a pathway that is independent of Dicer associated RNAi in human cells (Faghihi, M. and Wahlestedt, C. (2005) RNA interference is not involved in natural antisense mediated regulation of gene expression in mammals. Genome Biol). Antisense-sense interaction phenomena affect different types of genes and are unevenly distributed across the genome.

RNA Targeting: Drug-discovery efforts have historically focused on the search for compounds that modulate the protein products of genes. Usually these compounds are agonists or antagonists of receptors, or compounds that inhibit or stimulate enzymes or protein-protein interactions. However, the interest in targeting RNA—for target validation and/or therapeutic purposes—is increasing, not least with the introduction of RNAi a few years ago. In addition, there are many on-going efforts aimed at targeting mRNA with small molecules, antisense oligonucleotides, ribozymes or aptamers.

Current drug therapy relates to only a few hundred endogenous targets, mainly receptors and enzymes. Genomics and transcriptomics efforts have identified many novel candidate drug targets that need to be validated. Although target validation studies, for example by manipulation at the RNA level, help to set priorities in the drug discovery process, they do not directly produce drug candidates. Thus, there is good reason to keep a focus on the well-established targets. If these turn out to be subjected to natural antisense regulation then it may be possible to try to address these "old" targets in a novel way, particularly if no drugs for these targets are available.

For protein coding genes, in energetic terms, post-transcriptional regulation is an expensive mechanism to control gene expression. The mRNA is only an intermediate in the multistep process from gene to active protein. If a cell would regulate this process only at the beginning, at the transcriptional level, it would save the energy needed to accommodate, degrade and recycle the mRNA molecules that are not used to synthesize proteins. To modulate the actions of ncRNA, the RNA level is obviously the only targeting option.

In a preferred embodiment, oligonucleotides are targeted to an anti-sense and a sense transcript of a target nucleic acid. The oligonucleotides can be (1) head-to-head or divergent, (2) tail-to-tail or convergent, and (3) fully overlapping. FIG. 1B provides a schematic illustration of the different types of orientation.

In another preferred embodiment, oligonucleotides target an anti-sense transcript ("discordant regulation") whereby, knocking down only the antisense transcript elevates the expression of the conventional (sense) gene. Thus, in one aspect of the invention, expression of a desired gene can be up-regulated. For example, should the target gene or nucleic acids encode for a known or putative drug target, then knockdown of its antisense counterpart would mimic the action of a receptor agonist or an enzyme stimulant. Table 2 gives examples where knockdown of antisense (coding as well as non-coding) transcripts was demonstrated to discordantly regulate sense expression. For example, in Parkinson's disease enhanced activity of the mitochondrially localized kinase, PINK1 (e.g. elevation of PINK1) would be desired:

```
PINK-AS siRNA-a:
                           (SEQ ID NO: 1)
GGAAGCTGTAGCTAGAACATCTGTT

PINK-AS_siRNA-b:
                           (SEQ ID NO: 2)
CAGGTAAGTAGTCTCCTCTATCATT

PINK-AS_siRNA-c:
                           (SEQ ID NO: 3)
TCTCAACCCAAAGCCTGCTTTGTTA
```

In a preferred embodiment, siRNA molecules target overlapping regions of a desired sense/antisense locus, thereby modulating both the sense and antisense transcripts.

In a preferred embodiment, a composition comprises siRNA molecules, of either one or more, and/or, combinations of siRNAs, siRNAs that overlap a desired target locus, and/or target both sense and antisense (overlapping or otherwise). These molecules can be directed to any target that is desired for potential therapy of any disease or abnormality. For example, target cancer genes, receptors, genes encoding for promoters, enhancers, cytokines, etc. Theoretically there is no limit as to which molecule is to be targeted. This invention usher's a new era in designing therapies for each disease, abnormality whether congenital or otherwise. Furthermore, the technologies taught herein allow for tailoring therapies to each individual.

Another example whereby upregulation of gene expression would be desired using the compositions and methods of the invention, is the upregulation of angiogenesis, such as for example, in wound healing. To stimulate angiogenesis, enhanced signaling through the G-protein-coupled receptor (GPCR), CD97, could be achieved by targeting of its (coding) antisense partner, Ddx-39.

In another preferred embodiment, oligonucleotides target both anti-sense and sense transcript ("concordant regulation") whereby, knocking down both antisense and sense transcripts and thereby achieve synergistic reduction of the conventional (sense) gene expression. These concepts are illustrated in FIGS. 1A-1B and 2A-2B. If, siRNA is used to achieve knockdown, then this strategy is further tested by applying one siRNA targeted to the sense transcript and another siRNA to the corresponding antisense transcript, or a single energetically symmetric siRNA that simultaneously targets overlapping sense and antisense transcripts. As follows from Table 2, such dual concomitant targeting will, for example be relevant to pursue in the case of hypoxia-inducible factor 1 alpha, a target whose inhibition may be beneficial in various medical conditions. Another example in Table 2 is the Adrenomedullin AM1 receptor, a GPCR where reduced signaling could also prove to be of therapeutic benefit.

An example of compositions useful in concomitant knockdown of antisense and sense transcripts for use in Alzheimer's disease, include, but not limited to:

```
BACE1-AS:
siRNA-a:
                           (SEQ ID NO: 4)
CCCTCTGACACTGTACCATCTCTTT siRNA-b:
                           (SEQ ID NO: 5)
AGAAGGGTCTAAGTGCAGACATCTG siRNA-c:
                           (SEQ ID NO: 6)
CCAGAAGAGAAAGGGCACT

BACE1:
siRNA-a:
                           (SEQ ID NO: 7)
GAGCCTTTCTTTGACTCTCTGGTAA siRNA-b:
                           (SEQ ID NO: 8)
CCACGGAGAAGTTCCCTGATGGTTT
```

These compositions are provided as illustrative examples and are not meant to be limiting. In preferred embodiments, the oligonucleotides can be tailored to individual therapy, for example, these oligonucleotides can be sequence specific for allelic variants in individuals, the up-regulation or inhibition of a target can be manipulated in varying degrees, such as for example, 10%, 20%, 40%, 100% expression relative to the control. That is, in some patients it may be effective to increase or decrease target gene expression by 10% versus 80% in another patient.

Up-regulation or inhibition of gene expression may be quantified by measuring either the endogenous target RNA or the protein produced by translation of the target RNA. Techniques for quantifying RNA and proteins are well known to one of ordinary skill in the art. In certain preferred embodiments, gene expression is inhibited by at least 10%, preferably by at least 33%, more preferably by at least 50%, and yet more preferably by at least 80%. In particularly preferred embodiments, of the invention gene expression is inhibited by at least 90%, more preferably by at least 95%, or by at least 99% up to 100% within cells in the organism. In certain preferred embodiments, gene expression is up-regulated by at least 10%, preferably by at least 33%, more preferably by at least 50%, and yet more preferably by at least 80%. In particularly preferred embodiments, of the invention gene expression is up-regulated by at least 90%, more preferably by at least 95%, or by at least 99% up to 100% within cells in the organism.

Selection of appropriate RNAi is facilitated by using computer programs that automatically align nucleic acid sequences and indicate regions of identity or homology. Such programs are used to compare nucleic acid sequences obtained, for example, by searching databases such as GenBank or by sequencing PCR products. Comparison of nucleic acid sequences from a range of species allows the selection of nucleic acid sequences that display an appropriate degree of identity between species. In the case of genes that have not been sequenced, Southern blots are performed to allow a determination of the degree of identity between genes in target species and other species. By performing Southern blots at varying degrees of stringency, as is well known in the art, it is possible to obtain an approximate measure of identity. These procedures allow the selection of RNAi that exhibit a high degree of complementarity to target nucleic acid sequences in a subject to be controlled and a lower degree of complementarity to corresponding nucleic acid sequences in other species. One skilled in the art will realize that there is considerable latitude in selecting appropriate regions of genes for use in the present invention.

In a preferred embodiment, small interfering RNA (siRNA) either as RNA itself or as DNA, is delivered to a cell using an expression plasmid or virus and the coding sequence for small hairpin RNAs that are processed to siRNAs.

In another preferred embodiment, a DNA cassette for the cloning of small hairpin sequences permit their expression and processing using RNA polymerase I, II or III. This system enables efficient transport of the pre-siRNAs to the cytoplasm where they are active and permit the use of regulated and tissue specific promoters for gene expression.

In accordance with the invention target cells, either prokaryotic and eukaryotic, are selectively targeted by an siRNA based on their genetic makeup. Infectious disease almost invariably results in the acquisition of foreign nucleic acids, which could be targeted using this technology. Specific targets could be viral, e.g. HIV (virus or provirus) or bacterial, e.g. multi-drug resistant bacteria e.g. TB, fungal or protoazoan. This technology can be especially useful in treating infections for which there is no effective anti-microbial or anti-viral agent (e.g. Ebola virus, etc.), or known or novel bio-terrorist agents.

Preferred siRNA's of the invention will hybridize (bind) to a target sequence, particularly a target oligonucleotide of a disease, e.g. Parkinson's, Alzheimer's and the like, cancer, neural diseases, an infectious agent such as a viral, bacterial, fungal or protozoan agent under stringency conditions as may be assessed in vitro.

The invention may be used against protein coding gene products as well as non-protein coding gene products. Examples of non-protein coding gene products include gene products that encode ribosomal RNAs, transfer RNAs, small nuclear RNAs, small cytoplasmic RNAs, telomerase RNA, RNA molecules involved in DNA replication, chromosomal rearrangement and the like.

In another preferred embodiment, abnormal or cancer cells are targeted by the siRNAs. For example, many malignancies are associated with the presence of foreign DNA, e.g. Bcr-Abl, Bcl-2, HPV, and these provide unique molecular targets to permit selective malignant cell targeting. The approach can be used to target single base substitutions (e.g. K-ras, p53) or methylation changes. However, proliferation of cancer cells may also be caused by previously unexpressed gene products. These gene sequences can be targeted, thereby, inhibiting further expression and ultimate death of the cancer cell. In other instances, transposons can be the cause of such deregulation and transposon sequences can be targeted, e.g. Tn5.

According to the present invention, an siRNA oligonucleotide is designed to be specific for a molecule, which either causes, participates in, or aggravates a disease state, in a patient. For example, in a viral infection, an siRNA can be targeted against molecules responsible for viral replication; a viral infection cycle, such as, for example, attachment to cellular ligands; viral gene products encoding host immune modulating functions. Particularly preferred viral organisms causing human diseases according to the present invention include (but not restricted to) Filoviruses, Herpes viruses, Hepatitisviruses, Retroviruses, Orthomyxoviruses, Paramyxoviruses, Togaviruses, Picornaviruses, Papovaviruses and Gastroenteritisviruses.

In another preferred embodiment, the siRNA's are targeted to toxins produced by a disease agent such as anthrax. For example, anthrax which is one of the agents that can be used in a bioterrorist attack. Anthrax infection is mediated by spores of *Bacillus* anthraces, which can gain entry to the body through breaks in the skin, through inhalation, or through ingestion. Fatal anthrax is characterized by the establishment of a systemic bacteremia that is accompanied by an overwhelming toxemia. It seems that anthrax is a two-pronged attack with the bacteremia and/or toxemia contributing to the fatal syndrome of shock, hypoperfusion, and multiple organ system failure. The likelihood of developing systemic disease varies with the portal of organism entry, and is most pronounced for the inhalational route (reviewed in Dixon et al., 1999, *New England J. Med.* 341: 815-826). siRNA oligonucleotides can be targeted to the mRNAs that inhibit proliferation of the bacteria in an infected patient and target the toxin producing gene products thereby eliminating the toxic effects of the anthrax infection. Alternatively, siRNA's could be targeted to any sequence target that is present in the organism and lacking in the host.

The invention in general provides a method for treating diseases, such as cancer and diseases which are caused by infectious agents such as viruses, intra- and extra-cellular parasites, insertion elements, fungal infections, etc., which may also cause expression of gene products by a normally unexpressed gene, abnormal expression of a normally expressed gene or expression of an abnormal gene, comprising administering to a patient in need of such treatment an effective amount of an siRNA oligonucleotide; or a cocktail of different modified siRNA's; or a cocktail of different modified and unmodified siRNA oligonucleotides specific for the disease causing entity.

In accordance with the invention, siRNA oligonucleotide therapies comprise administered siRNA oligonucleotide which contacts (interacts with) the targeted mRNA from the gene, whereby expression of the gene is modulated, and expression is inhibited. Such modulation of expression suitably can be a difference of at least about 10% or 20% relative to a control, more preferably at least about 30%, 40%, 50%, 60%, 70%, 80%, or 90% difference in expression relative to a control. It will be particularly preferred where interaction or contact with an siRNA oligonucleotide results in complete or essentially complete modulation of expression relative to a control, e.g., at least about a 95%, 97%, 98%, 99% or 100% inhibition of or increase in expression relative to control. A control sample for determination of such modulation can be comparable cells (in vitro or in vivo) that have not been contacted with the siRNA oligonucleotide.

The methods of the invention are preferably employed for treatment or prophylaxis against diseases caused abnormal cell growth and by infectious agents, particularly for treatment of infections as may occur in tissue such as lung, heart, liver, prostate, brain, testes, stomach, intestine, bowel, spinal cord, sinuses, urinary tract or ovaries of a subject. The methods of the invention also may be employed to treat systemic conditions such as viremia or septicemia. The methods of the invention are also preferably employed for treatment of diseases and disorders associated with viral infections or bacterial infections, as well as any other disorder caused by an infectious agent.

Preferably, a disease agent is isolated from a patient and identified using diagnostic tools such as ELISA's RIAs, cell sorting, PCR and the like. However, a disease causing agent may be a novel agent to which siRNA oligonucleotides can be targeted. Sequencing data obtained from the agent can be used to construct an siRNA. Partial sequencing of the agent can be accomplished by any means known in the art. As an illustrative example which is not meant to limit or construe the invention in any way, the following is provided. The siRNA is designed to be complementary to selected sequences.

According to one preferred embodiment of the invention, the nucleobases in the siRNA may be modified to provided higher specificity and affinity for a target mRNA. For example nucleobases may be substituted with LNA monomers, which can be in contiguous stretches or in different positions. The modified siRNA, preferably has a higher association constant ($K_a$) for the target sequences than the complementary sequence. Binding of the modified or non-modified siRNA's to target sequences can be determined in vitro under a variety of stringency conditions using hybridization assays and as described in the examples which follow.

A fundamental property of oligonucleotides that underlies many of their potential therapeutic applications is their ability to recognize and hybridize specifically to complementary single stranded nucleic acids employing either Watson-Crick hydrogen bonding (A-T and G-C) or other hydrogen bonding schemes such as the Hoogsteen/reverse Hoogsteen mode. Affinity and specificity are properties commonly employed to characterize hybridization characteristics of a particular oligonucleotide. Affinity is a measure of the binding strength of the oligonucleotide to its complementary target (expressed as the thermostability ($T_m$) of the duplex). Each nucleobase pair in the duplex adds to the thermostability and thus affinity increases with increasing size (No. of nucleobases) of the oligonucleotide. Specificity is a measure of the ability of the oligonucleotide to discriminate between a fully complementary and a mismatched target sequence. In other words, specificity is a measure of the loss of affinity associated with mismatched nucleobase pairs in the target.

The utility of an siRNA oligonucleotide for modulation (including inhibition) of an mRNA can be readily determined by simple testing. Thus, an in vitro or in vivo expression system comprising the targeted mRNA, mutations or fragments thereof, can be contacted with a particular siRNA oligonucleotide (modified or un modified) and levels of expression are compared to a control, that is, using the identical expression system which was not contacted with the siRNA oligonucleotide.

siRNA oligonucleotides may be used in combinations. For instance, a cocktail of several different siRNA modified and/or unmodified oligonucleotides, directed against different regions of the same gene, may be administered simultaneously or separately.

In the practice of the present invention, target gene products may be single-stranded or double-stranded DNA or RNA. Short dsRNA can be used to block transcription if they are of the same sequence as the start site for transcription of a particular gene. See, for example, Janowski et al. *Nature Chemical Biology*, 2005, 10:1038. It is understood that the target to which the siRNA oligonucleotides of the invention are directed include allelic forms of the targeted gene and the corresponding mRNAs including splice variants. There is substantial guidance in the literature for selecting particular sequences for siRNA oligonucleotides given a knowledge of the sequence of the target polynucleotide. Preferred mRNA targets include the 5' cap site, tRNA primer binding site, the initiation codon site, the mRNA donor splice site, and the mRNA acceptor splice site.

Where the target polynucleotide comprises a mRNA transcript, sequence complementary oligonucleotides can hybridize to any desired portion of the transcript. Such oligonucleotides are, in principle, effective for inhibiting translation, and capable of inducing the effects described herein. It is hypothesized that translation is most effectively inhibited by the mRNA at a site at or near the initiation codon. Thus, oligonucleotides complementary to the 5'-region of mRNA transcript are preferred. Oligonucleotides complementary to the mRNA, including the initiation codon (the first codon at the 5' end of the translated portion of the transcript), or codons adjacent to the initiation codon, are preferred.

Chimeric/Modified siRNA

In accordance with this invention, persons of ordinary skill in the art will understand that mRNA includes not only the coding region which carries the information to encode a protein using the three letter genetic code, including the translation start and stop codons, but also associated ribonucleotides which form a region known to such persons as the 5'-untranslated region, the 3'-untranslated region, the 5' cap region, intron regions and intron/exon or splice junction ribonucleotides. Thus, oligonucleotides may be formulated in accordance with this invention which are targeted wholly or in part to these associated ribonucleotides as well as to the coding ribonucleotides. In preferred embodiments, the oligonucleotide is targeted to a translation initiation site (AUG codon) or sequences in the coding region, 5' untranslated region or 3'-untranslated region of an mRNA. The functions of messenger RNA to be interfered with include all vital functions such as translocation of the RNA to the site for protein translation, actual translation of protein from the RNA, splicing or maturation of the RNA and possibly even independent catalytic activity which may be engaged in by the RNA. The overall effect of such interference with the RNA function is to cause interference with protein expression.

Certain preferred oligonucleotides of this invention are chimeric oligonucleotides. "Chimeric oligonucleotides" or "chimeras," in the context of this invention, are oligonucleotides which contain two or more chemically distinct regions, each made up of at least one nucleotide. These oligonucleotides typically contain at least one region of modified nucleotides that confers one or more beneficial properties (such as, for example, increased nuclease resistance, increased uptake into cells, increased binding affinity for the RNA target) and a region that is a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of antisense inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art. In one preferred embodiment, a chimeric oligonucleotide comprises at least one region modified to increase target binding affinity, and, usually, a region that acts as a substrate for RNAse H. Affinity of an oligonucleotide for its target (in this case, a nucleic acid encoding ras) is routinely determined by measuring the $T_m$ of an oligonucleotide/target pair, which is the temperature at which the oligonucleotide and target dissociate; dissociation is detected spectrophotometrically. The higher the $T_m$, the greater the affinity of the oligonucleotide for the target. In a more preferred embodiment, the region of the oligonucleotide which is modified comprises at least one nucleotide modified at the 2' position of the sugar, most preferably a 2'-O-alkyl, 2'-O-alkyl-O-alkyl or 2'-fluoro-modified nucleotide. In other preferred embodiments, RNA modifications include 2'-fluoro, 2'-amino and 2' O-methyl modifications on the ribose of pyrimidines, abasic residues or an inverted base at the 3' end of the RNA. Such modifications are routinely incorporated into oligonucleotides and these oligonucleotides have been shown to have a higher $T_m$ (i.e., higher target binding affinity) than; 2'-deoxyoligonucleotides against a given target. The effect of such increased affinity is to greatly enhance RNAi oligonucleotide inhibition of gene expression. RNAse H is a cellular endonuclease that cleaves the RNA strand of RNA:DNA duplexes; activation of this enzyme therefore results in cleavage of the RNA target, and thus can greatly enhance the efficiency of RNAi inhibition. Cleavage of the RNA target can be routinely demonstrated by gel electrophoresis. In another preferred embodiment, the chimeric oligonucleotide is also modified to enhance nuclease resistance. Cells contain a variety of exo- and endo-nucleases which can degrade nucleic acids. A number of nucleotide and nucleoside modifications have been shown to make the oligonucleotide into which they are incorporated more resistant to nuclease digestion than the native oligodeoxynucleotide. Nuclease resistance is routinely measured by incubating oligonucleotides with cellular extracts or isolated nuclease solutions and measuring the extent of intact oligonucleotide remaining over time, usually by gel electrophoresis. Oligonucleotides which have been modified to enhance their nuclease resistance survive intact for a longer time than unmodified oligonucleotides. A variety of oligonucleotide modifications have been demonstrated to enhance or confer nuclease resistance. Oligonucleotides which contain at least one phosphorothioate modification are presently more preferred. In some cases, oligonucleotide modifications which enhance target binding affinity are also, independently, able to enhance nuclease resistance. Some desirable modifications can be found in De Mesmaeker et al. Acc. Chem. Res. 1995, 28:366-374.

Specific examples of some preferred oligonucleotides envisioned for this invention include those comprising modified backbones, for example, phosphorothioates, phosphotriesters, methyl phosphonates, short chain alkyl or cycloalkyl intersugar linkages or short chain heteroatomic or heterocyclic intersugar linkages. Most preferred are oligonucleotides with phosphorothioate backbones and those with heteroatom backbones, particularly $CH_2$—NH—O—$CH_2$, CH, —N($CH_3$)—O—$CH_2$ [known as a methylene (methylimino) or MMI backbone], $CH_2$—O—N($CH_3$)—$CH_2$, $CH_2$—N($CH_3$)—N ($CH_3$)—$CH_2$ and O—N($CH_3$)—$CH_2$—$CH_2$ backbones, wherein the native phosphodiester backbone is represented as O—P—O—$CH$,). The amide backbones disclosed by De Mesmaeker et al. Acc. Chem. Res. 1995, 28:366-374) are also preferred. Also preferred are oligonucleotides having morpholino backbone structures (Summerton and Weller, U.S. Pat. No. 5,034,506). In other preferred embodiments, such as the peptide nucleic acid (PNA) backbone, the phosphodiester backbone of the oligonucleotide is replaced with a polyamide backbone, the nucleobases being bound directly or indirectly to the aza nitrogen atoms of the polyamide backbone (Nielsen et al. Science 1991, 254, 1497). Oligonucleotides may also comprise one or more substituted sugar moieties. Preferred oligonucleotides comprise one of the following at the 2' position: OH, SH, $SCH_3$, F, OCN, $OCH_3$ $OCH_3$, $OCH_3$ O ($CH_2$)—$CH_3$, O($CH_2$)—$NH_2$ or O($CH_2$)—$CH_3$ where n is from 1 to about 10; $C_1$ to $C_{10}$ lower alkyl, alkoxyalkoxy, substituted lower alkyl, alkaryl or aralkyl; Cl; Br; CN; $CF_3$; $OCF_3$; O—, S—, or N-alkyl; O—, S—, or N-alkenyl; $SOCH_3$; $SO_2$ $CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. A preferred modification includes 2'-methoxyethoxy [2'-O—$CH_2$ $CH_2$ $OCH_3$, also known as 2'-O-(2-methoxyethyl)] (Martin et al., Helv. Chim. Acta, 1995, 78, 486). Other preferred modifications include 2'-methoxy (2'-O—$CH_3$), 2'-propoxy (2'-$OCH_2$ $CH_2CH_3$) and 2'-fluoro (2'-F). Similar modifications may also be made at other positions on the oligonucleotide, particularly the 3' position of the sugar on the 3' terminal nucleotide and the 5' position of 5' terminal nucleotide. Oligonucleotides may also have sugar mimetics such as cyclobutyls in place of the pentofuranosyl group.

Oligonucleotides may also include, additionally or alternatively, nucleobase (often referred to in the art simply as "base") modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, as well as synthetic nucleobases, e.g., 2-aminoadenine, 2-(methylamino)adenine, 2-(imidazolylalkyl)adenine, 2-(aminoalklyamino)adenine or other heterosubstituted alkyladenines, 2-thiouracil, 2-thiothymine, 5-bromouracil, 5-hydroxymethyluracil, 8-azaguanine, 7-deazaguanine, $N_6$ (6-aminohexyl)adenine and 2,6-diaminopurine. Kornberg, A., DNA Replication, W. H. Freeman & Co., San Francisco, 1980, pp 75-77; Gebeyehu, G., et al. Nucl. Acids Res. 1987, 15:4513). A "universal" base known in the art, e.g., inosine, may be included. 5-Me-C substitutions have been shown to increase nucleic acid duplex stability by 0.6-1.2° C. (Sanghvi, Y. S., in Crooke, S. T. and Lebleu, B., eds., Antisense Research and Applications, CRC Press, Boca Raton, 1993, pp. 276-278) and are presently preferred base substitutions.

Another modification of the oligonucleotides of the invention involves chemically linking to the oligonucleotide one or more moieties or conjugates which enhance the activity or cellular uptake of the oligonucleotide. Such moieties include but are not limited to lipid moieties such as a cholesterol moiety, a cholesteryl moiety (Letsinger et al., *Proc. Natl. Acad. Sci. USA* 1989, 86, 6553), cholic acid (Manoharan et al. *Bioorg. Med. Chem. Let.* 1994, 4, 1053), a thioether, e.g., hexyl-S-tritylthiol (Manoharan et al. *Ann. N.Y. Acad. Sci.* 1992, 660, 306; Manoharan et al. *Bioorg. Med. Chem. Let.* 1993, 3, 2765), a thiocholesterol (Oberhauser et al., *Nucl. Acids Res.* 1992, 20, 533), an aliphatic chain, e.g., dodecandiol or undecyl residues (Saison-Behmoaras et al. *EMBO J.* 1991, 10, 111; Kabanov et al. *FEBS Lett.* 1990, 259, 327; Svinarchuk et al. *Biochimie* 1993, 75, 49), a phospholipid, e.g., di-hexadecyl-rac-glycerol or triethylammonium 1,2-di-O-hexadecyl-rac-glycero-3-H-phosphonate (Manoharan et al. *Tetrahedron Lett.* 1995, 36, 3651; Shea et al. *Nucl. Acids Res.* 1990, 18, 3777), a polyamine or a polyethylene glycol chain (Manoharan et al. *Nucleosides & Nucleotides* 1995, 14, 969), or adamantane acetic acid (Manoharan et al. *Tetrahedron Lett.* 1995, 36, 3651). Oligonucleotides comprising lipophilic moieties, and methods for preparing such oligonucleotides are known in the art, for example, U.S. Pat. Nos. 5,138,045, 5,218,105 and 5,459,255.

It is not necessary for all positions in a given oligonucleotide to be uniformly modified, and in fact more than one of the aforementioned modifications may be incorporated in a single oligonucleotide or even at within a single nucleoside within an oligonucleotide. The present invention also includes oligonucleotides which are chimeric oligonucleotides as hereinbefore defined.

In another embodiment, the nucleic acid molecule of the present invention is conjugated with another moiety including but not limited to abasic nucleotides, polyether, polyamine, polyamides, peptides, carbohydrates, lipid, or polyhydrocarbon compounds. Those skilled in the art will recognize that these molecules can be linked to one or more of any nucleotides comprising the nucleic acid molecule at several positions on the sugar, base or phosphate group.

The oligonucleotides used in accordance with this invention may be conveniently and routinely made through the well-known technique of solid phase synthesis. Equipment for such synthesis is sold by several vendors including Applied Biosystems. Any other means for such synthesis may also be employed; the actual synthesis of the oligonucleotides is well within the talents of one of ordinary skill in the art. It is also well known to use similar techniques to prepare other oligonucleotides such as the phosphorothioates and alkylated derivatives. It is also well known to use similar techniques and commercially available modified amidites and controlled-pore glass (CPG) products such as biotin, fluorescein, acridine or psoralen-modified amidites and/or CPG (available from Glen Research, Sterling Va.) to synthesize fluorescently labeled, biotinylated or other modified oligonucleotides such as cholesterol-modified oligonucleotides.

In accordance with the invention, use of modifications such as the use of LNA monomers to enhance the potency, specificity and duration of action and broaden the routes of administration of oligonucleotides comprised of current chemistries such as MOE, ANA, FANA, PS etc (ref: Recent advances in the medical chemistry of antisense oligonucleotide by Uhlman, Current Opinions in Drug Discovery & Development 2000 Vol 3 No 2). This can be achieved by substituting some of the monomers in the current oligonucleotides by LNA monomers. The LNA modified oligonucleotide may have a size similar to the parent compound or may be larger or preferably smaller. It is preferred that such LNA-modified oligonucleotides contain less than about 70%, more preferably less than about 60%, most preferably less than about 50% LNA monomers and that their sizes are between about 10 and 25 nucleotides, more preferably between about 12 and 20 nucleotides.

Cancer Therapy

In another preferred embodiment, the siRNA oligonucleotides are used to treat patients susceptible to or suffering from cancer. Gene products which are over expressed in a cancer cell can be identified so that the siRNA oligonucleotide selectively targets the cancer cell as opposed to normal cells. For example, Expressed Sequenced Tags (ESTs), can be used to identify nucleic acid molecules which are over expressed in a cancer cell [expressed sequence tag (EST) sequencing (Celis, et al., *FEBS Lett.*, 2000, 480, 2-16; Larsson, et al., *J. Biotechnology.*, 2000, 80, 143-57)]. ESTs from a variety of databases can be identified. For example, preferred databases include, for example, Online Mendelian Inheritance in Man (OMIM), the Cancer Genome Anatomy Project (CGAP), GenBank, EMBL, PIR, SWISS-PROT, and the like. OMIM, which is a database of genetic mutations associated with disease, was developed, in part, for the National Center for Biotechnology Information (NCBI). OMIM can be accessed through the world wide web of the Internet, at, for example, ncbi.nlm.nih.gov/Omim/. CGAP, which is an interdisciplinary program to establish the information and technological tools required to decipher the molecular anatomy of a cancer cell. CGAP can be accessed through the world wide web of the Internet, at, for example, ncbi.nlm.nih.gov/ncicgap/. Some of these databases may contain complete or partial nucleotide sequences. In addition, alternative transcript forms can also be selected from private genetic databases. Alternatively, nucleic acid molecules can be selected from available publications or can be determined especially for use in connection with the present invention.

Alternative transcript forms can be generated from individual ESTs which are within each of the databases by computer software which generates contiguous sequences. In another embodiment of the present invention, the nucleotide sequence of the target nucleic acid molecule is determined by assembling a plurality of overlapping ESTs. The EST database (dbEST), which is known and available to those skilled in the art, comprises approximately one million different human mRNA sequences comprising from about 500 to 1000 nucleotides, and various numbers of ESTs from a number of different organisms. dbEST can be accessed through the world wide web of the Internet, at, for example, ncbi.nlm.nih.gov/dbEST/index.html. These sequences are derived from a cloning strategy that uses cDNA expression clones for genome sequencing. ESTs have applications in the discovery of new gene products, mapping of genomes, and identification of coding regions in genomic sequences. Another important feature of EST sequence information that is becoming rapidly available is tissue-specific gene expression data. This can be extremely useful in targeting mRNA from selective gene(s) for therapeutic intervention. Since EST sequences are relatively short, they must be assembled in order to provide a complete sequence. Because every available clone is sequenced, it results in a number of overlapping regions being reported in the database. The end result is the elicitation of alternative transcript forms from, for example, normal cells and cancer cells.

Assembly of overlapping ESTs extended along both the 5' and 3' directions results in a full-length "virtual transcript." The resultant virtual transcript may represent an already characterized nucleic acid or may be a novel nucleic acid with no known biological function. The Institute for Genomic Research (TIGR) Human Genome Index (HGI) database, which is known and available to those skilled in the art, contains a list of human transcripts. TIGR can be accessed through the world wide web of the Internet, at, for example, tigr.org. Transcripts can be generated in this manner using TIGR-Assembler, an engine to build virtual transcripts and which is known and available to those skilled in the art. TIGR-Assembler is a tool for assembling large sets of overlapping sequence data such as ESTs, BACs, or small genomes, and can be used to assemble eukaryotic or prokaryotic sequences. TIGR-Assembler is described in, for example, Sutton, et al., *Genome Science & Tech.*, 1995, 1, 9-19, which is incorporated herein by reference, and can be accessed through the file transfer program of the Internet, at, for example, tigr.org/pub/software/TIGR. assembler. In addition, GLAXO-MRC, which is known and available to those skilled in the art, is another protocol for constructing virtual transcripts. Identification of ESTs and generation of contiguous ESTs to form full length RNA molecules is described in detail in U.S. application Ser. No. 09/076,440, which is incorporated herein by reference.

Gene products which are overexpressed by cancer cells as compared to normal cells, for example, gene products expressed at least 5 fold greater in pancreatic cancers compared to normal tissues can be identified. Gene expression can be analyzed by Serial Analysis of Gene Expression (SAGE), which is based on the identification of and characterization of partial, defined sequences of transcripts corresponding to gene segments [SAGE (serial analysis of gene expression) (Madden, et al., *Drug Discov. Today*, 2000, 5, 415-425)]. These defined transcript sequence "tags" are markers for gene products which are expressed in a cell, a tissue, or an extract, for example.

Identification of Target Nucleic Acid Sequences

In a preferred embodiment, the compositions of the invention target desired nucleic acid sequences. Target nucleic acid sequences can be identified by a variety of methods such as SAGE. SAGE is based on several principles. First, a short nucleotide sequence tag (9 to 10 b.p.) contains sufficient information content to uniquely identify a transcript provided it is isolated from a defined position within the transcript. For example, a sequence as short as 9 b.p. can distinguish 262,144 transcripts given a random nucleotide distribution at the tag site, whereas estimates suggest that the human genome encodes about 80,000 to 200,000 transcripts (Fields, et al., *Nature Genetics*, 7:345 1994). The size of the tag can be shorter for lower eukaryotes or prokaryotes, for example, where the number of transcripts encoded by the genome is lower. For example, a tag as short as 6-7 b.p. may be sufficient for distinguishing transcripts in yeast.

Second, random dimerization of tags allows a procedure for reducing bias (caused by amplification and/or cloning). Third, concatenation of these short sequence tags allows the efficient analysis of transcripts in a serial manner by sequencing multiple tags within a single vector or clone. As with serial communication by computers, wherein information is transmitted as a continuous string of data, serial analysis of the sequence tags requires a means to establish the register and boundaries of each tag. The concept of deriving a defined tag from a sequence in accordance with the present invention is useful in matching tags of samples to a sequence database. In the preferred embodiment, a computer method is used to match a sample sequence with known sequences.

The tags used herein, uniquely identify gene products. This is due to their length, and their specific location (3') in a gene from which they are drawn. The full length gene products can be identified by matching the tag to a gene data base member, or by using the tag sequences as probes to physically isolate previously unidentified gene products from cDNA libraries. The methods by which gene products are isolated from libraries using DNA probes are well known in the art. See, for example, Veculescu et al., *Science* 270: 484 (1995), and Sambrook et al. (1989), MOLECULAR CLONING: A LABORATORY MANUAL, 2nd ed. (Cold Spring Harbor Press, Cold Spring Harbor, N.Y.). Once a gene or transcript has been identified, either by matching to a data base entry, or by physically hybridizing to a cDNA molecule, the position of the hybridizing or matching region in the transcript can be determined. If the tag sequence is not in the 3' end, immediately adjacent to the restriction enzyme used to generate the SAGE tags, then a spurious match may have been made. Confirmation of the identity of a SAGE tag can be made by comparing transcription levels of the tag to that of the identified gene in certain cell types.

Analysis of gene expression is not limited to the above methods but can include any method known in the art. All of these principles may be applied independently, in combination, or in combination with other known methods of sequence identification.

Examples of methods of gene expression analysis known in the art include DNA arrays or microarrays (Brazma and Vilo, *FEBS Lett.*, 2000, 480, 17-24; Celis, et al., *FEBS Lett.*, 2000, 480, 2-16), READS (restriction enzyme amplification of digested cDNAs) (Prashar and Weissman, *Methods Enzymol.*, 1999, 303, 258-72), TOGA (total gene expression analysis) (Sutcliffe, et al., *Proc. Natl. Acad. Sci. U.S.A*, 2000, 97, 1976-81), protein arrays and proteomics (Celis, et al., *FEBS Lett.*, 2000, 480, 2-16; Jungblut, et al., *Electrophoresis*, 1999, 20, 2100-10), subtractive RNA fingerprinting (SuRF) (Fuchs, et al., *Anal. Biochem.*, 2000, 286, 91-98; Larson, et al., *Cytometry*, 2000, 41, 203-208), subtractive cloning, differential display (DD) (Jurecic and Belmont, *Curr. Opin. Microbiol.*, 2000, 3, 316-21), comparative genomic hybridization (Carulli, et al., *J. Cell Biochem.* Suppl., 1998, 31, 286-96), FISH (fluorescent in situ hybridization) techniques (Going and Gusterson, *Eur. J. Cancer,*

1999, 35, 1895-904) and mass spectrometry methods (reviewed in (*Comb. Chem. High Throughput Screen,* 2000, 3, 235-41)).

In yet another aspect, siRNA oligonucleotides that selectively bind to variants of target gene expression products are useful for treatment of cancer. For example, p53 mutants are well known in a variety of tumors. A "variant" is an alternative form of a gene. Variants may result from at least one mutation in the nucleic acid sequence and may result in altered mRNAs or in polypeptides whose structure or function may or may not be altered. Any given natural or recombinant gene may have none, one, or many allelic forms. Common mutational changes that give rise to variants are generally ascribed to natural deletions, additions, or substitutions of nucleotides. Each of these types of changes may occur alone, or in combination with the others, one or more times in a given sequence.

Sequence similarity searches can be performed manually or by using several available computer programs known to those skilled in the art. Preferably, Blast and Smith-Waterman algorithms, which are available and known to those skilled in the art, and the like can be used. Blast is NCBI's sequence similarity search tool designed to support analysis of nucleotide and protein sequence databases. Blast can be accessed through the world wide web of the Internet, at, for example, ncbi.nlm.nih.gov/BLAST/. The GCG Package provides a local version of Blast that can be used either with public domain databases or with any locally available searchable database. GCG Package v9.0 is a commercially available software package that contains over 100 interrelated software programs that enables analysis of sequences by editing, mapping, comparing and aligning them. Other programs included in the GCG Package include, for example, programs which facilitate RNA secondary structure predictions, nucleic acid fragment assembly, and evolutionary analysis. In addition, the most prominent genetic databases (GenBank, EMBL, PIR, and SWISS-PROT) are distributed along with the GCG Package and are fully accessible with the database searching and manipulation programs. GCG can be accessed through the Internet at, for example, http://www.gcg.com/. Fetch is a tool available in GCG that can get annotated GenBank records based on accession numbers and is similar to Entrez. Another sequence similarity search can be performed with GeneWorld and GeneThesaurus from Pangea. GeneWorld 2.5 is an automated, flexible, high-throughput application for analysis of polynucleotide and protein sequences. GeneWorld allows for automatic analysis and annotations of sequences. Like GCG, GeneWorld incorporates several tools for homology searching, gene finding, multiple sequence alignment, secondary structure prediction, and motif identification. GeneThesaurus 1.0™ is a sequence and annotation data subscription service providing information from multiple sources, providing a relational data model for public and local data.

Another alternative sequence similarity search can be performed, for example, by BlastParse. BlastParse is a PERL script running on a UNIX platform that automates the strategy described above. BlastParse takes a list of target accession numbers of interest and parses all the GenBank fields into "tab-delimited" text that can then be saved in a "relational database" format for easier search and analysis, which provides flexibility. The end result is a series of completely parsed GenBank records that can be easily sorted, filtered, and queried against, as well as an annotations-relational database.

In accordance with the invention, paralogs can be identified for designing the appropriate siRNA oligonucleotide. Paralogs are genes within a species that occur due to gene duplication, but have evolved new functions, and are also referred to as isotypes.

The polynucleotides of this invention can be isolated using the technique described in the experimental section or replicated using PCR. The PCR technology is the subject matter of U.S. Pat. Nos. 4,683,195, 4,800,159, 4,754,065, and 4,683,202 and described in PCR: The Polymerase Chain Reaction (Mullis et al. eds, Birkhauser Press, Boston (1994)) and references cited therein. Alternatively, one of skill in the art can use the identified sequences and a commercial DNA synthesizer to replicate the DNA. Accordingly, this invention also provides a process for obtaining the polynucleotides of this invention by providing the linear sequence of the polynucleotide, nucleotides, appropriate primer molecules, chemicals such as enzymes and instructions for their replication and chemically replicating or linking the nucleotides in the proper orientation to obtain the polynucleotides. In a separate embodiment, these polynucleotides are further isolated. Still further, one of skill in the art can insert the polynucleotide into a suitable replication vector and insert the vector into a suitable host cell (prokaryotic or eukaryotic) for replication and amplification. The DNA so amplified can be isolated from the cell by methods well known to those of skill in the art. A process for obtaining polynucleotides by this method is further provided herein as well as the polynucleotides so obtained.

Disease Therapy

In another preferred embodiment, the siRNA can be used in treating diseases wherein immune cells are involved in the disease, such as autoimmune disease; hypersensitivity to allergens; organ rejection; inflammation; and the like. Examples of inflammation associated with conditions such as: adult respiratory distress syndrome (ARDS) or multiple organ injury syndromes secondary to septicemia or trauma; reperfusion injury of myocardial or other tissues; acute glomerulonephritis; reactive arthritis; dermatoses with acute inflammatory components; acute purulent meningitis or other central nervous system inflammatory disorders; thermal injury; hemodialysis; leukapheresis; ulcerative colitis; Crohn's disease; necrotizing enterocolitis; granulocyte transfusion associated syndromes; and cytokine-induced toxicity. Examples of autoimmune diseases include, but are not limited to psoriasis, Type I diabetes, Reynaud's syndrome, autoimmune thyroiditis, EAE, multiple sclerosis, rheumatoid arthritis and lupus erythematosus.

The methods of the invention can be used to screen for siRNA polynucleotides that inhibit the functional expression of one or more genes that modulate immune related molecule expression. For example, the CD-18 family of molecules is important in cellular adhesion. Through the process of adhesion, lymphocytes are capable of continually monitoring an animal for the presence of foreign antigens. Although these processes are normally desirable, they are also the cause of organ transplant rejection, tissue graft rejection and many autoimmune diseases. Hence, siRNA's capable of attenuating or inhibiting cellular adhesion would be highly desirable in recipients of organ transplants (for example, kidney transplants), tissue grafts, or for autoimmune patients.

In another preferred embodiment, siRNA oligonucleotides inhibit the expression of MHC molecules involved in organ transplantation or tissue grafting. For example, Class I and Class II molecules of the donor. siRNA inhibit the expression of these molecules thereby ameliorating an allograft reaction. Immune cells may be treated prior to the organ or tissue transplantation, administered at time of transplantation and/or any time thereafter, at times as may be determined by an attending physician. siRNAs can be administered with or without immunosuppressive drug therapy.

In another preferred embodiment, siRNA's are used to treat individuals who are hyper-responsive to an antigen such as an allergic individual. siRNA's are designed to target V region genes known to produce IgE molecules specific for the allergen. IgE antibody specificity can be determined by routine immuno diagnostic techniques such as ELISA's, RIA's, PCR, Western Blots etc. From the amino acid sequence of the IgE molecules, the nucleic acid sequence can be deduced, using any of the database techniques described infra. siRNA's are designed to bind to V region genes or any other part of a gene that makes encodes for the desired antibody, including rearranged and non-rearranged immunoglobulin nucleic acid sequences.

In another preferred embodiment, siRNA's are designed to target suppressor molecules that suppress the expression of gene that is not suppressed in a normal individual. For example, suppressor molecules which inhibit cell-cycle dependent genes, inhibition of p53 mRNA, inhibition of mRNA transcribed by genes coding for cell surface molecules, inhibition of caspases involved in apoptosis and the like.

Apoptosis is important clinically for several reasons. In the field of oncology, many of the clinically useful drugs kill tumor cells by inducing apoptosis. For example, cancer chemotherapeutic agents such as cisplatin, etoposide and taxol all induce apoptosis in target cells. In addition, a variety of pathological disease states can result from the failure of cells to undergo proper regulated apoptosis. For example, the failure to undergo apoptosis can lead to the pathological accumulation of self-reactive lymphocytes such as that occurring in many autoimmune diseases, and can also lead to the accumulation of virally infected cells and to the accumulation of hyperproliferative cells such as neoplastic or tumor cells. siRNA's which target mRNA's from which proteins are translated and are capable of specifically inducing apoptosis would therefore be of therapeutic value in the treatment of these pathological diseases states.

In contrast, the inhibition of apoptosis is also of clinical importance. For example, cells are thought to die by apoptosis in the brain and heart following stroke and myocardial infarction, respectively. Moreover, the inappropriate activation of apoptosis can also contribute to a variety of other pathological disease states including, for example, acquired immunodeficiency syndrome (AIDS), neurodegenerative diseases and ischemic injuries. As apoptotic inducers are of benefit in the previously mentioned disease states, specific inhibitors of apoptosis would similarly be of therapeutic value in the treatment of these latter pathological disease states.

In a preferred embodiment, siRNA's target genes that prevent the normal expression or, if desired, over expression of genes that are of therapeutic interest as described above. As used herein, the term "overexpressing" when used in reference to the level of a gene expression is intended to mean an increased accumulation of the gene product in the overexpressing cells compared to their levels in counterpart normal cells. Overexpression can be achieved by natural biological phenomenon as well as by specific modifications as is the case with genetically engineered cells. Overexpression also includes the achievement of an increase in cell survival polypeptide by either endogenous or exogenous mechanisms. Overexpression by natural phenomenon can result by, for example, a mutation which increases expression, processing, transport, translation or stability of the RNA as well as mutations which result in increased stability or decreased degradation of the polypeptide. Such examples of increased expression levels are also examples of endogenous mechanisms of overexpression. A specific example of a natural biologic phenomenon which results in overexpression by exogenous mechanisms is the adjacent integration of a retrovirus or transposon. Overexpression by specific modification can be achieved by, for example, the use of siRNA oligonucleotides described herein.

An siRNA polynucleotide may be constructed in a number of different ways provided that it is capable of interfering with the expression of a target protein. The siRNA polynucleotide generally will be substantially identical (although in a complementary orientation) to the target molecule sequence. The minimal identity will typically be greater than about 80%, greater than about 90%, greater than about 95% or about 100% identical.

Receptor Modulation and Candidate Therapeutic Agents

In a preferred embodiment, a cell surface receptor is modulated (regulated). Regulation of cellular receptors can be used, for example, in screening of candidate drugs for disease therapy. Using siRNA, we have provided experimental evidence that perturbation of an antisense RNA by siRNA can alter the expression of the corresponding sense messenger RNAs. However, this regulation can either be discordant (antisense knockdown results in sense transcript elevation) or concordant (antisense knockdown results in concomitant sense transcript reduction). Without wishing to be bound by theory, the concepts of regulating genes illustrated in FIGS. 1A-1B and FIGS. 2A-2B. In Table 2 a range of human and mouse antisense transcripts that have been targeted by siRNA are shown. In these cases, two or more siRNAs were targeted to the non-overlapping part of the antisense strand and knockdown was confirmed by use of RT-PCR. Table 2 illustrates the observation that coding as well as non-coding antisense can be targeted in an identical manner and that either category is capable of regulating the corresponding sense transcripts—either in a concordant or disconcordant manner. Here we propose two new potential pharmacological strategies based on the knockdown of antisense RNA transcripts by siRNA (or another RNA targeting principle):

Strategy 1: In the case of discordant regulation, one can by knocking down only the antisense transcript elevate the expression of the conventional (sense) gene. Should that latter gene encode for a known or putative drug target, then knockdown of its antisense counterpart could conceivably mimic the action of a receptor agonist or an enzyme stimulant. Table 2 gives examples where knockdown of antisense (coding as well as non-coding) transcripts was demonstrated to discordantly regulate sense expression. For example, in Parkinson's disease enhanced activity of the mitochondrially localized kinase, PINK', is arguably desirable and knockdown of its non-coding antisense partner might be a means to that end. Further, to stimulate angiogenesis, in certain circumstances, enhanced signaling through the G-protein-coupled receptor (GPCR), CD97, might be achieved by targeting of its (coding) antisense partner, Ddx-39.

An example of strategy I (elevation of PINK1, e.g. Parkinson's disease):

```
PINK-AS:
PINK-AS siRNA-a:
                                (SEQ ID NO: 1)
GGAAGCTGTAGCTAGAACATCTGTT

PINK-AS_siRNA-b:
                                (SEQ ID NO: 2)
CAGGTAAGTAGTCTCCTCTATCATT

PINK-AS_siRNA-c:
                                (SEQ ID NO: 3)
CTCAACCCAAAGCCTGCTTTGTTA
```

Strategy 2: In the case of concordant regulation, one could concomitantly knock down both antisense and sense transcripts and thereby achieve synergistic reduction of the conventional (sense) gene expression. These concepts are illustrated in FIGS. 2A and 2B. If, siRNA is used to achieve knockdown, then this strategy would be further tested by applying one siRNA targeted to the sense transcript and another siRNA to the corresponding antisense transcript, or a single energetically symmetric siRNA that simultaneously targets overlapping sense and antisense transcripts. As follows from Table 2, such dual concomitant targeting, for example, be relevant to pursue in the case of hypoxia-inducible factor 1 alpha, a target whose inhibition may be beneficial in various medical conditions. Another example in Table 2 is the Adrenomedullin AM1 receptor, a GPCR where reduced signaling could also prove to be of therapeutic benefit.

With an emerging functional RNA world, there are new potential drug targets to be considered. Among these are large numbers of natural occurring antisense transcripts with a capacity to regulate the expression of sense transcripts including those that encode for conventional drug targets. Since many of these antisense transcripts represent non-coding RNA, they cannot be manipulated at the protein level. With the use of siRNA we have shown that antisense transcript knockdown can result in either increase (discordant regulation) or decrease (concordant regulation) of sense transcript expression. These findings and concepts may form a basis for novel pharmacological strategies.

In a preferred embodiment, a method of identifying candidate therapeutic agents for treatment of disease, such as, Parkinson's, Alzheimer's, neurological disorders/diseases, tumors and the like, comprises culturing an isolated cell wherein a cellular receptor has been regulated using the methods of the invention, for example, regulation (i.e., up-regulation, or inhibition of expression of a receptor) and, administering a candidate therapeutic agent to the cultured cell; correlating expression levels and phosphorylation of the receptor in the presence or absence of a candidate therapeutic agent as compared to a normal cell and a cell with a regulated receptor, cultured in the presence of a candidate therapeutic agent, wherein a drug is identified based on desirable therapeutic outcomes. For example, a drug which increases expression of a receptor, decreases expression of a receptor, phosphorylates or de-phosphorylates a receptor and the like, thereby, identifying candidate therapeutic agents that regulate receptors.

Another suitable method for diagnosis and candidate drug discovery includes contacting a test sample with a cell expressing a receptor or gene thereof, an allele or fragment thereof; and detecting interaction of the test sample with the gene, an allele or fragment thereof, or expression product of the gene, an allele or fragment thereof. The desired gene, an allele or fragment thereof, or expression product of the gene, an allele or fragment thereof suitably can be detectably labeled e.g. with a fluorescent or radioactive component.

In another preferred embodiment, a cell from a patient is isolated and contacted with a candidate therapeutic molecule. The genes, expression products thereof, are monitored to identify which genes or expression products are regulated by the drug. Interference RNA's can then be synthesized to regulate the identified genes, expression products that are regulated by the drug and thus, provide therapeutic oligonucleotides. These can be tailored to individual patients, which is advantageous as different patients do not effectively respond to the same drugs equally. Thus, the oligonucleotides would provide a cheaper and individualized treatment than conventional drug treatments.

In one aspect, hybridization with oligonucleotide probes that are capable of detecting polynucleotide sequences, including genomic sequences, encoding desired genes or closely related molecules may be used to identify target nucleic acid sequences. The specificity of the probe, whether it is made from a highly specific region, e.g., the 5' regulatory region, or from a less specific region, e.g., a conserved motif, and the stringency of the hybridization or amplification (maximal, high, intermediate, or low), will determine whether the probe identifies only naturally occurring sequences encoding genes, allelic variants, or related sequences.

Probes may also be used for the detection of related sequences, and should preferably have at least 50% sequence identity or homology to any of the identified genes encoding sequences, more preferably at least about 60, 70, 75, 80, 85, 90 or 95 percent sequence identity to any of the identified gene encoding sequences (sequence identity determinations discussed above, including use of BLAST program). The hybridization probes of the subject invention may be DNA or RNA and may be derived from the sequences of the invention or from genomic sequences including promoters, enhancers, and introns of the gene.

"Homologous," as used herein, refers to the subunit sequence similarity between two polymeric molecules, e.g., between two nucleic acid molecules such as two DNA molecules, or two polypeptide molecules. When a subunit position in both of the two molecules is occupied by the same monomeric subunit (e.g., if a position in each of two DNA molecules is occupied by adenine) then they are homologous at that position. The homology between two sequences is a direct function of the number of matching or homologous positions. For example, if 5 of 10 positions in two compound sequences are matched or homologous then the two sequences are 50% homologous, if 9 of 10 are matched or homologous, the two sequences share 90% homology. By way of example, the DNA sequences 3' ATTGCC 5' and 3' TTTCCG 5' share 50% homology.

Means for producing specific hybridization probes for DNAs encoding target genes include the cloning of polynucleotide sequences encoding target genes or derivatives into vectors for the production of mRNA probes. Such vectors are known in the art, are commercially available, and may be used to synthesize RNA probes in vitro by means of the addition of the appropriate RNA polymerases and the appropriate labeled nucleotides. Hybridization probes may be labeled by a variety of reporter groups, for example, by radionuclides such as $^{32}P$ or $^{32}S$, or by enzymatic labels, such as alkaline phosphatase coupled to the probe via avidin-biotin coupling systems, fluorescent labeling, and the like.

The polynucleotide sequences encoding a target gene may be used in Southern or Northern analysis, dot blot, or other membrane-based technologies; in PCR technologies; in dipstick, pin, and multiformat ELISA-like assays; and in microarrays utilizing fluids or tissues from patients to detect altered target gene expression. Gel-based mobility-shift analyses may be employed. Other suitable qualitative or quantitative methods are well known in the art.

Identity of genes, or variants thereof, can be verified using techniques well known in the art. Examples include but are not limited to, nucleic acid sequencing of amplified genes, hybridization techniques such as single nucleic acid polymorphism analysis (SNP), microarrays wherein the molecule of interest is immobilized on a biochip. Overlapping cDNA clones can be sequenced by the dideoxy chain reaction using fluorescent dye terminators and an ABI sequencer (Applied Biosystems, Foster City, Calif.). Any type of assay wherein one component is immobilized may be carried out using the substrate platforms of the invention. Bioassays utilizing an immobilized component are well known in the art. Examples of assays utilizing an immobilized component include for example, immunoassays, analysis of protein-protein interactions, analysis of protein-nucleic acid interactions, analysis of nucleic acid-nucleic acid interactions, receptor binding assays, enzyme assays, phosphorylation assays, diagnostic assays for determination of disease state, genetic profiling for drug compatibility analysis, SNP detection, etc.

Identification of a nucleic acid sequence capable of binding to a biomolecule of interest can be achieved by immobilizing a library of nucleic acids onto the substrate surface so that each unique nucleic acid was located at a defined position to form an array. The array would then be exposed to the biomolecule under conditions which favored binding of the biomolecule to the nucleic acids. Non-specifically binding biomolecules could be washed away using mild to stringent buffer conditions depending on the level of specificity of binding desired. The nucleic acid array would then be analyzed to determine which nucleic acid sequences bound to the biomolecule. Preferably the biomolecules would carry a fluorescent tag for use in detection of the location of the bound nucleic acids.

An assay using an immobilized array of nucleic acid sequences may be used for determining the sequence of an unknown nucleic acid; single nucleotide polymorphism (SNP) analysis; analysis of gene expression patterns from a particular species, tissue, cell type, etc.; gene identification; etc.

Additional diagnostic uses for oligonucleotides designed from the sequences encoding a desired gene expression product may involve the use of PCR. These oligomers may be chemically synthesized, generated enzymatically, or produced in vitro. Oligomers will preferably contain a fragment of a polynucleotide encoding the expression products, or a fragment of a polynucleotide complementary to the polynucleotides, and will be employed under optimized conditions for identification of a specific gene. Oligomers may also be employed under less stringent conditions for detection or quantitation of closely-related DNA or RNA sequences.

In further embodiments, oligonucleotides or longer fragments derived from any of the polynucleotide sequences, may be used as targets in a microarray. The microarray can be used to monitor the identity and/or expression level of large numbers of genes and gene transcripts simultaneously to identify genes with which target genes or its product interacts and/or to assess the efficacy of candidate therapeutic agents in regulating expression products of genes that mediate, for example, neurological disorders. This information may be used to determine gene function, and to develop and monitor the activities of therapeutic agents.

Microarrays may be prepared, used, and analyzed using methods known in the art (see, e.g., Brennan et al., 1995, U.S. Pat. No. 5,474,796; Schena et al., 1996, *Proc. Natl. Acad. Sci. U.S.A.* 93: 10614-10619; Baldeschweiler et al., 1995, PCT application WO95/251116; Shalon, et al., 1995, PCT application WO95/35505; Heller et al., 1997, *Proc. Natl. Acad. Sci. U.S.A.* 94: 2150-2155; and Heller et al., 1997, U.S. Pat. No. 5,605,662).

Candidate agents include numerous chemical classes, though typically they are organic compounds including small organic compounds, nucleic acids including oligonucleotides, and peptides. Small organic compounds suitably may have e.g. a molecular weight of more than about 40 or 50 yet less than about 2,500. Candidate agents may comprise functional chemical groups that interact with proteins and/or DNA.

Candidate agents may be obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of e.g. bacterial, fungal and animal extracts are available or readily produced.

Therapeutic agent assays of the invention suitably include, animal models, cell-based systems and non-cell based systems.

Preferably, identified genes, variants, fragments, or oligopeptides thereof are used for identifying agents of therapeutic interest, e.g. by screening libraries of compounds or otherwise identifying compounds of interest by any of a variety of drug screening or analysis techniques. The gene, allele, fragment, or oligopeptide thereof employed in such screening may be free in solution, affixed to a solid support, borne on a cell surface, or located intracellularly.

Another technique for drug screening provides for high throughput screening of compounds having suitable binding affinity to the protein of interest (see, e.g., Geysen et al., 1984, PCT application WO84/03564). In this method, large numbers of different small test compounds are synthesized on a solid substrate. The test compounds are reacted with identified genes, or fragments thereof, and washed. Bound molecules are then detected by methods well known in the art. Alternatively, non-neutralizing antibodies can be used to capture the peptide and immobilize it on a solid support.

The methods of screening of the invention comprise using screening assays to identify, from a library of diverse molecules, one or more compounds having a desired activity. A "screening assay" is a selective assay designed to identify, isolate, and/or determine the structure of, compounds within a collection that have a preselected activity. By "identifying" it is meant that a compound having a desirable activity is isolated, its chemical structure is determined (including without limitation determining the nucleotide and amino acid sequences of nucleic acids and polypeptides, respectively) the structure of and, additionally or alternatively, purifying compounds having the screened activity). Biochemical and biological assays are designed to test for activity in a broad range of systems ranging from protein-protein interactions, enzyme catalysis, small molecule-protein binding, to cellular functions. Such assays include automated, semi-automated assays and HTS (high throughput screening) assays.

In HTS methods, many discrete compounds are preferably tested in parallel by robotic, automatic or semi-automatic methods so that large numbers of test compounds are screened for a desired activity simultaneously or nearly simultaneously. It is possible to assay and screen up to about 6,000 to 20,000, and even up to about 100,000 to 1,000,000 different compounds a day using the integrated systems of the invention.

Typically in HTS, target molecules are administered or cultured with isolated cells with modulated receptors, including the appropriate controls.

In one embodiment, screening comprises contacting each cell culture with a diverse library of member compounds, some of which are ligands of the target, under conditions where complexes between the target and ligands can form, and identifying which members of the libraries are present in such complexes. In another non limiting modality, screening comprises contacting a target enzyme with a diverse library of member compounds, some of which are inhibitors (or activators) of the target, under conditions where a product or a reactant of the reaction catalyzed by the enzyme produce a detectable signal. In the latter modality, inhibitors of target enzyme decrease the signal from a detectable product or increase a signal from a detectable reactant (or vice-versa for activators).

Chemical Libraries: Developments in combinatorial chemistry allow the rapid and economical synthesis of hundreds to thousands of discrete compounds. These compounds are typically arrayed in moderate-sized libraries of small molecules designed for efficient screening. Combinatorial methods, can be used to generate unbiased libraries suitable for the identification of novel compounds. In addition, smaller, less diverse libraries can be generated that are descended from a single parent compound with a previously determined biological activity. In either case, the lack of efficient screening systems to specifically target therapeutically relevant biological molecules produced by combinational chemistry such as inhibitors of important enzymes hampers the optimal use of these resources.

A combinatorial chemical library is a collection of diverse chemical compounds generated by either chemical synthesis or biological synthesis, by combining a number of chemical "building blocks," such as reagents. For example, a linear combinatorial chemical library, such as a polypeptide library, is formed by combining a set of chemical building blocks (amino acids) in a large number of combinations, and potentially in every possible way, for a given compound length (i.e., the number of amino acids in a polypeptide compound). Millions of chemical compounds can be synthesized through such combinatorial mixing of chemical building blocks.

A "library" may comprise from 2 to 50,000,000 diverse member compounds. Preferably, a library comprises at least 48 diverse compounds, preferably 96 or more diverse compounds, more preferably 384 or more diverse compounds, more preferably, 10,000 or more diverse compounds, preferably more than 100,000 diverse members and most preferably more than 1,000,000 diverse member compounds. By "diverse" it is meant that greater than 50% of the compounds in a library have chemical structures that are not identical to any other member of the library. Preferably, greater than 75% of the compounds in a library have chemical structures that are not identical to any other member of the collection, more preferably greater than 90% and most preferably greater than about 99%.

The preparation of combinatorial chemical libraries is well known to those of skill in the art. For reviews, see Thompson et al., Synthesis and application of small molecule libraries, *Chem Rev* 96:555-600, 1996; Kenan et al., Exploring molecular diversity with combinatorial shape libraries, *Trends Biochem Sci* 19:57-64, 1994; Janda, Tagged versus untagged libraries: methods for the generation and screening of combinatorial chemical libraries, *Proc Natl Acad Sci USA.* 91:10779-85, 1994; Lebl et al., One-bead-one-structure combinatorial libraries, *Biopolymers* 37:177-98, 1995; Eichler et al., Peptide, peptidomimetic, and organic synthetic combinatorial libraries, *Med Res Rev.* 15:481-96, 1995; Chabala, Solid-phase combinatorial chemistry and novel tagging methods for identifying leads, *Curr Opin Biotechnol.* 6:632-9, 1995; Dolle, Discovery of enzyme inhibitors through combinatorial chemistry, *Mol Divers.* 2:223-36, 1997; Fauchere et al., Peptide and non-peptide lead discovery using robotically synthesized soluble libraries, Can J. Physiol Pharmacol. 75:683-9, 1997; Eichler et al., Generation and utilization of synthetic combinatorial libraries, *Mol Med Today* 1: 174-80, 1995; and Kay et al., Identification of enzyme inhibitors from phage-displayed combinatorial peptide libraries, *Comb Chem High Throughput Screen* 4:535-43, 2001.

Other chemistries for generating chemical diversity libraries can also be used. Such chemistries include, but are not limited to, peptoids (PCT Publication No. WO 91/19735); encoded peptides (PCT Publication WO 93/20242); random bio-oligomers (PCT Publication No. WO 92/00091); benzodiazepines (U.S. Pat. No. 5,288,514); diversomers, such as hydantoins, benzodiazepines and dipeptides (Hobbs, et al., *Proc. Nat. Acad. Sci. USA,* 90:6909-6913 (1993)); vinylogous polypeptides (Hagihara, et al., *J. Amer. Chem. Soc.* 114:6568 (1992)); nonpeptidal peptidomimetics with .beta.-D-glucose scaffolding (Hirschmann, et al., *J. Amer. Chem. Soc.,* 114:9217-9218 (1992)); analogous organic syntheses of small compound libraries (Chen, et al., *J. Amer. Chem. Soc.,* 116:2661 (1994)); oligocarbamates (Cho, et al., *Science,* 261:1303 (1993)); and/or peptidyl phosphonates (Campbell, et al., *J. Org. Chem.* 59:658 (1994)); nucleic acid libraries (see, Ausubel, Berger and Sambrook, all supra); peptide nucleic acid libraries (see, e.g., U.S. Pat. No. 5,539,083); antibody libraries (see, e.g., Vaughn, et al., *Nature Biotechnology,* 14(3):309-314 (1996) and PCT/US96/10287); carbohydrate libraries (see, e.g., Liang, et al., *Science,* 274:1520-1522 (1996) and U.S. Pat. No. 5,593,853); small organic molecule libraries (see, e.g., benzodiazepines, Baum C&E News, January 18, page 33 (1993); isoprenoids (U.S. Pat. No. 5,569,588); thiazolidinones and metathiazanones (U.S. Pat. No. 5,549,974); pyrrolidines (U.S. Pat. Nos. 5,525,735 and 5,519,134); morpholino compounds (U.S. Pat. No. 5,506,337); benzodiazepines (U.S. Pat. No. 5,288,514); and the like.

Devices for the preparation of combinatorial libraries are commercially available (see, e.g., 357 MPS, 390 MPS, Advanced Chem. Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Asinex, Moscow, Ru, Tripos, Inc., St. Louis, Mo., Chem-Star, Ltd., Moscow, RU, 3D Pharmaceuticals, Exton, Pa., Martek Bio sciences, Columbia, Md., etc.).

High throughput screening can be used to measure the effects of drugs on complex molecular events such as signal transduction pathways, as well as cell functions including, but not limited to, cell function, apoptosis, cell division, cell adhesion, locomotion, exocytosis, and cell-cell communication. Multicolor fluorescence permits multiple targets and cell processes to be assayed in a single screen. Cross-correlation of cellular responses will yield a wealth of information required for target validation and lead optimization.

In another aspect, the present invention provides a method for analyzing cells comprising providing an array of locations which contain multiple cells wherein the cells contain one or more fluorescent reporter molecules; scanning multiple cells in each of the locations containing cells to obtain fluorescent signals from the fluorescent reporter molecule in the cells; converting the fluorescent signals into digital data; and utilizing the digital data to determine the distribution, environment or activity of the fluorescent reporter molecule within the cells.

A major component of the new drug discovery paradigm is a continually growing family of fluorescent and luminescent reagents that are used to measure the temporal and spatial distribution, content, and activity of intracellular ions, metabolites, macromolecules, and organelles. Classes of these reagents include labeling reagents that measure the distribution and amount of molecules in living and fixed cells, environmental indicators to report signal transduction events in time and space, and fluorescent protein biosensors to measure target molecular activities within living cells. A multiparameter approach that combines several reagents in a single cell is a powerful new tool for drug discovery.

This method relies on the high affinity of fluorescent or luminescent molecules for specific cellular components. The affinity for specific components is governed by physical forces such as ionic interactions, covalent bonding (which includes chimeric fusion with protein-based chromophores, fluorophores, and lumiphores), as well as hydrophobic interactions, electrical potential, and, in some cases, simple entrapment within a cellular component. The luminescent probes can be small molecules, labeled macromolecules, or genetically engineered proteins, including, but not limited to green fluorescent protein chimeras.

Those skilled in this art will recognize a wide variety of fluorescent reporter molecules that can be used in the present invention, including, but not limited to, fluorescently labeled biomolecules such as proteins, phospholipids, RNA and DNA hybridizing probes. Similarly, fluorescent reagents specifically synthesized with particular chemical properties of binding or association have been used as fluorescent reporter molecules (Barak et al., (1997), *J. Biol. Chem.* 272:27497-27500; Southwick et al., (1990), *Cytometry* 11:418-430; Tsien (1989) in *Methods in Cell Biology*, Vol. 29 Taylor and Wang (eds.), pp. 127-156). Fluorescently labeled antibodies are particularly useful reporter molecules due to their high degree of specificity for attaching to a single molecular target in a mixture of molecules as complex as a cell or tissue.

The luminescent probes can be synthesized within the living cell or can be transported into the cell via several non-mechanical modes including diffusion, facilitated or active transport, signal-sequence-mediated transport, and endocytotic or pinocytotic uptake. Mechanical bulk loading methods, which are well known in the art, can also be used to load luminescent probes into living cells (Barber et al. (1996), *Neuroscience Letters* 207:17-20; Bright et al. (1996), *Cytometry* 24:226-233; McNeil (1989) in *Methods in Cell Biology*, Vol. 29, Taylor and Wang (eds.), pp. 153-173). These methods include electroporation and other mechanical methods such as scrape-loading, bead-loading, impact-loading, syringe-loading, hypertonic and hypotonic loading. Additionally, cells can be genetically engineered to express reporter molecules, such as GFP, coupled to a protein of interest as previously described (Chalfie and Prasher U.S. Pat. No. 5,491,084; Cubitt et al. (1995), *Trends in Biochemical Science* 20:448-455).

Once in the cell, the luminescent probes accumulate at their target domain as a result of specific and high affinity interactions with the target domain or other modes of molecular targeting such as signal-sequence-mediated transport. Fluorescently labeled reporter molecules are useful for determining the location, amount and chemical environment of the reporter. For example, whether the reporter is in a lipophilic membrane environment or in a more aqueous environment can be determined (Giuliano et al. (1995), *Ann. Rev. of Biophysics and Biomolecular Structure* 24:405-434; Giuliano and Taylor (1995), *Methods in Neuroscience* 27.1-16). The pH environment of the reporter can be determined (Bright et al. (1989), *J. Cell Biology* 104:1019-1033; Giuliano et al. (1987), *Anal. Biochem.* 167:362-371; Thomas et al. (1979), *Biochemistry* 18:2210-2218). It can be determined whether a reporter having a chelating group is bound to an ion, such as $Ca^{++}$, or not (Bright et al. (1989), *In Methods in Cell Biology*, Vol. 30, Taylor and Wang (eds.), pp. 157-192; Shimoura et al. (1988), *J. of Biochemistry* (Tokyo) 251:405-410; Tsien (1989) In *Methods in Cell Biology*, Vol. 30, Taylor and Wang (eds.), pp. 127-156).

Furthermore, certain cell types within an organism may contain components that can be specifically labeled that may not occur in other cell types. For example, neural cells often contain polarized membrane components. That is, these cells asymmetrically distribute macromolecules along their plasma membrane. Connective or supporting tissue cells often contain granules in which are trapped molecules specific to that cell type (e.g., heparin, histamine, serotonin, etc.). Most muscular tissue cells contain a sarcoplasmic reticulum, a specialized organelle whose function is to regulate the concentration of calcium ions within the cell cytoplasm. Many nervous tissue cells contain secretory granules and vesicles in which are trapped neurohormones or neurotransmitters. Therefore, fluorescent molecules can be designed to label not only specific components within specific cells, but also specific cells within a population of mixed cell types.

Those skilled in the art will recognize a wide variety of ways to measure fluorescence. For example, some fluorescent reporter molecules exhibit a change in excitation or emission spectra, some exhibit resonance energy transfer where one fluorescent reporter loses fluorescence, while a second gains in fluorescence, some exhibit a loss (quenching) or appearance of fluorescence, while some report rotational movements (Giuliano et al. (1995), *Ann. Rev. of Biophysics and Biomol. Structure* 24:405-434; Giuliano et al. (1995), *Methods in Neuroscience* 27:1-16).

The whole procedure can be fully automated. For example, sampling of sample materials may be accomplished with a plurality of steps, which include withdrawing a sample from a sample container and delivering at least a portion of the withdrawn sample to test cell culture (e.g., a cell culture wherein gene expression is regulated). Sampling may also include additional steps, particularly and preferably, sample preparation steps. In one approach, only one sample is withdrawn into the auto-sampler probe at a time and only one sample resides in the probe at one time. In other embodiments, multiple samples may be drawn into the auto-sampler probe separated by solvents. In still other embodiments, multiple probes may be used in parallel for auto sampling.

In the general case, sampling can be effected manually, in a semi-automatic manner or in an automatic manner. A sample can be withdrawn from a sample container manually, for example, with a pipette or with a syringe-type manual probe, and then manually delivered to a loading port or an injection port of a characterization system. In a semi-automatic protocol, some aspect of the protocol is effected automatically (e.g., delivery), but some other aspect requires manual intervention (e.g., withdrawal of samples from a process control line). Preferably, however, the sample(s) are withdrawn from a sample container and delivered to the characterization system, in a fully automated manner—for example, with an auto-sampler.

In one embodiment, auto-sampling may be done using a microprocessor controlling an automated system (e.g., a robot arm). Preferably, the microprocessor is user-programmable to accommodate libraries of samples having varying arrangements of samples (e.g., square arrays with "n-rows" by "n-columns," rectangular arrays with "n-rows" by "m-columns," round arrays, triangular arrays with "r-" by "r-" by "r-" equilateral sides, triangular arrays with "r-base" by "s-" by "s-" isosceles sides, etc., where n, m, r, and s are integers).

Automated sampling of sample materials optionally may be effected with an auto-sampler having a heated injection probe (tip). An example of one such auto sampler is disclosed in U.S. Pat. No. 6,175,409 B1 (incorporated by reference).

According to the present invention, one or more systems, methods or both are used to identify a plurality of sample materials. Though manual or semi-automated systems and methods are possible, preferably an automated system or method is employed. A variety of robotic or automatic systems are available for automatically or programmably providing predetermined motions for handling, contacting, dispensing, or otherwise manipulating materials in solid, fluid liquid or gas form according to a predetermined protocol. Such systems may be adapted or augmented to include a variety of hardware, software or both to assist the systems in determining mechanical properties of materials. Hardware and software for augmenting the robotic systems may include, but are not limited to, sensors, transducers, data acquisition and manipulation hardware, data acquisition and manipulation software and the like. Exemplary robotic systems are commercially available from CAVRO Scientific Instruments (e.g., Model NO. RSP9652) or BioDot (Microdrop Model 3000).

Generally, the automated system includes a suitable protocol design and execution software that can be programmed with information such as synthesis, composition, location information or other information related to a library of materials positioned with respect to a substrate. The protocol design and execution software is typically in communication with robot control software for controlling a robot or other automated apparatus or system. The protocol design and execution software is also in communication with data acquisition hardware/software for collecting data from response measuring hardware. Once the data is collected in the database, analytical software may be used to analyze the data, and more specifically, to determine properties of the candidate drugs, or the data may be analyzed manually.

In another preferred embodiment, the assaying of the candidate drugs or samples with the cell culture is combined with one or more methods. In one embodiment, a sample can be pre-fractionated according to size of proteins in a sample using size exclusion chromatography. For a biological sample wherein the amount of sample available is small, preferably a size selection spin column is used. In general, the first fraction that is eluted from the column ("fraction 1") has the highest percentage of high molecular weight proteins; fraction 2 has a lower percentage of high molecular weight proteins; fraction 3 has even a lower percentage of high molecular weight proteins; fraction 4 has the lowest amount of large proteins; and so on. Each fraction can then be analyzed by immunoassays, gas phase ion spectrometry, and the like, for the detection of compounds.

In another embodiment, a sample can be pre-fractionated by anion exchange chromatography. Anion exchange chromatography allows pre-fractionation of the proteins in a sample roughly according to their charge characteristics. For example, a Q anion-exchange resin can be used (e.g., Q HyperD F, Biosepra), and a sample can be sequentially eluted with eluants having different pH's. Anion exchange chromatography allows separation of compounds in a sample that are more negatively charged from other types of compounds. Proteins that are eluted with an eluant having a high pH is likely to be weakly negatively charged, and a fraction that is eluted with an eluant having a low pH is likely to be strongly negatively charged. Thus, in addition to reducing complexity of a sample, anion exchange chromatography separates proteins according to their binding characteristics.

In yet another embodiment, a sample can be pre-fractionated by heparin chromatography. Heparin chromatography allows pre-fractionation of the compounds in a sample also on the basis of affinity interaction with heparin and charge characteristics. Heparin, a sulfated mucopolysaccharide, will bind compounds with positively charged moieties and a sample can be sequentially eluted with eluants having different pH's or salt concentrations. Samples eluted with an eluant having a low pH are more likely to be weakly positively charged. Samples eluted with an eluant having a high pH are more likely to be strongly positively charged. Thus, heparin chromatography also reduces the complexity of a sample and separates samples according to their binding characteristics.

In yet another embodiment, a sample can be pre-fractionated by isolating proteins that have a specific characteristic, e.g. are glycosylated. For example, a CSF sample can be fractionated by passing the sample over a lectin chromatography column (which has a high affinity for sugars). Glycosylated proteins will bind to the lectin column and non-glycosylated proteins will pass through the flow through. Glycosylated proteins are then eluted from the lectin column with an eluant containing a sugar, e.g., N-acetyl-glucosamine and are available for further analysis.

Thus there are many ways to reduce the complexity of a sample based on the binding properties of the proteins in the sample, or the characteristics of the proteins in the sample.

Delivery of siRNA

Preferred invention practice involves administering at least one of the foregoing siRNA polynucleotides with a suitable nucleic acid delivery system. In one embodiment, that system includes a non-viral vector operably linked to the polynucleotide. Examples of such non-viral vectors include the polynucleoside alone or in combination with a suitable protein, polysaccharide or lipid formulation.

Additionally suitable nucleic acid delivery systems include viral vector, typically sequence from at least one of an adenovirus, adenovirus-associated virus (AAV), helper-dependent adenovirus, retrovirus, or hemagglutinating virus of Japan-liposome (HVJ) complex. Preferably, the viral vector comprises a strong eukaryotic promoter operably linked to the polynucleotide e.g., a cytomegalovirus (CMV) promoter.

Additionally preferred vectors include viral vectors, fusion proteins and chemical conjugates. Retroviral vectors include moloney murine leukemia viruses and HIV-based viruses. One preferred HIV-based viral vector comprises at least two vectors wherein the gag and pol genes are from an HIV genome and the env gene is from another virus. DNA viral vectors are preferred. These vectors include pox vectors such as orthopox or avipox vectors, herpesvirus vectors such as a herpes simplex I virus (HSV) vector [Geller, A. I. et al., *J. Neurochem,* 64: 487 (1995); Lim, F., et al., in DNA Cloning: Mammalian Systems, D. Glover, Ed. (Oxford Univ. Press, Oxford England) (1995); Geller, A. I. et al., *Proc Natl. Acad. Sci.:* U.S.A.:90 7603 (1993); Geller, A. I., et al., *Proc Natl. Acad. Sci USA:* 87:1149 (1990)], Adenovirus Vectors [LeGal LaSalle et al., *Science,* 259:988 (1993); Davidson, et al., *Nat. Genet.* 3: 219 (1993); Yang, et al., *J. Virol.* 69: 2004 (1995)] and Adeno-associated Virus Vectors [Kaplitt, M. G., et al., *Nat. Genet.* 8:148 (1994)].

Pox viral vectors introduce the gene into the cells cytoplasm. Avipox virus vectors result in only a short term expression of the nucleic acid. Adenovirus vectors, adeno-associated virus vectors and herpes simplex virus (HSV) vectors may be an indication for some invention embodiments. The adenovirus vector results in a shorter term expression (e.g., less than about a month) than adeno-associated virus, in some embodiments, may exhibit much longer expression. The particular vector chosen will depend upon the target cell and the condition being treated. The selection of appropriate promoters can readily be accomplished. Preferably, one would use a high expression promoter. An example of a suitable promoter is the 763-base-pair cytomegalovirus (CMV) promoter. The Rous sarcoma virus (RSV) (Davis, et al., *Hum Gene Ther* 4:151 (1993)) and MMT promoters may also be used. Certain proteins can expressed using their native promoter. Other elements that can enhance expression can also be included such as an enhancer or a system that results in high levels of expression such as a tat gene and tar element. This cassette can then be inserted into a vector, e.g., a plasmid vector such as, pUC19, pUC118, pBR322, or other known plasmid vectors, that includes, for example, an *E. coli* origin of replication. See, Sambrook, et al., Molecular Cloning: A Laboratory Manual, Cold Spring Harbor Laboratory press, (1989). The plasmid vector may also include a selectable marker such as the β-lactamase gene for ampicillin resistance, provided that the marker polypeptide does not adversely effect the metabolism of the organism being treated. The cassette can also be bound to a nucleic acid binding moiety in a synthetic delivery system, such as the system disclosed in WO 95/22618.

If desired, the polynucleotides of the invention may also be used with a microdelivery vehicle such as cationic liposomes and adenoviral vectors. For a review of the procedures for liposome preparation, targeting and delivery of contents, see Mannino and Gould-Fogerite, *BioTechniques,* 6:682 (1988). See also, Felgner and Holm, Bethesda Res. Lab. Focus, 11(2):21 (1989) and Maurer, R. A., Bethesda Res. Lab. Focus, 11(2):25 (1989).

Replication-defective recombinant adenoviral vectors, can be produced in accordance with known techniques. See, Quantin, et al., *Proc. Natl. Acad. Sci. USA,* 89:2581-2584 (1992); Stratford-Perricadet, et al., J. Clin. Invest., 90:626-630 (1992); and Rosenfeld, et al., Cell, 68:143-155 (1992).

Another preferred siRNA delivery method is to use single stranded DNA producing vectors which can produce the siRNA's intracellularly. See for example, Chen et al, *BioTechniques,* 34: 167-171 (2003), which is incorporated herein, by reference, in its entirety.

The effective dose of the nucleic acid will be a function of the particular expressed protein, the particular cardiac arrhythmia to be targeted, the patient and his or her clinical condition, weight, age, sex, etc.

One preferred delivery system is a recombinant viral vector that incorporates one or more of the polynucleotides therein, preferably about one polynucleotide. Preferably, the viral vector used in the invention methods has a pfu (plague forming units) of from about $10^8$ to about $5 \times 10^{10}$ pfu. In embodiments in which the polynucleotide is to be administered with a non-viral vector, use of between from about 0.1 nanograms to about 4000 micrograms will often be useful e.g., about 1 nanogram to about 100 micrograms.

Assessing Up-Regulation or Inhibition of Gene Expression

Transfer of an exogenous nucleic acid into a host cell or organism by a vector can be assessed by directly detecting the presence of the nucleic acid in the cell or organism. Such detection can be achieved by several methods well known in the art. For example, the presence of the exogenous nucleic acid can be detected by Southern blot or by a polymerase chain reaction (PCR) technique using primers that specifically amplify nucleotide sequences associated with the nucleic acid. Expression of the exogenous nucleic acids can also be measured using conventional methods. For instance, mRNA produced from an exogenous nucleic acid can be detected and quantified using a Northern blot and reverse transcription PCR (RT-PCR).

Expression of an RNA from the exogenous nucleic acid can also be detected by measuring an enzymatic activity or a reporter protein activity. For example, siRNA activity can be measured indirectly as a decrease or increase in target nucleic acid expression as an indication that the exogenous nucleic acid is producing the effector RNA. Based on sequence conservation, primers can be designed and used to amplify coding regions of the target genes. Initially, the most highly expressed coding region from each gene can be used to build a model control gene, although any coding or non coding region can be used. Each control gene is assembled by inserting each coding region between a reporter coding region and its poly(A) signal. These plasmids would produce an mRNA with a reporter gene in the upstream portion of the gene and a potential RNAi target in the 3' non-coding region. The effectiveness of individual RNAi's would be assayed by modulation of the reporter gene. Reporter genes useful in the methods of the present invention include acetohydroxyacid synthase (AHAS), alkaline phosphatase (AP), beta galactosidase (LacZ), beta glucoronidase (GUS), chloramphenicol acetyltransferase (CAT), green fluorescent protein (GFP), red fluorescent protein (RFP), yellow fluorescent protein (YFP), cyan fluorescent protein (CFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentamycin, hygromycin, kanamycin, lincomycin, methotrexate, phosphinothricin, puromycin, and tetracycline. Methods to determine modulation of a reporter gene are well known in the art, and include, but are not limited to, fluorometric methods (e.g. fluorescence spectroscopy, Fluorescence Activated Cell Sorting (FACS), fluorescence microscopy), antibiotic resistance determination.

Although biogenomic information and model genes are invaluable for high-throughput screening of potential RNAi's, interference activity against target nucleic acids ultimately must be established experimentally in cells which express the target nucleic acid. To determine the interference capability of the RNAi sequence, the RNAi containing vector is transfected into appropriate cell lines which express that target nucleic acid. Each selected RNAi construct is tested for its ability to modulate steady-state mRNA of the target nucleic acid. In addition, any target mRNAs that "survive" the first round of testing are amplified by reverse transcriptase-PCR and sequenced (see, for example, Sambrook, J. et al. "Molecular Cloning: A Laboratory Manual," 2nd addition, Cold Spring Harbor Laboratory Press, Plainview, N.Y. (1989)). These sequences are analyzed to determine individual polymorphisms that allow mRNA to escape the current library of RNAi's. This information is used to further modify RNAi constructs to also target rarer polymorphisms.

Methods by which to transfect cells with RNAi vectors are well known in the art and include, but are not limited to, electroporation, particle bombardment, microinjection, transfection with viral vectors, transfection with retrovirus-based vectors, and liposome-mediated transfection. Any of the types of nucleic acids that mediate RNA interference can be synthesized in vitro using a variety of methods well known in the art and inserted directly into a cell. In addition, dsRNA and other molecules that mediate RNA interference are available from commercial vendors, such as Ribopharma AG (Kulmach, Germany), Eurogentec (Seraing, Belgium), Sequitur (Natick, Mass.) and Invitrogen (Carlsbad, Calif.). Eurogentec offers dsRNA that has been labeled with fluorophores (e.g., HEX/TET; 5'-Fluorescein, 6-FAM; 3'-Fluorescein, 6-FAM; Fluorescein dT internal; 5' TAMRA, Rhodamine; 3' TAMRA, Rhodamine), which can also be used in the invention. RNAi molecules can be made through the well-known technique of solid-phase synthesis. Equipment for such synthesis is sold by several vendors including, for example, Applied Biosystems (Foster City, Calif.). Other methods for such synthesis that are known in the art can additionally or alternatively be employed. It is well-known to use similar techniques to prepare oligonucleotides such as the phosphorothioates and alkylated derivatives.

RNA directly inserted into a cell can include modifications to either the phosphate-sugar backbone or the nucleoside. For example, the phosphodiester linkages of natural RNA can be modified to include at least one of a nitrogen or sulfur heteroatom. The interfering RNA can be produced enzymatically or by partial/total organic synthesis. The constructs can be synthesized by a cellular RNA polymerase or a bacteriophage RNA polymerase (e.g., T3, T7, SP6). If synthesized chemically or by in vitro enzymatic synthesis, the RNA can be purified prior to introduction into a cell or animal. For example, RNA can be purified from a mixture by extraction with a solvent or resin, precipitation, electrophoresis, chromatography or a combination thereof as known in the art. Alternatively, the interfering RNA construct can be used without, or with a minimum of purification to avoid losses due to sample processing. The RNAi construct can be dried for storage or dissolved in an aqueous solution. The solution can contain buffers or salts to promote annealing, and/or stabilization of the duplex strands. Examples of buffers or salts that can be used in the present invention include, but are not limited to, saline, PBS, N-(2-Hydroxyethyl)piperazin-e-N'-(2-ethanesulfonic acid) (HEPES™), 3-(N-Morpholino)propanesulfonic acid (MOPS), 2-bis(2-Hydroxyethylene)amino-2-(hydroxymethyl)-1,3-propanediol (bis-TRIS™), potassium phosphate (KP), sodium phosphate (NaP), dibasic sodium phosphate ($Na_2HPO_4$), monobasic sodium phosphate ($NaH_2PO_4$), monobasic sodium potassium phosphate ($NaKHPO_4$), magnesium phosphate ($Mg_3(PO_4)_2 \cdot 4H_2O$), potassium acetate ($CH_3COOH$), D(+)-α-sodium glycerophosphate ($HOCH_2CH(OH)CH_2OPO_3Na_2$) and other physiologic buffers known to those skilled in the art. Additional buffers for use in the invention include, a salt M-X dissolved in aqueous solution, association, or dissociation products thereof, where M is an alkali metal (e.g., $Li^+$, $Na^+$, $K^+$, $Rb^+$), suitably sodium or potassium, and where X is an anion selected from the group consisting of phosphate, acetate, bicarbonate, sulfate, pyruvate, and an organic monophosphate ester, glucose 6-phosphate or DL-α-glycerol phosphate.

Genes Regulated/Targeted by RNAi Molecules.

In a further aspect of the present invention, RNAi molecules that regulate the expression of specific genes or family of genes are provided, such that the expression of the genes can be functionally eliminated or up-regulated. In one embodiment, at least two RNAi molecules are provided that target the same region of a gene. In another embodiment, at least two RNAi molecules are provided that target at least two different regions of the same gene. In a further embodiment, at least two RNAi molecules are provided that target at least two different genes. Additional embodiments of the invention provide combinations of the above strategies for gene targeting.

In one embodiment, the RNAi molecules can be the same sequence. In an alternate embodiment, the RNAi molecules can be different sequences. In other embodiments, at least two RNAi molecules are provided wherein the families of one or more genes can be regulated by expression of the RNAi molecules. In another embodiment, at least three, four or five RNAi molecules are provided wherein the families of one or more genes can be regulated by expression of the RNAi molecules. The RNAi molecule can be homologous to a conserved sequence within one or more genes. The family of genes regulated using such methods of the invention can be endogenous to a cell, a family of related viral genes, a family of genes that are conserved within a viral genus, a family of related eukaryotic parasite genes, or more particularly a family of genes from a porcine endogenous retrovirus. In one specific embodiment, at least two RNAi molecules can target the at least two different genes, which are members of the same family of genes. The RNAi molecules can target homologous regions within a family of genes and thus one RNAi molecule can target the same region of multiple genes.

The RNAi molecule can be selected from, but not limited to the following types of RNAi: antisense oligonucleotides, ribozymes, small interfering RNAs (sRNAis), double stranded RNAs (dsRNAs), inverted repeats, short hairpin RNAs (shRNAs), small temporally regulated RNAs, and clustered inhibitory RNAs (cRNAis), including radial clustered inhibitory RNA, asymmetric clustered inhibitory RNA, linear clustered inhibitory RNA, and complex or compound clustered inhibitory RNA.

In another embodiment, expression of RNAi molecules for regulating target genes in mammalian cell lines or transgenic animals is provided such that expression of the target gene is functionally eliminated or below detectable levels or up-regulated, i.e. the expression of the target gene is decreased or increased by at least about 70%, 75%, 80%, 85%, 90%, 95%, 97% or 99%.

In another embodiment of this aspect of the present invention, methods are provided to produce cells and animals in which interfering RNA molecules are expressed to regulate the expression of target genes. Methods according to this aspect of the invention can comprise, for example: identifying one or more target nucleic acid sequences in a cell; obtaining at least one RNAi molecule that bind to the target nucleic acid sequence(s); introducing the RNAi molecules, optionally packaged in an expression vector, into the cell; and expressing the RNAi's in the cell under conditions such that the RNAi's bind to the target nucleic acid sequences, thereby regulating expression of one or more target genes.

In embodiments of the present invention, endogenous genes that can be regulated by the expression of at least one RNAi molecule include, but are not limited to, genes required for cell survival or cell replication, genes required for viral replication, genes that encode an immunoglobulin locus, for example, Kappa light chain, and genes that encode a cell surface protein, for example, Vascular Cell Adhesion Molecule (VCAM) and other genes important to the structure and/or function of cells, tissues, organs and animals. The methods of the invention can also be used to regulate the expression of one or more non-coding RNA sequences. These non-coding RNA sequences can be sequences of an RNA virus genome, an endogenous gene, a eukaryotic parasite gene, or other non-coding RNA sequences that are known in the art and that will be familiar to the ordinarily skilled artisan. RNAi molecules that are expressed in cells or animals according to the aspects of the present invention can decrease, increase or maintain expression of one or more target genes. In order to identify specific target nucleic acid regions in which the expression of one or more genes, family of genes, desired subset of genes, or alleles of a gene is to be regulated, a representative sample of sequences for each target gene can be obtained. Sequences can be compared to find similar and dissimilar regions. This analysis can determine regions of identity between all family members and within subsets (i.e. groups within the gene family) of family members. In addition, this analysis can determines region of identity between alleles of each family member. By considering regions of identity between alleles of family members, between subsets of family members, and across the entire family, target regions can be identified that specify the entire family, subsets of family members, individual family members, subsets of alleles of individual family members, or individual alleles of family members.

Regulation of expression can decrease expression of one or more target genes. Decreased expression results in post-transcriptional down-regulation of the target gene and ultimately the final product protein of the target gene. For down-regulation, the target nucleic acid sequences are identified such that binding of the RNAi to the sequence will decrease expression of the target gene. Decreased expression of a gene refers to the absence of, or observable or detectable decrease in, the level of protein and/or mRNA product from a target gene relative to that without the introduction of the RNAi. Complete suppression/inhibition as well as partial suppressed expression of the target gene are possible with the methods of the present invention. By "partial suppressed expression," it is meant that the target gene is suppressed (i.e. the expression of the target gene is reduced) from about 10% to about 99%, with 100% being complete suppression/inhibition of the target gene. For example, about 10%, about 20%, about 30%, about 40%, about 50%, about 60%, about 70%, about 80%, about 90%, about 95%, or about 99% of gene expression of the one or more genes can be suppressed. Alternatively, expression is suppressed or inhibited below detectable threshold limits.

In other embodiments of the invention, regulation of expression can increase expression of one or more genes. Increased expression can result as discussed in detail in the examples which follow. In this embodiment of the invention, the target nucleic acid and the gene of interest can be separate sequences. Increased expression of a gene refers to the presence, or observable increase, in the level of protein and/or mRNA product from one or more target genes relative to that without the introduction of the RNAi. By increased expression of a gene, it is meant that the measurable amount of the target gene that is expressed is increased any amount relative to that without the introduction of the RNAi. For example, the level of expression of the gene can be increased about two-fold, about five-fold, about 10-fold, about 50-fold, about 100-fold, about 500-fold, about 1000-fold, or about 2000-fold, above that which occurs in the absence of the interfering RNA.

In still other aspects of the invention, regulation of expression can maintain expression of one or more genes, when the one or more genes are placed under environmental conditions that generally lead to increased or decreased expression of the one or more genes. Expression of one or more genes can be maintained under environmental conditions that would normally increase or decrease gene expression results in a steady-state level (i.e. no increase or decrease in expression with time) of gene expression relative to expression prior to the presence of environmental conditions that would otherwise increase or decrease expression. Examples of environmental conditions that can increase gene expression include, but are not limited to, the presence of growth factors, increased glucose production, hyperthermia and cell cycle changes. Examples of environmental conditions that can decrease gene expression include, but are not limited to, hypoxia, hypothermia, lack of growth factors and glucose depletion.

Quantitation of gene expression allows determination of the degree of inhibition (or enhancement) of gene expression in a cell or animal that contain one or more RNAi molecules. Lower doses of injected material and longer times after administration or integration of the RNAi can result in inhibition or enhancement in a smaller fraction of cells or animals (e.g., at least 10%, 20%, 50%, 75%, 90%, or 95% of targeted cells or animals). Quantitation of gene expression in a cell or animal can show similar amounts of inhibition or enhancement at the level of accumulation of target mRNA or translation of target protein. The efficiency of inhibition or enhancement can be determined by assessing the amount of gene product in the cell or animal using any method known in the art. For example, mRNA can be detected with a hybridization probe having a nucleotide sequence outside the region used for the interfering RNA, or translated polypeptide can be detected with an antibody raised against the polypeptide sequence of that region. Methods by which to quantitate mRNA and polypeptides are well-known in the art see, for example, Sambrook, J. et al. "Molecular Cloning: A Laboratory Manual," 2nd addition, Cold Spring Harbor Laboratory Press, Plainview, N.Y. (1989).

The present invention also relates to the regulation of expression of a family of genes. The term "family of genes" refers to one or more genes that have a similar function, sequence, or phenotype. A family of genes can contain a conserved sequence, i.e. a nucleotide sequence that is the same or highly homologous among all members of the gene family. In certain embodiments, the RNAi sequence can hybridize to this conserved region of a gene family, and thus one RNAi sequence can target more than one member of a gene family.

The methods of the present invention can also be used to regulate expression of genes within an evolutionarily related family of genes. Evolutionarily related genes are genes that have diverged from a common progenitor genetic sequence, which can or can not have itself been a sequence encoding for one or more mRNAs. Within this evolutionarily related family can exist a subset of genes, and within this subset, a conserved nucleotide sequence can exist. The present invention also provides methods by which to regulate expression of this subset of genes by targeting the RNAi molecules to this conserved nucleotide sequence. Evolutionarily related genes that can be regulated by the methods of the present invention can be endogenous or exogenous to a cell or an animal and can be members of a viral family of genes. In addition, the family of viral genes that can be regulated by the methods of the present invention can have family members that are endogenous to the cell or animal.

In other embodiments, the methods of the present invention can be used to regulate expression of genes, or family of genes, that are endogenous to a cell or animal. An endogenous gene is any gene that is heritable as an integral element of the genome of the animal species. Regulation of endogenous genes by methods of the invention can provide a method by which to suppress or enhance a phenotype or biological state of a cell or an animal. Endogenous genes that can be regulated by the methods of the invention include, but are not limited to, endogenous genes that are required for cell survival, endogenous genes that are required for cell replication, endogenous genes that are required for viral replication, endogenous genes that encode an immunoglobulin locus, and endogenous genes that encode a cell surface protein. Further examples of endogenous genes include developmental genes (e.g., adhesion molecules, cyclin kinase inhibitors, Wnt family members, Pax family members, Winged helix family members, Hox family members, cytokines/lymphokines and their receptors, growth/differentiation factors and their receptors, neurotransmitters and their receptors), tumor suppressor genes (e.g., APC, BRCA1, BRCA2, MADH4, MCC, NF 1, NF2, RB 1, TP53, and WTI) and enzymes (e.g., ACC synthases and oxidases, ACP desaturases and hydroxylases, ADP-glucose pyrophorylases, ATPases, alcohol dehydrogenases, amylases, amyloglucosidases, catalases, cellulases, chalcone synthases, chitinases, cyclooxygenases, decarboxylases, dextrinases, DNA and RNA polymerases, galactosidases, glucanases, glucose oxidases, granule-bound starch synthases, GTPases, helicases, hemicellulases, integrases, inulinases, invertases, isomerases, kinases, lactases, lipases, lipoxygenases, lysozymes, nopaline synthases, octopine synthases, pectinesterases, peroxidases, phosphatases, phospholipases, phosphorylases, phytases, plant growth regulator synthases, polygalacturonases, proteinases and peptidases, pullanases, recombinases, reverse transcriptases, RUBISCOs, topoisomerases, and xylanases).

In other embodiments, it may be desirable to regulate (modulate) tumor antigens in a cell so that, for example, these tumor cells can be detected by the host immune system. Many tumor antigens are well known in the art. See for example, Van den Eynde B J, van der Bruggen P. *Curr Opin Immunol* 1997; 9: 684-93; Houghton A N, Gold J S, Blachere N E. *Curr Opin Immunol* 2001; 13: 134-140; van der Bruggen P, Zhang Y, Chaux P, Stroobant V, Panichelli C, Schultz E S, Chapiro J, Van den Eynde B J, Brasseur F, Boon T. *Immunol Rev* 2002; 188: 51-64, which are herein incorporated by reference. Alternatively, many antibodies directed towards tumor antigens are commercially available.

Non-limiting examples of tumor antigens, include, tumor antigens resulting from mutations, include, but as: alpha-actinin-4 (lung carcinoma); BCR-ABL fusion protein (b3a2) (chronic myeloid leukemia); CASP-8 (head and neck squamous cell carcinoma); beta-catenin (melanoma); Cdc27 (melanoma); CDK4 (melanoma); dek-can fusion protein (myeloid leukemia); Elongation factor 2 (lung squamous carcinoa); ETV6-AML1 fusion protein (acute lymphoblastic leukemia); LDLR-fucosyltransferaseAS fusion protein (melanoma); overexpression of HLA-A2$^d$ (renal cell carcinoma); hsp70-2 (renal cell carcinoma); KIAAO205 (bladder tumor); MART2 (melanoma); MUM-1f (melanoma); MUM-2 (melanoma); MUM-3 (melanoma); neo-PAP (melanoma); Myosin class I (melanoma); OS-9g (melanoma); pml-RARalpha fusion protein (promyelocytic leukemia); PTPRK (melanoma); K-ras (pancreatic adenocarcinoma); N-ras (melanoma). Examples of differentiation tumor antigens include, but not limited to: CEA (gut carcinoma); gp100/Pme117 (melanoma); Kallikrein 4 (prostate); mammaglobin-A (breast cancer); Melan-A/MART-1 (melanoma); PSA (prostate carcinoma); TRP-1/gp75 (melanoma); TRP-2 (melanoma); tyrosinase (melanoma). Over or under-expressed tumor antigens include but are not limited to: CPSF (ubiquitous); EphA3; G250/MN/CAIX (stomach, liver, pancreas); HER-2/neu; Intestinal carboxyl esterase (liver, intestine, kidney); alpha-foetoprotein (liver); M-CSF (liver, kidney); MUC1 (glandular epithelia); p53 (ubiquitous); PRAME (testis, ovary, endometrium, adrenals); PSMA (prostate, CNS, liver); RAGE-1 (retina); RU2AS (testis, kidney, bladder); survivin (ubiquitous); Telomerase (testis, thymus, bone marrow, lymph nodes); WT1 (testis, ovary, bone marrow, spleen); CA125 (ovarian).

The methods of the present invention can also be used to regulate the expression of a specific allele. Alleles are polymorphic variants of a gene that occupy the same chromosomal locus. The methods of the present invention allow for regulation of one or more specific alleles of a gene or a family of genes. In this embodiment, the sequence of the RNAi can be prepared such that one or more particular alleles of a gene or a family of genes are regulated, while other additional alleles of the same gene or family of genes are not regulated.

The following examples are offered by way of illustration, not by way of limitation. While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification.

All publications and patent documents cited in this application are incorporated by reference in pertinent part for all purposes to the same extent as if each individual publication or patent document were so individually denoted. By their citation of various references in this document, Applicants do not admit any particular reference is "prior art" to their invention.

EXAMPLES

Materials and Methods
In Situ Hybridization

HeLa cells were grown on the surface of silane-coated slides overnight and fixed with 4% paraformaldehyde (pH 7.4) for 4 minutes. After air drying the slides, a chamber was utilized for easy treatments of the attached cells with DNase at 37° C. for 16 hours. DNase Master Mix contained 10×TurboDNase Buffer (Ambion), 100 units DNase1, 100 units of TurboDNase, and 100 units of Suprasin in a final volume of 200 µl. The cells were then washed with 1×PBS and subsequently incubated at 95° C. for 5 minutes. First strand cDNA was synthesized with an RT-Master Mix of 10×RT Buffer (Applied Biosystems), 2.5 mM MgCl$_2$, 10 mM dNTP mixture, 10 pM Random Hexamers, 100 units RNase Inhibitor, and 500 units of reverse transcriptase in a final volume of 200 µl. The RT reactions were completed using the following conditions: 30 minutes at room temperature, 3 hours at 42° C., and 5 minutes at 95° C. For in situ hybridization, the cells were incubated at 65° C. for one hour in blocking buffer (10 mM Tris-HCl, 50 mM KCl, 1.5 mM MgCl$_2$, 1 Triton-X, 20 µM Random DNA in a final volume of 200 µl). After blocking, the cells were hybridized at 70° C. for one hour with 10 µM of specific intron spanning probes (sequences in table 1, 3). The slides were then washed two times with pre-warmed PBS.

Dilutional Single Cell RT-PCR

The HeLa cultures were diluted to a few cells in each bright field. RNA was extracted from 15 individual cells that were picked under the guide of a confocal microscope. First strand cDNA synthesis was made from the RNA by using SMART and CDS III 3' oligonucleotides and Powerscript reverse transcriptase from Clontech according to manufacturer instructions. The first strand cDNA was then used for PCR amplification using the LD primer, DSIII PCR primer, and Advantage2 Polymerase mix from the Clontech cDNA library kit.

Preparation and Fractionation of Cell Extracts

Cytoplasmic extracts were prepared from HeLa cells transfected with different vectors. Cells were harvested after 24 h transfections and centrifuged at 1000g for 5 minutes at 4° C. Cell pellets were washed three times with ice-cold PBS, pH 7.2, and lysed for 10 minutes on ice in three packed cell volumes of lysis buffer (20 mM Tris-HCl, pH 7.4; 200 mM NaCl; 14 mM MgCl$_2$, 20 units suprasin; 100 units of protease inhibitor; 100 µg/ml of Cyclohexamide; 0.1% (v/v) Triton X-100). Nuclei were isolated by centrifugation at 5000g for 10 minutes at 4° C. The supernatant contained the cytoplasmic extract and was immediately used for RNA extraction with Trizol (Invitrogen). Nuclear extracts were prepared by washing the pellet once in lysis buffer and twice in 1×PBS, pH 7.2. Nuclear RNA was then collected using Trizol reagent. Purity (>98%) and integrity of nuclei were determined microscopically.

Ribonuclease Protection Assay (RPA)

Using the Direct Protect Lysate RPA kit from Ambion, cytoplasmic lysate was treated with RNase cocktail buffer and incubated with RNase A and T cocktail at 37° C. for 30 minutes. Nucleases were removed by incubation with sodium sacrosyl and proteinase at 37° C. for 30 minutes. RNA was precipitated using 99% ethanol and glycogen blue and subsequently DNase treated with TurboDNase (Ambion) prior to separation on a 10% denaturing PAGE/8M urea.

Northern Blot for the Dicer Products

Total RNA was collected using Trizol (Invitrogen) and precipitated with 99% ethanol. 30 µg of total RNA was loaded per lane and separated out on a 10% PAGE/Urea gel. The RNA was then transferred onto a Nylon membrane (Amersham) and blocked with Salmon sperm DNA for 6 hours. The blocked membrane was hybridized overnight with radiolabeled S-AS probes spanning the overlap region of the TS and rTSα genes. The probe was made by random priming of overlap DNA using $^{32}$P-labeled nucleotide and the Amersham random priming kit. All membranes were washed one time with low stringency and two times with high stringency buffer, each for 1 hour, and signal was detected with a Typhoon phosphor-imaging instrument.

Cell Culture and Transfection

HeLa cells were cultured in D-MEM supplemented with 10% FBS. The cells in logarithmic growth were transfected with plasmids containing the luciferase gene with either or both sense or antisense overlap region. At 24 hours post-transfection, cells were used for further applications. The pGL3 control vector (Promega), was used for making all S-AS constructs. We engineered Pst1 and EcoR1 restriction sites downstream of the firefly luciferase for cloning. A BamH1 sequence was used to form a hairpin between overlap regions and to construct a vector with a consecutive S-AS sequence (primers and probe sequences are listed in table 3). The same vector was used as a template for IVT of S-AS overlap mRNA, using MEGAscript transcription kit (Ambion).

Real-Time PCR

Real-time PCR (RT-PCR) was carried out with the GeneAmp 7000 machine (Applied Biosystems). The PCR reactions contained 20 ng cDNA, Sybrgreen or Universal Mastermix (Applied Biosystems), 300 nM of forward and reverse primers, and 200 nM of probe in a final reaction volume of 50 µl (primers and probe sequences are listed in table 1, 3). The primers and probe were designed using PrimerExpress software (AppliedBiosystem). They were strand specific for each S-AS pair and the probe covered exon boundaries to eliminate the chance of genomic DNA amplification. The PCR conditions for all genes was as follows: 50° C. for 2 minutes and 95° C. for 10 minutes 40 cycles of 95° C. for 15 seconds and 60° C. for 1 minute. The results are based on the cycle threshold (Ct) values. Differences between the Ct values for the experimental genes and the reference gene (either β2M or GAPDH) were calculated as ΔΔCt.

Example 1

Knockdown of Antisense Transcripts

In the present context, the only approach to affect antisense transcript levels has been by use of siRNA aiming at achieving efficient transcript knockdown. The later term—knockdown—was introduced by us in the early 1990s while working on antisense oligonucleotides (Wahlestedt, C. (1994) Antisense oligonucleotide strategies in neuropharmacology. *Trends Pharmacol Sci* 15 (2):42-46) but is equally applicable to siRNA.

Expression profiling revealed frequent concordant regulation of sense/antisense pairs. Using siRNA, we have provided experimental evidence that perturbation of an antisense RNA by siRNA can alter the expression of the corresponding sense messenger RNAs. However, this regulation can either be discordant (antisense knockdown results in sense transcript elevation) or concordant (antisense knockdown results in concomitant sense transcript reduction). In Table 2 a range of human and mouse antisense transcripts that have been targeted by siRNA is shown. In every case, two or more siRNAs were targeted to the non-overlapping part of the antisense strand and knockdown was confirmed by use of RT-PCR. Table 2 illustrates that coding as well as non-coding antisense can be targeted in an identical manner and that either category is capable of regulating the corresponding sense transcripts—either in a concordant or disconcordant manner. Here we propose two new pharmacological strategies based on the knockdown of antisense RNA transcripts by siRNA (or another RNA targeting principle):

Strategy 1: In the case of discordant regulation, by knocking down only the antisense transcript, elevates the expression of the conventional (sense) gene. Should that latter gene encode for a known or putative drug target, then knockdown of its antisense counterpart could conceivably mimic the action of a receptor agonist or an enzyme stimulant. Table 2 gives examples where knockdown of antisense (coding as well as non-coding) transcripts was demonstrated to discordantly regulate sense expression. For example, in Parkinson's disease enhanced activity of the mitochondrially localized kinase, PINK', is arguably desirable and knockdown of its non-coding antisense partner might be a means to that end. Further, to stimulate angiogenesis, in certain circumstances, enhanced signaling through the G-protein-coupled receptor (GPCR), CD97, may be achieved by targeting of its (coding) antisense partner, Ddx-39.

An example of strategy I (elevation of PINK1, e.g. Parkinson's disease):

```
PINK-AS:
PINK-AS siRNA-a:
                                    (SEQ ID NO: 1)
GGAAGCTGTAGCTAGAACATCTGTT
``` siRNA to the corresponding antisense transcript, or a single energetically symmetric siRNA that simultaneously targets overlapping sense and antisense transcripts. As follows from Table 2, such dual concomitant targeting may, for example be relevant to pursue in the case of hypoxia-inducible factor 1 alpha, a target whose inhibition may be beneficial in various medical conditions. Another example in Table 2 is the Adrenomedullin AM1 receptor, a GPCR where reduced signaling could also prove to be of therapeutic benefit.

With an emerging functional RNA world, there are new potential drug targets to be considered. Among these are large numbers of natural occurring antisense transcripts with a capacity to regulate the expression of sense transcripts including those that encode for conventional drug targets. Since many of these antisense transcripts represent non-coding RNA, they cannot be manipulated at the protein level. With the use of siRNA we have shown that antisense transcript knockdown can result in either increase (discordant regulation) or decrease (concordant regulation) of sense transcript expression. These findings and concepts form a basis for novel pharmacological strategies.

TABLE 2

Effects of siRNA induced antisense transcript knockdown on sense transcript expression.

| Sense | Antisense (Coding) | Antisense (Non-Coding) | Discordant Regulation (Sense Increase) | Concordant Regulation (Sense Decrease) | Species; Cell Line** |
|---|---|---|---|---|---|
| CD97 | Ddx-39 | N/A* | Yes | No | mouse; N2A |
| TS-α | rTS-α | N/A | Yes | No | human; HeLa |
| C/EBP delta | I530027A02 | N/A | No | Yes | mouse; Hepa1-6 |
| CDC23 | Kif20a | N/A | No | Yes | mouse; Hepa1-6 |
| PINK1 | N/A | PINK-AS | Yes | No | human; SH-SY5Y |
| HIF1α | N/A | aHIF1α | No | Yes | human; HeLa |
| Gnbp3g | N/A | Gnbp3g-AS | No | Yes | mouse; N2A |
| Adrenomedullin AM1 receptor | N/A | AdmR-AS | No | Yes | mouse; N2A |
| 6330439J10 (3-oxoacid CoA transferase) | N/A | A230019L24 | No | Yes | mouse; N2A |
| CtpW85 (Cathepsin W) | N/A | CtpW-AS | No | Yes | mouse; N2A |
| BACE1 | N/A | BACE1-AS1 BACE1-AS2 | No | Yes | human and mouse; SH-SY5Y, SK-N-MC, N2A |

```
-continued
PINK-AS_siRNA-b:
                                    (SEQ ID NO: 2)
CAGGTAAGTAGTCTCCTCTATCATT PINK-AS_siRNA-c:
                                    (SEQ ID NO: 3)
TCTCAACCCAAAGCCTGCTTTGTTA
```

Strategy 2: In the case of concordant regulation, concomitant knock down of both antisense and sense transcripts and thereby achieve synergistic reduction of the conventional (sense) gene expression. These concepts are illustrated in FIGS. 2A and 2B. When siRNA is used to achieve knockdown, then this strategy would be further tested by applying one siRNA targeted to the sense transcript and another Example of Strategy II (Concomitant Knockdown of Antisense and Sense Transcripts for Use in Alzheimer's Disease):

```
BACE1-AS:
siRNA-a:
                                    (SEQ ID NO: 4)
CCCTCTGACACTGTACCATCTCTTT siRNA-b:
                                    (SEQ ID NO: 5)
AGAAGGGTCTAAGTGCAGACATCTG siRNA-c:
                                    (SEQ ID NO: 6)
```

-continued
CCAGAAGAGAAAGGGCACT

BACE1:
siRNA-a:
(SEQ ID NO: 7)
GAGCCTTTCTTTGACTCTCTGGTAA siRNA-b:
(SEQ ID NO: 8)
CCACGGAGAAGTTCCCTGATGGTTT

Example 2

Natural Antisense Mediated Regulation of Gene Expression in Mammals

Naturally occurring antisense transcripts (NAT) have been reported for 20% of the human genome. Recent reports indicate the existence of NAT for at least 72% of mouse transcripts. Most of the natural antisense transcripts are cis-encoded antisense. By definition, cis-NAT are complementary mRNA with an overlapping transcription unit at the same chromosomal locus. Trans-NAT are complementary RNA transcribed from different chromosomal locations. Chimeric transcripts are mRNA with identity to more than one region of the genome and might be an artifact of cDNA library production. Over 70% of cis-NAT have tail to tail format with 3' overlap, while 15% have head to head format with a 5' overlapping region. The remaining molecules have intronic or coding sequence overlaps. Many NAT show no open reading frame and are classified as non-coding RNA.

The interaction between antisense and corresponding sense transcript partners does not follow a unified and predictable pattern. The interactions between two NAT targeting of human genes, HIF-1α and TS, were investigated. The antisense transcript for HIF (aHIF) is a non-coding RNA that may alter HIF splicing and also the ratio between the two splice forms of HIF. Specifically, it has been hypothesized that the antisense molecule may destabilize one splice variant of HIF mRNA and shift the balance in favor of the other variant Editing is another proposed function of NAT through transformation of adenosine to inosine nucleotide in pre-mRNA. The antisense sequence for TS (rTSα) induces editing of the sense RNA molecule, and thereby drives TS mRNA down-regulation. Importantly, the NAT for TS is protein coding, whereas there are no predicted opening reading frames for aHIF. These two known candidates from coding and non-coding subgroups of NAT were chosen for study, that could potentially modulate sense mRNA through two distinct modes of action.

One of the most exciting findings in genome biology in recent years has been the discovery of RNA interference (RNAi), which has been proposed as a possible mechanism by which NAT may regulate gene expression. RNAi is an innate cellular process activated when a double-stranded RNA (dsRNA) enters the cell. Originally discovered in *Caenorhabditis elegans*, RNAi is an evolutionarily conserved, post-transcriptional gene silencing mechanism. The dsRNA is processed by the RNase III enzyme called Dicer into small duplex RNA molecules of approximately 21-22 nucleotides, termed small interfering RNA (siRNA). The siRNA molecules then interact with a multi-protein complex, termed RNA-induced silencing complex (RISC), resulting in sequence specific association of the activated RISC complex with the cognate RNA transcript. This interaction leads to sequence-specific cleavage of the target transcript. It has been suggested that dsRNA derived from endogenous S-AS duplexes may act through the RNAi pathway by serving as a substrate for Dicer, and the subsequent generation of siRNA. The siRNA would then regulate one or both of the S-AS transcripts.

In summary, NAT has been proposed to regulate gene transcription, RNA splicing, polyadenylation, editing, stability, transport, and translation. The aim of this study was to explore the mechanism of NAT action. Shared complementary regions in exons of NAT imply probability of cytoplasmic duplex formation and intronic overlap sequence suggests nuclear dsRNA duplexes. In theory, all proposed regulatory mechanisms would require RNA duplex formation in the cytoplasm or nucleus, therefore, cellular evidence for RNA duplexes, using HIF and TS as model genes, were the main focus of this work.

Figure 4:
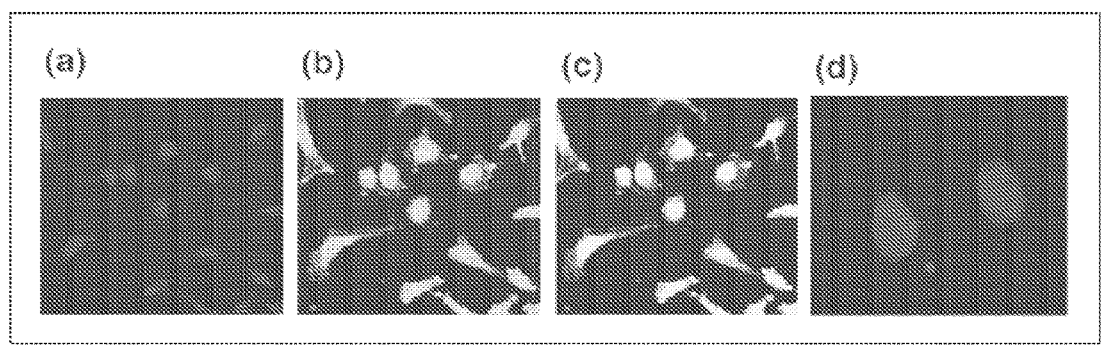
FIG. 4 is a fluorescent image showing single cell RNA expression of TS transcripts. (a) Antisense probe (b) Sense probe (c) both sense and antisense probes bound to the fixed and reverse transcribed TS RNA in HeLa cells. Probes were designed to cover exon boundaries and a part of the overlap region in a strand specific manner. (d) Signals from the actin probe show that the method was working optimally. All the probes were intron spanning to avoid background signal from contaminating DNA.

Results: The in situ hybridization method was used to assess the simultaneous presence of both endogenous TS and rTSα. HeLa cells were grown on the surface of slides, fixed and treated with DNase (see materials and methods). First strand cDNA was synthesized and subjected to in situ hybridization using strand specific intron spanning probes (schematics for TS sense-antisense gene and probes are illustrated in FIG. 3A). Importantly, the use of intron spanning probes eliminate detection of contaminating DNA, and the probes covered at least a portion of the overlap region for both transcripts, ensuring that the signals were obtained from a full mRNA. The results show both transcripts co-exist in single cells at the same time (FIG. 4).

Figure 5:
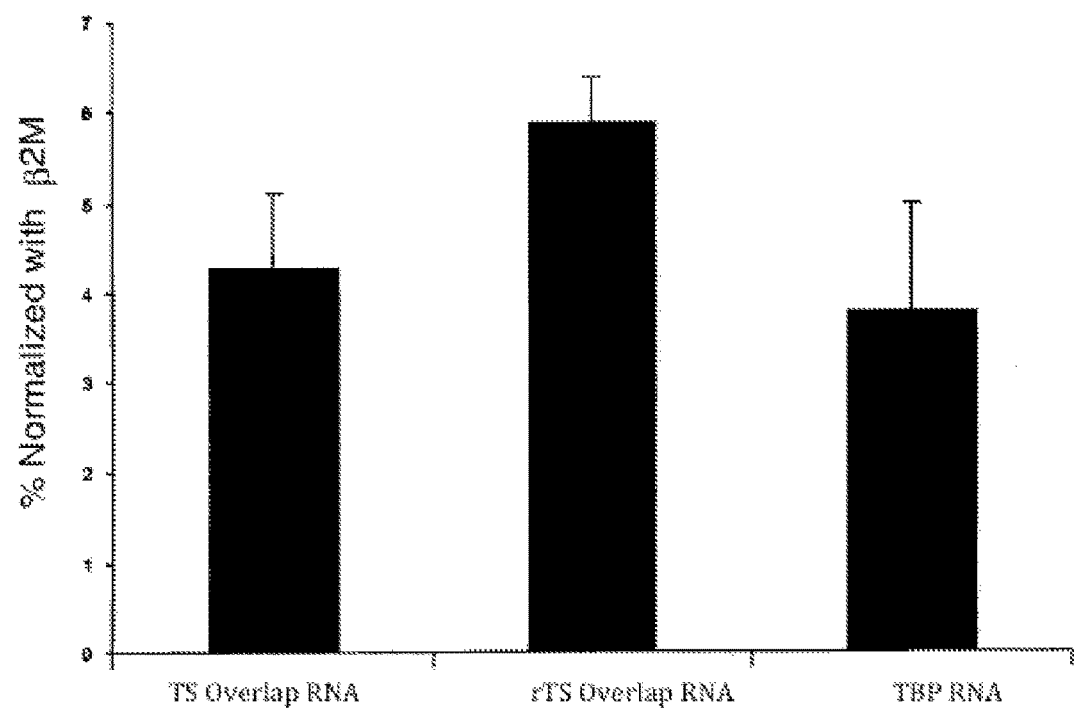
FIG. 5 is a graph showing the endogenous single cell mRNA expression of TS sense and antisense molecules. Real-time PCR primers were designed to span between the overlapping and non-overlapping regions. Expression of the low abundant TATA box binding protein was also quantitated to determine the sensitivity of the assay. All samples were normalized to β2-microglobulin and plotted are the average results from 15 individual cells.

To demonstrate the co-existence of S-AS pairs in single cells, as opposed to cell populations, a method was designed to detect the co-expression of NAT within a single cell. RNA was extracted from a single cell, under microscopic guide, for quantitation of TS and rTSα transcripts by real-time PCR using TaqMan technology (FIG. 5). Primers were strand specific for both sense and antisense. S-AS expression was normalized to a highly abundant mRNA, β2-microglobulin ($\beta_2$M), as an internal control. The sensitivity of the methods was gauged by comparing the expression of TS and rTSα with that of a relatively low abundance gene, TATA binding protein (TBP). As shown in FIG. 5, TS and rTSα were 7% of $\beta_2$M expression as expected for genes with low expression and TBP levels were 5% relative to $\beta_2$M. Thus, both S-AS transcripts were present in single cells at approximately similar levels.

Figure 6:
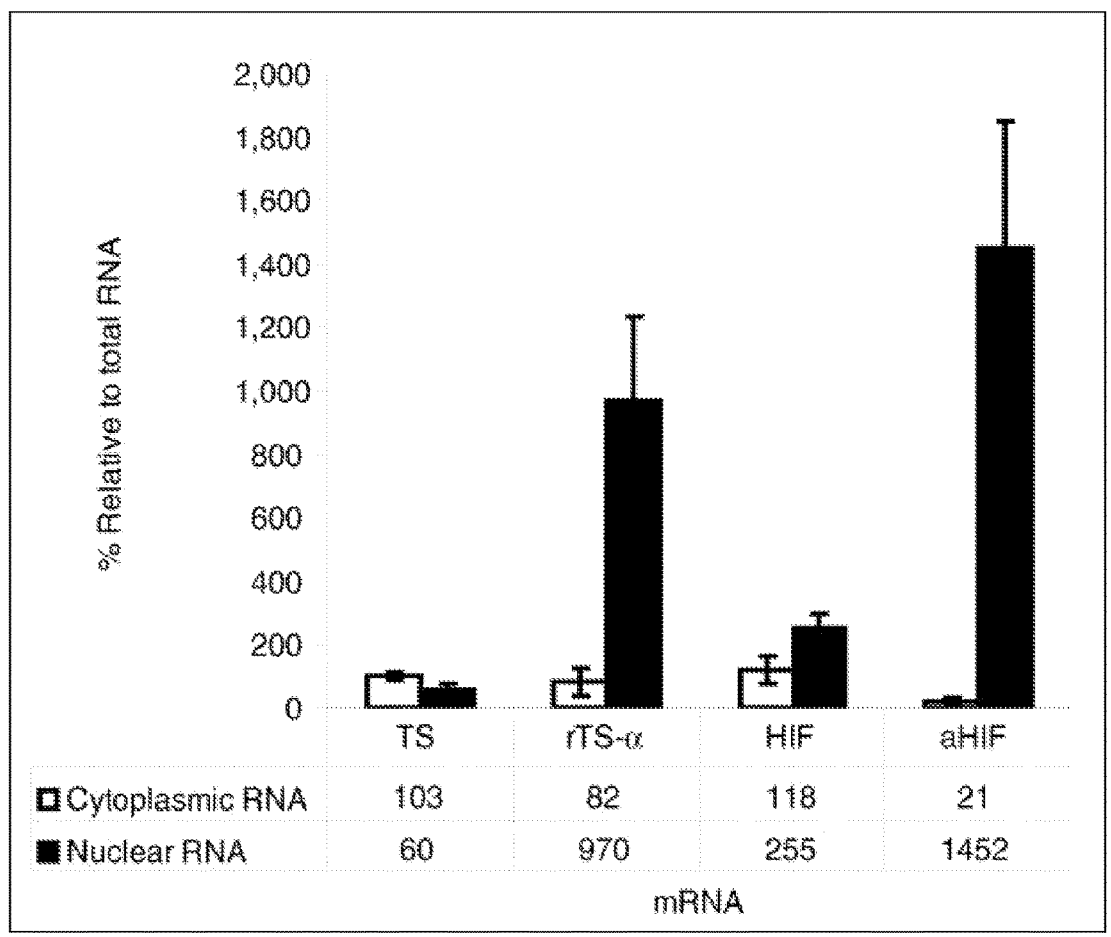
FIG. 6 is a graph showing the cellular localization of TS sense (TS) and its antisense (rTSα), HIF sense (HIF) and its antisense (aHIF), in three cell lines (HeLa, SK-N-MC and HEPG2). The cytoplasmic and nuclear RNA were normalized to total RNA.

The cellular location of TS and HIF transcripts was next investigated. Cytoplasmic and nuclear extracts were prepared from HeLa cells and immediately used for RNA extraction. RNA was then reverse transcribed and used for quantitation of S-AS transcripts by real-time PCR. Importantly, the sense strands of both genes had similar expression levels in the cytoplasm and nucleus, in contrast, antisense transcripts levels were 1000-fold higher in the nucleus compared with the level detected in the cytoplasm. Thus, those data suggest a spatial dissociation in S-AS pairs (FIG. 6).

Figure 3B:
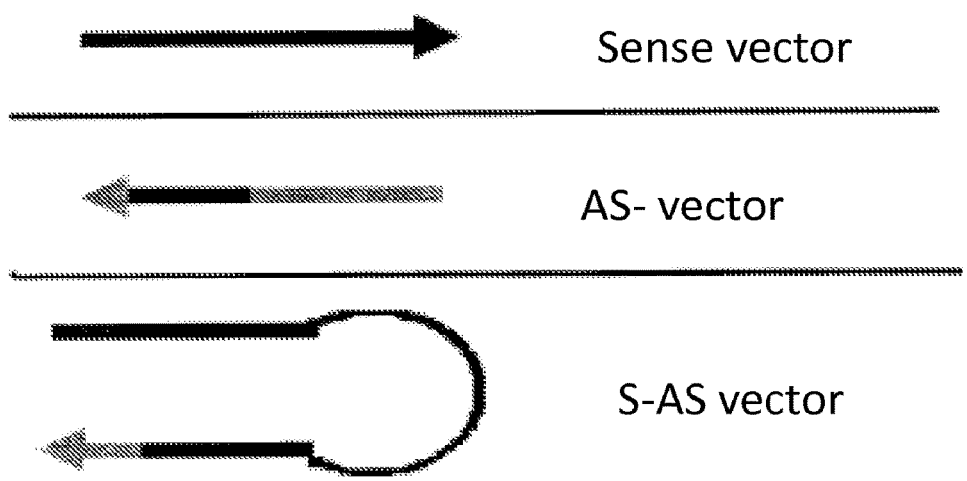
FIG. 3B shows the conformation of vectors used for transfection and S-AS RNA production. Sense vector makes an RNA with 3' sense sequence, antisense vector makes an RNA with 3' antisense sequence, and S-AS vector makes RNA with consecutive sense-antisense sequence with a hairpin sequence between sense and antisense RNA sequence.
Figure 7:
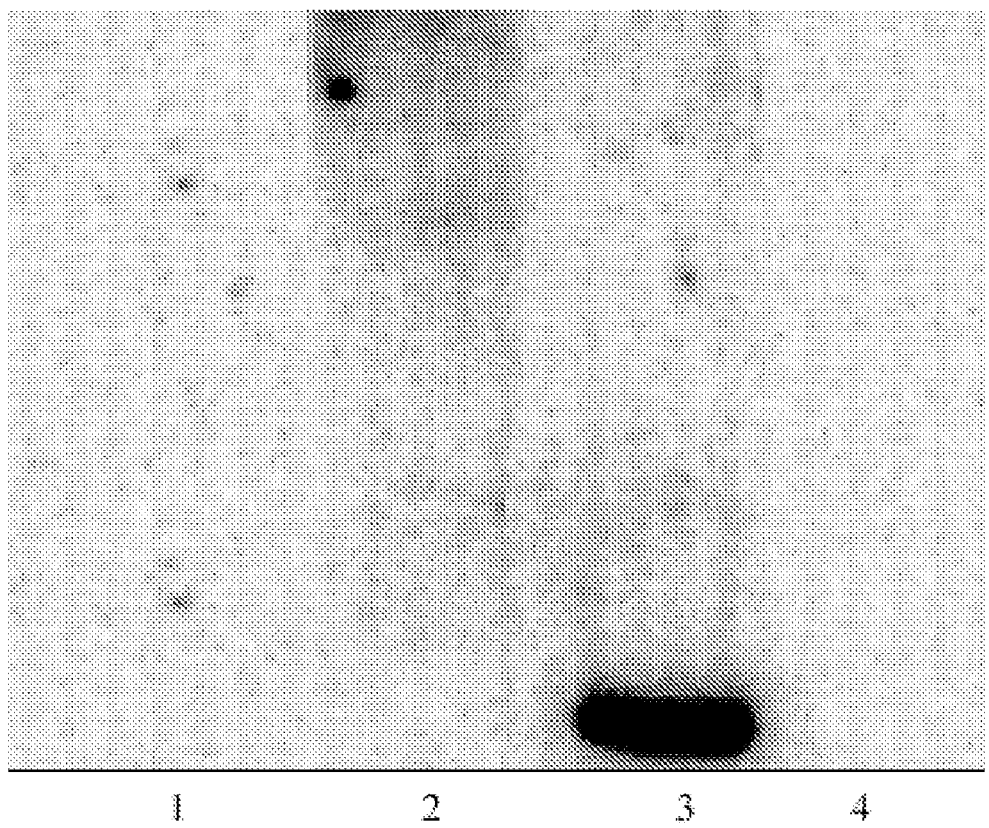
FIG. 7 is a blot showing RPA of cytoplasmic RNA. Lane 1 Cytoplasmic lysate of HeLa cells. Lane 2 Cytoplasmic lysate of HeLa cells overexpressed with S-AS. Lane 3 lystate from HeLa cells transfected with in vitro transcribed S-AS RNA duplex. Lane 4 Total RNA from HeLa cells overexpressing S-AS, all treated with RNAse A+T, separated on denaturing PAGE and probed for overlap region of Thymidylate Synthase mRNA.
Figure 8:
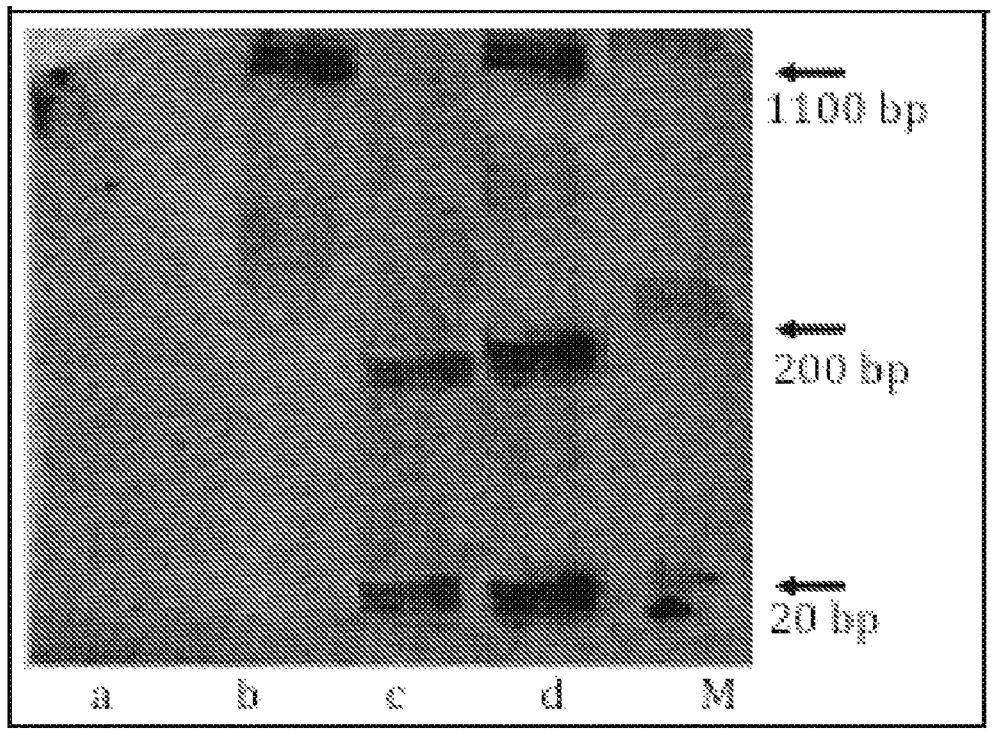
FIG. 8 shows a Northern blot for Dicer products. Total RNA from lane (a) HeLa cells, lane (b) HeLa cells overexpressed with S-AS mRNA, lane (c) HeLa cells transfected with IVT-overlap dsRNA, lane (d) HeLa cells overexpressing consecutive S-AS RNA (m) marker.

Next, the formation of S-AS duplexes in the cytoplasm of HeLa cells, was explored using the Ribonuclease Protection Assay (RPA). Although HeLa cells endogenously express both S-AS mRNA, three vectors were constructed which produce sense, antisense or consecutive S-AS overlapping mRNA in eukaryotic cells (FIG. 3B). For two of the constructs, the 3' overlap region of TS and rTSα were placed downstream of a luciferase gene, thereby allowing transfection efficiency to be monitored. These two vectors were co-transfected into the HeLa cells, producing a condition of overexpressed RNA with the overlap region. For the third construct, both the sense and antisense complementary regions were engineered in the same vector with a short hairpin between S-AS overlap parts. RNA from this vector will supposedly fold back on itself to form a RNA duplex in cells. For an additional control, in vitro transcription (IVT) of the vectors were performed, made artificial RNA duplexes and then transfected into the cells. To investigate the presence of RNA duplexes in transfected and untreated cells, cytoplasmic lysate was isolated and subsequently treated with RNAse A and T prior to separation on a polyacrylamide gel. Existing RNA duplexes were detected with radiolabeled probes for the S-AS overlap regions. S-AS duplexes were detected in cells transfected with IVT dsRNA. In cells overexpressed with S-AS or cells expressing endogenous levels of NAT, RNA duplexes were not detected (FIG. 7). These data suggest that endogenous NAT, as well as synthetically overexpressed S-AS RNA, did not form duplexes in the cytoplasm of HeLa cells. It is possible that putative RNA duplexes in the living cells are transient and labile and are processed to endogenous siRNA or other intermediate products rapidly. To investigate this possibility a Northern Blot analysis was designed with radiolabeled probes spanning the overlap region of the S-AS mRNA. These randomly designed probes, which can potentially detect S-AS sequences of any length from full length RNA to less than 20 bp Dicer products, were used to search for the presence of processed RNA. The hypothesis was that, if RNA duplexes are present, they should ultimately be processed by Dicer into the 21 base pair RNA oligonucleotides. HeLa cells were transfected with the same vectors used in the previously described experiment, which produced sense, antisense, or S-AS RNA. The RNA duplexes from the S-AS overlap region produced by IVT served as a positive control and were transfected into the cells. Dicer products were only present in cells transfected with IVT dsRNA or cells transfected with a vector which produced internal hairpin dsRNA (FIG. 8). Positive bands were detected in overexpressed cells at 1100 bp, (full length RNA originate from vector), as well as at 200 bp in IVT RNA transfected cells. However, the lack of 21 bp RNA molecules in untransfected or overexpressed cells suggests S-AS duplexes were not processed by Dicer.

Figure 9:
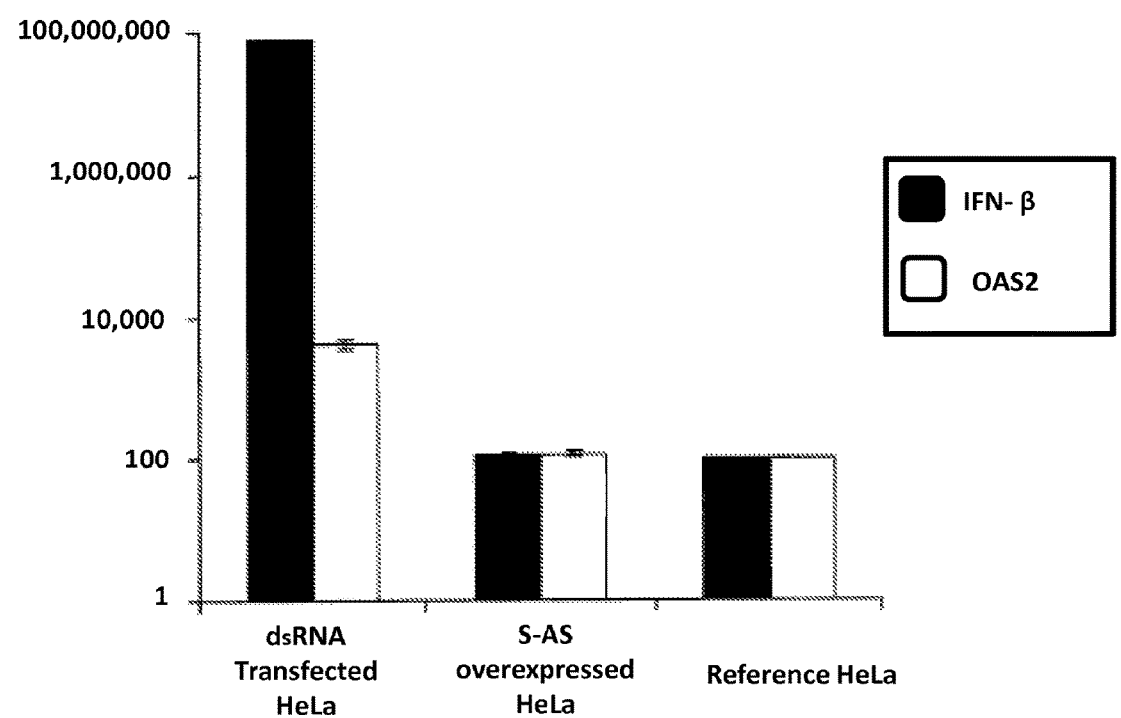
FIG. 9 is a graph showing IFNβ and OAS2 mRNA expression. The interferon response was quantified by qRT-PCR in HeLa cells either transfected with IVT-dsRNA TS or overexpressing S-AS and reference HeLa. The mRNA levels were normalized to GAPDH.

The interferon signaling cascade is part of the cell's antiviral defense mechanism and can be triggered by dsRNA. Interferon-β (IFN-β) and 2', 5'-oligoadenylate synthetase-2 (OAS2) mRNA levels were measured in cells overexpressing S-AS transcripts (FIG. 9). IFN-β mRNA levels were upregulated by 10,000-fold in cells transfected with in vitro transcribed dsRNA but were unchanged in cells with overexpressed S-AS transcripts. OAS2 levels were also up-regulated by about 600-fold only in the cells with IVT duplex RNA transfection. These data indicate that cytoplasmic RNA duplexes with S-AS mRNA are unlikely to be formed, nevertheless, it is possible that the interferon pathway may be unresponsive to intracellular RNA duplexes.

Taken together, the present studies suggest that NAT does not form cytoplasmic RNA duplexes that activate RNAi mechanisms. Overlapping transcripts in antisense orientation, be they protein coding or non-coding, have the potential to form dsRNA, a substrate for a number of different RNA-modification pathways. One prominent route for dsRNA is its breakdown by Dicer enzyme complexes into small RNA. Several experimental approaches were used to try to identify the presence of RNA duplexes in the cytoplasm of cells, and to detect Dicer products, involved in processing of dsRNA. The results, using synthetic S-AS constructs, as well as endogenous NAT, did not support the presence of cytoplasmic RNA duplexes or engagement of RNAi mechanism.

Concomitant presence of both S-AS mRNA is one requirement for NAT regulation and many in silico predicted NAT candidates can be ruled out on this criterion alone. Expression levels of S-AS are also important as these could predict the mode of regulation. High levels of S-AS in a single cell, as suggested from our experimental model, argues against RNAi involvement. However, another explanation for this phenomenon is a translation block or other kind of RNA mediated regulation of gene expression, without alteration of mRNA levels. Expression assessment and evaluation of the mRNA levels would be recommended as a first step in studying other predicted S-AS candidates.

Alterations in antisense transcript levels can affect the sense mRNA level; however, S-AS changes are not necessarily reciprocal. Recently, we showed that antisense transcript knock down elevated sense transcript levels but the reverse interaction was not observed. This observation suggests antisense mRNA is involved in sense transcript regulation, but sense mRNA does not appear to control antisense expression. If endogenous RNAi were involved in mammalian S-AS phenomena, then it may be expected that both transcripts exhibit similar expression profiles in knockdown experiments.

Overall, the above observations are consistent with the conclusion that RNAi mechanisms are not engaged by S-AS gene regulation. Indeed, further support is derived from two other observations: first, small RNA molecules were not detected even for highly expressed S-AS, implying Dicer-independent RNA processing. Second, the interferon cascade was not activated by NAT. Indeed, it may have been expected that, if at least 70% of mammalian genes have NAT and the mechanism is through RNA-duplex formation, there would be a cumulative interferon response. Our studies show a dramatic β-Interferon and OAS2 mRNA induction with dsRNA transfection but not in cells overexpressing S-AS, indicating the absence of duplexes of NAT.

To date there are no reports for endogenous mammalian siRNA derived from NAT in the literature (Makalowska I, Lin C F, Makalowski W: Overlapping genes in vertebrate genomes. *Comput Biol Chem* 2005, 29(1):1-12.). It is possible, however, that endogenous siRNA could be programmed into RISC and that this effect would be long term and lead to down-regulation of target RNA. In theory, a 500 bp dsRNA would produce a library of siRNA. This siRNA collection could impair protein production at two levels, either by degrading many "off targeted" mRNAs or by blocking translation. The extent of this non-specific effect would be much greater when considering the large number of genes known to have antisense sequences.

Consistent with data in the present investigation, although the presence of endogenous miRNA has been reported, no endogenous mammalian siRNA has been described so far. This observation also argues against processing of endogenous RNA duplexes in a Dicer-dependent pathway and further substantiates our findings.

Our data suggest that antisense expression is not linked to transcript degradation pathways. However, our methods do not completely exclude the formation of RNA duplexes in the cell nucleus, or any proposed functions for NAT regulation of gene expression like editing, nuclear retention splicing or transport. Although many different functions and mechanisms have been suggested for NAT, there are no systematic approaches for classification or prediction of mechanism suggested to date. Our study could be a start for a functional approach to NAT studies that could lead to a categorization of NAT based on their unique bioinformatic features. Our methodology could also be expanded to provide a systematic approach to natural antisense mediated regulation of gene expression.

TABLE 3

Primer and probes used for in situ hybridization, real time PCR and cloning.

| Primer Name | Sequence | Gene |
|---|---|---|
| Actin Probe with 5' Texas Red | GAAGATCAAGATCATTGCTCCTC (SEQ ID NO: 9) | Human β-Actin |
| HIF1A-sense-F | CTGCACAAACTTGGTTAGTTCAATTTT (SEQ ID NO: 10) | HIF1α_TaqMan Primer |
| HIF1A-sense-R | ACTGCAATGCAATGGTTTAAATACC (SEQ ID NO: 11) | HIF1α_TaqMan Primer |
| HIF1A-sense-P | TTTTTTAGTATGTTCTTTAATGCTGGATCACAGACAGCTC (SEQ ID NO: 12) | HEF1α_TaqMan probe |
| antiHIF1A-antisense-F | ATACTCTTTTCAATGGGATATTATGGTTGT (SEQ ID NO: 13) | aHIF1α_TaqMan Primer |
| antiHIF1A-antisense-R | TGGTACTGGTTATTTCTACATTTATCTTAGTG (SEQ ID NO: 14) | aHIF1α_TaqMan Primer |
| antiHIF1A-antisense-P | TAACATGACATTTAGGGACTCAACATACATTAAGGTGATG (SEQ ID NO: 15) | aHIF1α_TaqMan probe |
| TS-sense Probe with 5' Fluorescein | GCCACTGAAAATTCAGCTTCA (SEQ ID NO: 16) | Thymidylate Synthase |
| TS-Overlap-F | ATCCGCATCCAACTATTAAAATGG (SEQ ID NO: 17) | TS-Overlap TaqMan Primer |
| TS-Overlap-R | CCAGCCCAACCCCTAAAGAC (SEQ ID NO: 18) | TS-Overlap TaqMan Primer |
| rTS-Antisense Probe with 5' Texas Red | CCTCAGGAATCAGCTAAAGCAAA (SEQ ID NO: 19) | rTSα |
| PstTS antisense-F | aaactgcagAACTTTTACCTCGGCATCCA (SEQ ID NO: 20) | TS Cloning primer |
| EcoTS antisense-R | cggaattcAGCGAGAACCCAGACCTTTC (SEQ ID NO: 21) | TS Cloning primer |
| EcoTS sense-F | cggaattcAACTITTACCTCGGCATCCA (SEQ ID NO: 22) | rTSα cloning |
| PstTS sense-R | aaactgcagAGCGAGAACCCAGACCTTTC (SEQ ID NO: 23) | rTSα cloning |
| E-TS sense-F | cggaattcAACTITTACCTCGGCATCCA (SEQ ID NO: 24) | Consecutive TS S-AS cloning |
| P-TS antisense-F | aaactgcagAACTTTTACCTCGGCATCCA (SEQ ID NO: 25) | Consecutive TS S-AS cloning |
| BamHITS sense-R | cgggatccAGCGAGAACCCAGACCTTTC (SEQ ID NO: 26) | Consecutive TS S-AS cloning |
| TS-sense-F | AAAACCAACCCTGACGACAGA (SEQ ID NO: 27) | TS_Taqman primer |
| TS-sense-R | GCAGCGCCATCAGAGGAA (SEQ ID NO: 28) | TS_Taqman primer |
| TS-sense-P | CATCATGTGCGCTTGGAATCCAAGAGA (SEQ ID NO: 29) | TS_Taqman probe |
| rTS-a)antisense-F | GCATTTCAAGTATCCCGTGATG (SEQ ID NO: 30) | rTSα_Taqman primer |
| rTS-a)antisense-R | TGTTGAGTAGCCGGGATCCT (SEQ ID NO: 31) | rTSα_Taqman primer |
| rTS-a)antisense-P | AGCGGGCTTCCTACATGCCTCCC (SEQ ID NO: 32) | rTSα_Taqman probe |

Example 2

A Nuclear Retained Noncoding RNA Transcript Regulates Expression of β-Secretase Through a Feed-Forward Mechanism Rapid Amplification of cDNA Ends (RACE): Using RLM-RACE ready cDNA (Ambion, Austin, Tex.) the cDNA from human and mouse brain were utilized in a nested PCR reactions with gene specific and kit primers. The 3' and 5' PCR products of both mouse and human were cut from the gel, purified and cloned into the T-Easy vector (Promega). Twenty positive colonies from each series were sequenced.

Real-Time PCR: Real-Time PCR (RT-PCR) was carried out with the GeneAmp 7900 machine (Applied Biosystems). The PCR reactions contained 20-40 ng cDNA, Universal Mastermix (Applied Biosystems), 300 nM of forward and reverse primers, and 200 nM of probe in a final reaction volume of 15 µl (primers and probe sequences are listed in Tables 1, 3). The primers and probe were designed using FileBuilder software (AppliedBiosystem). They were strand-specific for S-AS pair and the sense probes covered exon boundaries to eliminate the chance of genomic DNA amplification. The PCR conditions for all genes were as follows: 50° C. for 2 min then 95° C. for 10 min then 40 cycles of 95° C. for 15 s and 60° C. for 1 min. The results are based on cycle threshold (Ct) values. Differences between the Ct values for experimental and reference genes (18srRNA) were calculated as ΔΔCt.

Cell Culture and Transfection: SH-SY5Y cells were cultured in a mixture of MEM and F12 plus 10% FBS, 1%

NEAA, 1% L-glutamate and 1% sodium bicarbonate (culture medium). Cells in logarithmic growth were transfected with 20 nM of siRNA using 0.2% Lipofectamine 2000 according to manufacturer's instructions (Invitrogen). Cells were incubated for 48 h prior to further use. For induction of neuronal like differentiation, cells were exposed to 20 µM of retinoic acid (Sigma) for two weeks. For stress induction, cells were suspended in medium containing 30 mM KCl for 5 min or 1 µM Aβ1-42 peptide for 2 h (Tocris Co. California, USA), then were processed for fractionation as described below. For rescue experiments, cells were washed with PBS and resuspended in culture medium for 1 h at 37° C. Control samples were similarly treated and used for parallel cell fractionation and RNA extraction. Parental CHO cells and CHO-7PA2 cells were grown in DMEM containing 10% FBS. For conditioning, CHO-7PA2 cells were kept in medium without serum and supernatant media were collected 24 h later. SH-SY5Y cells were exposed to conditioned media 24 h before fractionation. Control cells were treated with the same conditioned media from parental CHO cells.

Northern Blot: Total RNA was isolated using Trizol reagent and 10 µg of total RNA was loaded per lane on a 1% agarose gel. The RNA was then transferred onto a Hybond membrane (Ambion) and blocked with Ultrahybrid (Ambion) for 6 h. The blocked membrane was hybridized overnight with radiolabeled S-AS probes spanning the overlap region of the mouse BACE-1 and BACE-1-AS. The probe was made by random priming of overlap DNA using $^{32}$P-labeled dCTP nucleotide and the Amersham random priming kit. The membrane was washed once with low stringency and twice with high stringency buffer, each for 10 minutes, and signal was detected with a phosphor-imaging instrument.

Preparation and Fractionation of Cell Extracts: Cytoplasmic extracts were prepared from SH-SY5Y cells. Cells were harvested and centrifuged at 1000g for 5 min at 4° C. Cell pellets were washed once with ice-cold PBS, pH 7.2, and lysed for 10 min on ice in three packed cell-volumes of lysis buffer (20 mM Tris-HCl, pH 7.4; 200 mM NaCl; 14 mM $MgCl_2$, 20 units suprasin and 0.1% (v/v) Triton X-100). Nuclei were isolated by centrifugation at 500g for 10 min at 4° C. The supernatant contained the cytoplasmic extract and was immediately used for RNA extraction. Nuclear extracts were prepared by washing the pellet once in lysis buffer. Nuclear RNA was then collected using RNAeasy minikit.

RNA Pull Down and Mass Spectrometry: The hypotonic fractionation buffer with high $MgCl_2$ concentration was utilized with Dounce homogenization for cell interruption. The SH-SY5Y cell lysate was immediately hybridized to strand specific biotin labeled RNA probes, for BACE-1 and BACE-1-AS, then incubated with streptavidin beads for 15 min. Purified proteins were separated using polyacrylamide gel electrophoresis (PAGE). Mass spectrometry was used for detection of proteins purified with RNA transcripts. A RNA probe targeting Prltk, with no match in the human genome, was used as a control.

Stability and α-amanitin Treatment: The HEK-293T cells plated into 24-well plates. Twenty-four h later, cells were treated with 5 µg/ml of α-amanitin and incubated with conditioned media from 7PA2 or CHO-control cells. Cells were harvested for RNA purification and RT-PCR at 6, 12, and 24 hours post treatment. Three independent samples were taken for each data point and all samples had untreated and untransfected matching samples for RNA purification and data analysis.

Statistical Analysis: All experiments were performed with 6 to 20 biological and 3-6 technical repeats. The data presented in graphs as a comparison with control-treated groups, after post-hoc test of treatment factor using main effect in two-way analysis of variance (ANOVA). The significance of each treatment was calculated as a p value and depicted in each graph, $p<0.05$ was considered significant.

RNA Fluorescent In Situ Hybridization (RNA-FISH): SH-SY5Y cells were grown on silane-coated slides overnight and fixed with 4% paraformaldehyde (pH 7.4) for 4 min. The cells were permeablized with 0.2% Triton-X for 4 min at room temperature. After air drying slides, a chamber was utilized for easy treatments of the attached cells with pre-hybridization buffer (50 formamide, 5×SCC, 50 µg/ml salmon sperm DNA and 0.1% Tween-20) at 65° C. for 1 h. The biotinylated probes for the Prltk mRNA (as a negative control) and non-overlapping parts of the BACE-1 and BACE-1-AS were produced by in vitro transcription of cloned S-AS RNA, using T7 promoter and BiotinUTP with the MEGAScript kit (Ambion). The probes then were added to the hybridization buffer (2.5 µg/ml) and incubated at 65° C. for 6 h. The slides were washed afterward, three times with PBS at 65° C., each for 10 min.

Western Blot: HEK-SW cells were transfected with 20 nM of BACE-1 sense, BACE-1-AS, or both transcripts siRNA. Cells were lysed, 48 h post transfection, with 200 µl of Laemmli sample buffer from BioRad containing 350 mM DTT. 20 µl of the cell lysate was then separated on a 10% SDS PAGE and transferred to a nitrocellulose membrane overnight. The membrane was incubated with primary antibody for BACE-1 (from Abcam) and secondary antibody conjugated to HRP. After addition of HRP substrate, the chemiluminescence signal was detected with X-ray film. The same membrane was stripped and reused for detection of β-Actin as a loading control.

ELISA and HTRF Assay: HEK-SW cells, artificially overexpressing APP Swedish mutation, were seeded on 6-well plates and transfected with 20 nM of siRNA against BACE-1 sense, BACE1-antisense, or both transcripts 24 h later. Media from the cultured cells was collected 48 h after transfection for a sandwich ELISA with Aβ1-42 antibodies. The capture antibody (mouse monoclonal for amyloid Aβ; Abcam) was incubated overnight at 4° C. in Maxisorb 96 clear plates in the presence of a carbonic buffer. The collected media was added to the plates and incubated with primary (Aβ1-42 from Abcam) and goat anti rabbit IgG secondary antibody. Luminescence was detected, after addition of HRP substrate, using SpectraMax plate reader. Average absorbance of three repeats at 405 nm were subtracted from background and normalized to negative control siRNA sample. A Time Resolved Fluorescence (HTRF) assay (Cisbio) was utilized for Aβ 1-42 detection. Two specific monoclonal antibodies against Aβ 1-42 were tagged to flurophores and upon binding to the Aβ peptide simultaneously, and based on distance between them, emission of the first one will excite the second. HTRF reaction was performed, following product protocol, in a single tube, using purified protein from APPtg and wildtype mice, without any washing steps which allowed direct measurement of the peptide.

Animal Studies: After IACUC approval for animal studies at The Scripps Research Institute, 18 six-month old male mice were used for in vivo experiments. The mice were divided in three groups of six and osmotic mini-pumps (Alzet) were surgically implanted with chronic indwelling cannulae in the dorsal third ventricle. The osmotic mini-pumps delivered continuous infusions (0.25 µl/h) of siRNA directed against BACE-1 (group 1), BACE-1-AS (group 2) or control siRNA (previously known to be ineffective across human and mouse genes; group 3) at a dose of 0.4 mg/day. After 14 days of continuous siRNA infusion, mice were euthanized and the brains removed. Five tissues from each mouse were excised for RNA quantitative measurement; dorsal hippocampus, ventral hippocampus, dorso-medial prefrontal cortex, dorsal striatum and cerebellum. Tissues were excised, rinsed in ice cold PBS and RNA was extracted after homogenization in Trizol reagent (Invitrogen) according to the manufacturer's protocol. The extracted RNA samples were passed through Qiagen RNeasy columns and subjected to on-column DNAse treatment for removal of DNA contamination. The concentration of RNA samples was determined spectrophotometrically and 800 ng of each sample was used for the first strand cDNA synthesis, in a final volume of using random hexamers and reverse transcriptase (Applied Biosystems). Real-time PCR (RT-PCR) measurements were carried out as described above. The percentile changes in RNA levels, for individual tissues compared to control mice, were plotted in each graph.

In a separate set of experiments, four APP-tg mice (Tg 19959) and four control littermate all male 6 w/o were sacrificed. Brain tissues were used for RNA measurements and $A\beta$ 1-42 detection by HTRF.

Identification of a BACE-1 Non-Coding Natural Antisense Transcript: The genomic organization of the human BACE-1 locus is illustrated in FIG. 12A. The position of our primers, probes and siRNA sequences are depicted in FIG. 12B, also listed in Table 5. The BACE-1-AS transcript is highly conserved across species (see FIG. 12B).

Sequence information for human BACE-1 (NM_012104), mouse BACE-1 (NM_011792), human BACE-1-AS (CB960709), and mouse BACE-1-AS (AK074428 and AK078885) was retrieved from the UCSC Genome Bioinformatics web site (genome.ucsc.edu/cgi-bin/hgGateway). To fully characterize the genomic organization of BACE-1-AS, we performed rapid amplification of cDNA ends (RACE) experiments for directional sequencing of NAT from 5' and 3' ends. For the human BACE-1-AS, RACE revealed a sequence almost identical to the expressed sequence tag (EST) from the UCSC database (CB960709), except for additional nucleotides in its boundaries as depicted in FIG. 12C. Two splice variants for human and mouse BACE-1-AS were identified that overlap with the BACE-1 sense transcript in both species. Two separate ESTs for the mouse BACE-1-AS were also found that corresponded to a single contiguous sequence, covering exon 5 and 6 of the mouse BACE-1 gene (FIG. 12D). A poly-A tail and cap structure were found for both human and mouse antisense sequences, suggesting that BACE-1-AS is a product of RNA polymerase II, and is a fully processed RNA transcript. However, there was no open-reading frame, suggesting that BACE-1-AS is a ncRNA. Also, several mismatches with the genomic sequence were detected in both human and mouse BACE-1-AS, implying "A to I" editing was likely due to nuclear duplex formation with the sense transcript (Kawahara and Nishikura, 2006 *FEBS Lett* 580, 2301-2305). This latter finding may relate to the nuclear retention pattern of BACE-1-AS as described in detail below. All the new sequences of human and mouse BACE-1-AS are also shown in the supplementary data section.

Figure 10A:
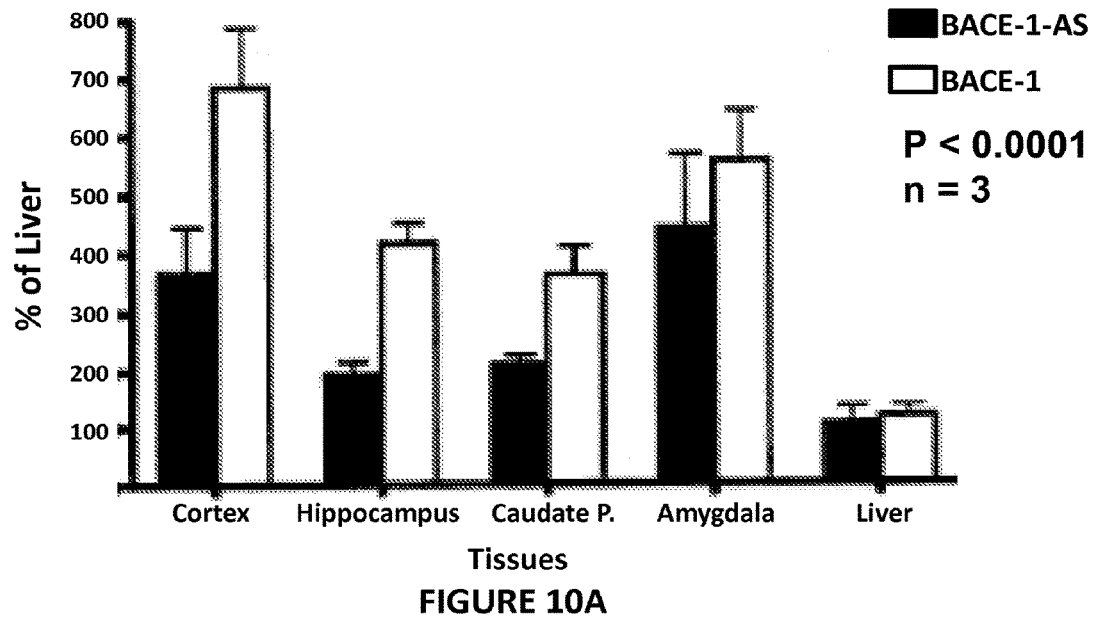
FIGS. 10A-10B are graphs showing the expression profile of the BACE-1 and BACE-1-AS in various regions of the mouse brain and liver. Both transcripts were 2-5 times more abundant in various regions of the brain compared with liver. The cerebral cortex and amygdala showed the highest expression of both transcripts among brain regions sampled (FIG. 10A). Northern blot analysis confirmed expression of BACE-1 and BACE-1-AS in mouse brain tissues (FIG. 10B). BACE-1 and BACE-1-AS transcripts were also expressed in undifferentiated and differentiated human neuroblastoma SH-SY5Y cells. Induction of differentiation of human neuroblastoma SH-SY5Y cells was associated with a reduction of BACE-1-AS transcript expression by about 50% and the BACE-1 transcript by about 20% (FIG. 10B), suggesting that the expression of both the sense and NAT transcripts are concordant.
Figure 10B:
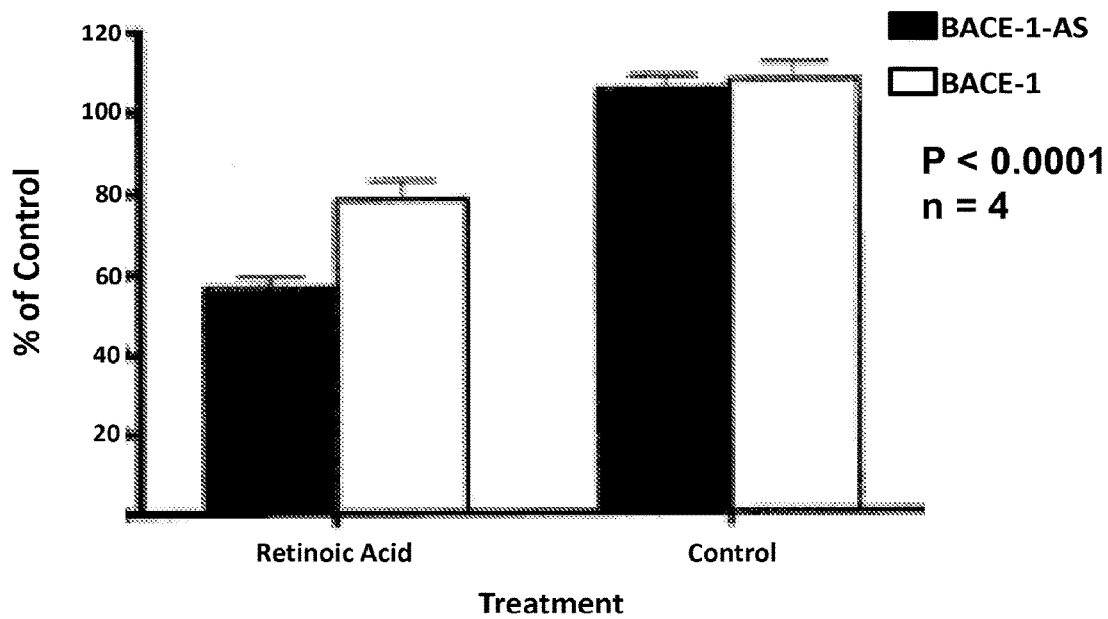

Expression Profiling: Using RT-PCR, we measured the relative expression of the BACE-1 (sense) and BACE-1-AS (antisense) RNA transcripts in various regions of the mouse brain and liver. Both transcripts were 2-5 times more abundant in various regions of the brain compared with liver. The cerebral cortex and amygdala showed the highest expression of both transcripts among brain regions sampled (FIG. 10A). Northern blot analysis confirmed expression of BACE-1 and BACE-1-AS in mouse brain tissues (FIG. 10C). BACE-1 and BACE-1-AS transcripts were also expressed in undifferentiated and differentiated human neuroblastoma SH-SY5Y cells. Induction of differentiation of human neuroblastoma SH-SY5Y cells was associated with a reduction of BACE-1-AS transcript expression by about 50% and the BACE-1 transcript by about 20% (FIG. 10B), suggesting that the expression of both the sense and NAT transcripts are concordant.

Figure 13A:
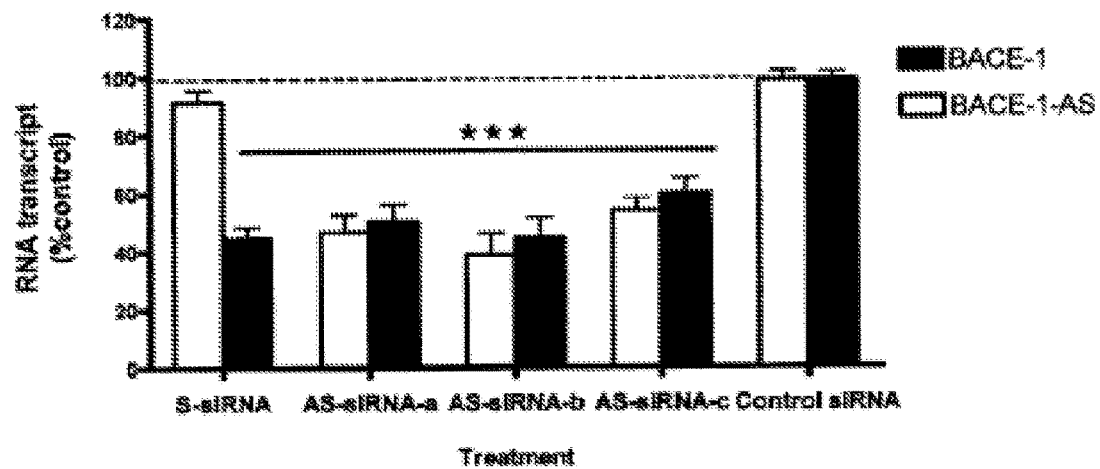
FIGS. 13A and 13B are graphs showing the silencing of BACE-1 and BACE-1-AS transcripts with synthetic siRNA.

BACE-1-AS Knockdown Concordantly Reduced BACE-1 Sense Transcript In Vitro: We next investigated the role of BACE-1-AS in regulating the expression of its sense partner (BACE-1 mRNA) via siRNA knockdown. FIG. 13A shows three distinct siRNA sequences that knocked down the BACE-1-AS transcript by ~60% in human SH-SY5Y cells. All three of the siRNA sequences target the antisense transcript (but not BACE-1 mRNA), were also highly effective in concordantly and concomitantly knocking down the sense transcript to a similar degree as the antisense transcript. Since three distinct siRNA molecules that target the antisense transcript (BACE-1-AS) resulted in the concordant knockdown of BACE-1 it is unlikely that the siRNAs indirectly knocked down BACE-1 transcript through a non-specific (or "off-target") mechanism. We therefore suggest that in human SH-SY5Y neuroblastoma cells, the non-coding antisense transcript exerts a regulatory action on the expression of BACE-1 mRNA, and that it is possible to affect the expression of BACE-1 by knocking down BACE-1-AS without targeting the BACE-1 transcript itself.

The effects of knocking down BACE-1 mRNA were also assessed. FIG. 13A shows a sense-targeting siRNA (S-a) that knocked down BACE-1 mRNA by 70% in SH-SY5Y cells. Two other siRNA sequences targeting BACE-1 mRNA, S-b and S-c (shown in FIG. 12B), similarly knocked down BACE-1 mRNA. S-a targets a non-BACE-1-AS-overlapping portion of the BACE-1 sense transcript, and did not alter the expression of the BACE-1-AS 48 h after siRNA application. Thus, in SH-SY5Y cells, knockdown of BACE-1 mRNA does not modulate the expression of BACE-1-AS.

Figure 11A:
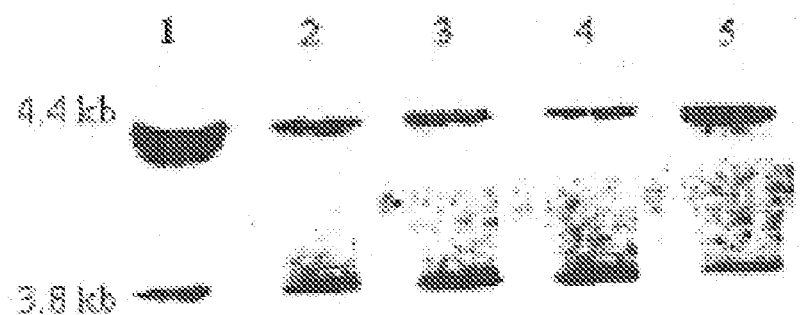
FIGS. 11A and 11B are scans of Western blots of the BACE-1 protein after treatment of SH-SY5Y cells with siRNA. BACE-1 protein in control cells (lane-1) compared to cells transfected with 20 nM of siRNA against BACE-1 (lane-2), BACE-1-AS (lane-3), or both transcripts (lane-4).
Figure 11B:
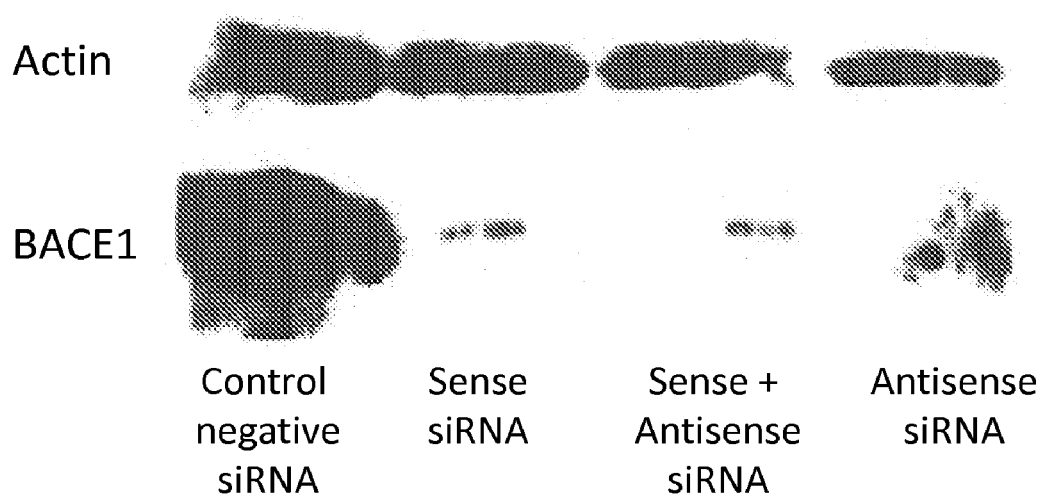
Figure 13B:
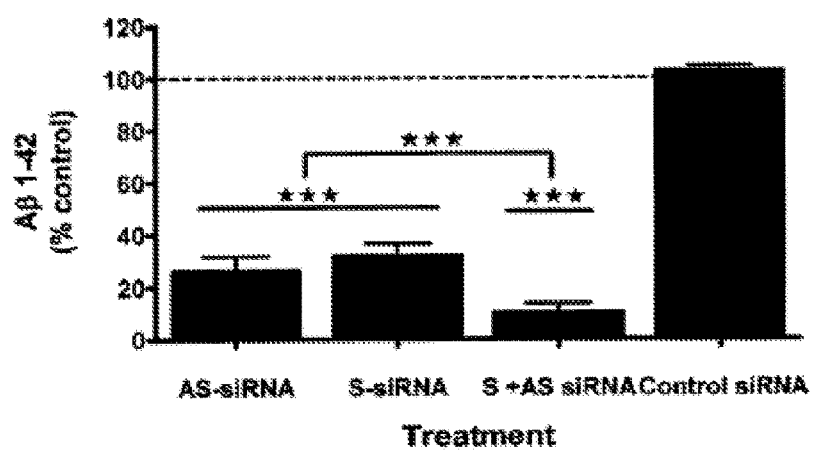

Knockdown of BACE-1-AS Reduced BACE-1 Protein and $A\beta$ 1-42 Production: The concordant effect of knocking down BACE-1-AS on BACE-1 mRNA expression was not restricted to the mRNA level, since BACE-1 protein level was also reduced upon administration of NAT specific siRNA, as determined by Western blot (FIG. 11). Furthermore, we used ELISA approach to measure the levels of $A\beta$ 1-42 following siRNA treatment. $A\beta$ 1-42 is a product of enzymatic cleavage of APP by BACE-1, and it is detectable in the HEK-SW cell line that contains APP with the so called Swedish mutation. Levels of $A\beta$ 1-42 were markedly reduced upon treatment of the HEK-SW cell line with siRNA against BACE-1-AS (FIG. 13B).

Combined Targeting of BACE-1 Sense and Antisense Transcripts Showed a Synergistic Effect: We next asked whether synergy could be achieved by simultaneous targeting of BACE1 and BACE-1-AS transcripts in HEK-SW cells. Simultaneous application of siRNA directed to BACE-1 sense as well as antisense transcripts reduced $A\beta$ peptides by a greater magnitude than that induced by knockdown of either sense or antisense transcript alone (P<0.001), see FIG. 13B. This observation raises the possibility that some or many siRNA molecules may have inadvertently been designed such that they target cis-sense/antisense pairs simultaneously. For example, it was recently shown that targeting BACE-1 with siRNA in vivo ameliorates AD-like neuropathology and behavioral deficits in APP transgenic mice (Singer et al., (2005). Nat Neurosci 8, 1343-1349). The most potent siRNA molecule in their study targeted the overlapping region of the BACE-1 sense/antisense locus, raising the possibility that knockdown of both the sense and antisense BACE-1 transcripts contributed to the overall efficacy.

In Vivo Administration of siRNA Targeting BACE-1 Sense or Antisense Transcripts:

The above observations demonstrate that disruption of BACE-1-AS results in down regulation of BACE-1 mRNA in vitro. Next, we assessed whether the same relationship exists in vivo in mice brains. To address this question, mice were prepared with chronic indwelling cannulae in the dorsal third ventricle. Mice were also implanted subcutaneously with osmotic mini-pumps that delivered continuous infusions (0.25 µl/h) of siRNA directed against BACE-1 (group 1), BACE-1-AS (group 2) or control siRNA (previously known to be ineffective across human and mouse genes; group 3) at a dose of 0.4 mg/day for two weeks (Thakker et al., (2004). Proc Natl Acad Sci USA 101, 17270-17275.; Thakker, D. R., et al. (2005). Mol Psychiatry 10, 782-789, 714). Tubing was connected to the exit port of the osmotic mini pump and tunneled subcutaneously to the indwelling cannula, such that siRNAs were delivered directly into the brain. After 14 days of continuous siRNA infusion, mice were euthanized and the brains removed. The expression levels of BACE-1 and BACE-1-AS were assessed in the dorsal hippocampus, ventral hippocampus, dorso-medial prefrontal cortex, and dorsal stratum.

Figure 14A:
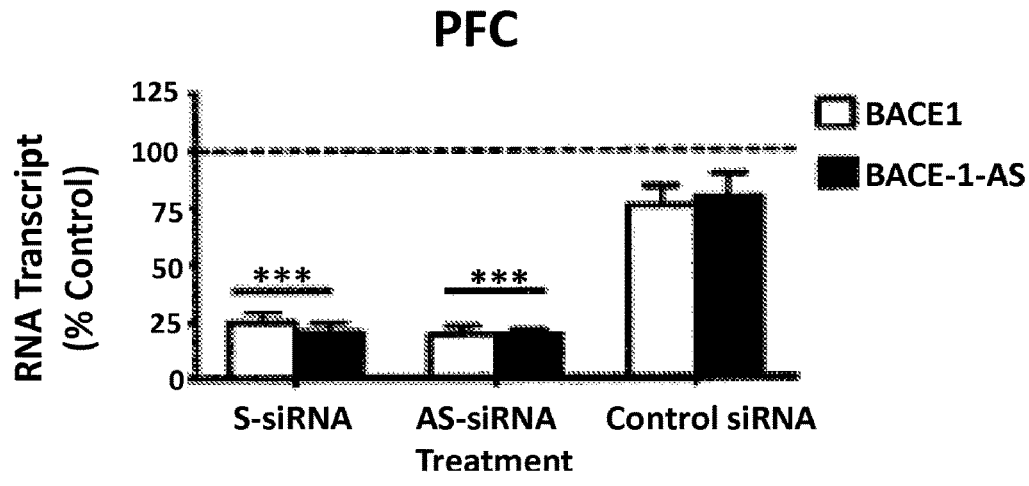
FIGS. 14A-14E are graphs showing in vivo infusion of synthetic unmodified siRNA into the mice brain. The synthetic unmodified siRNA were designed to target non-overlapping region of either BACE-1 (sense), BACE-1-AS for degradation. The control siRNA had similar properties and previously were shown to be ineffective against human and mouse genes. Three groups of the mice were subjected to constant infusion of the siRNA over the period of two weeks. Five tissues from each mouse were used for RNA quantitative measurement by real time PCR.
Figure 14B:
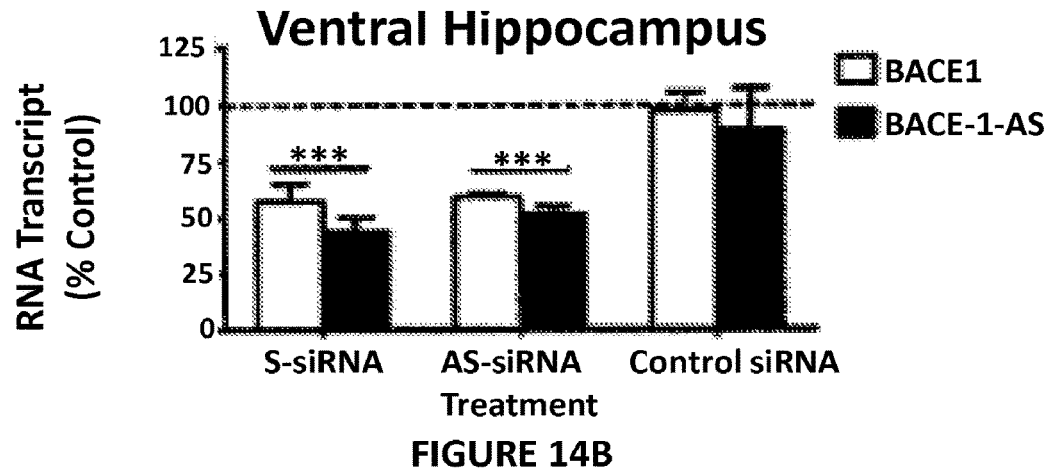
Figure 14C:
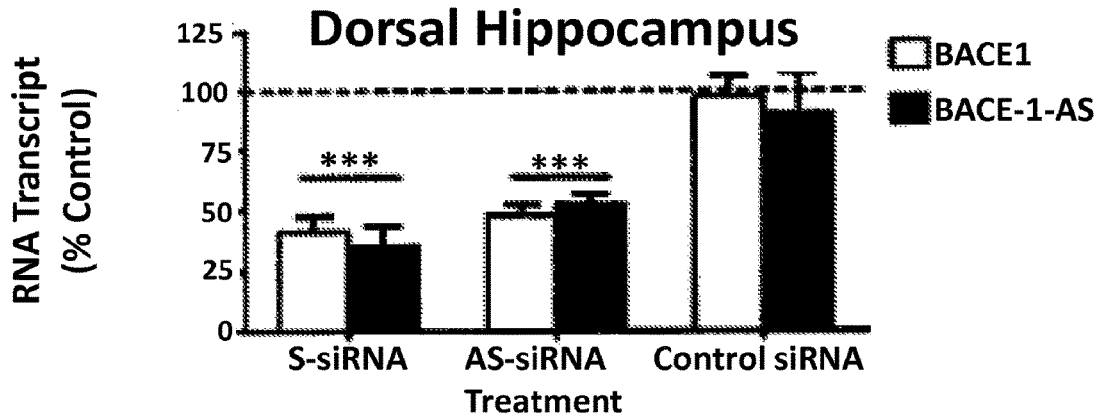
Figure 14D:
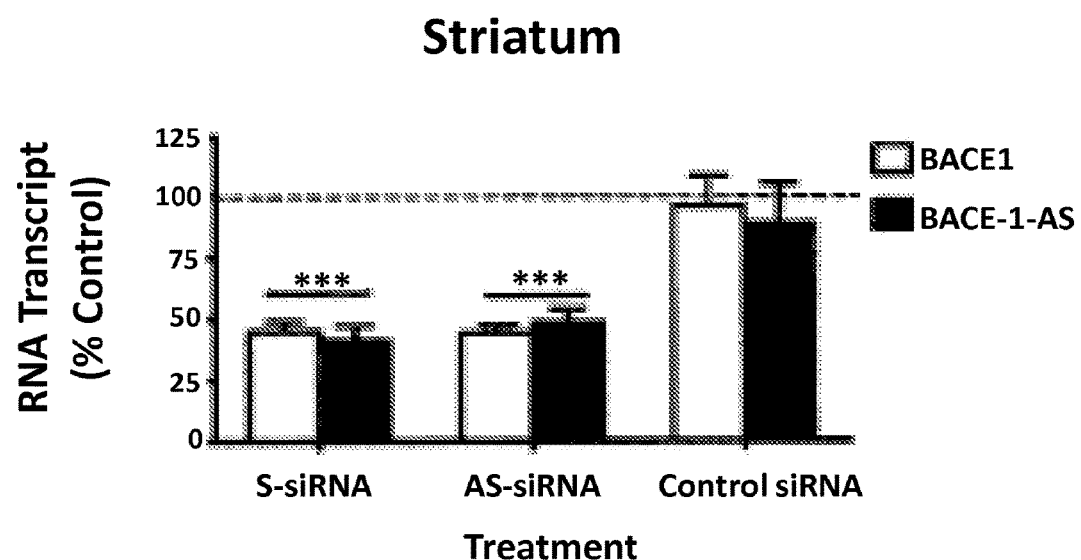
Figure 14E:
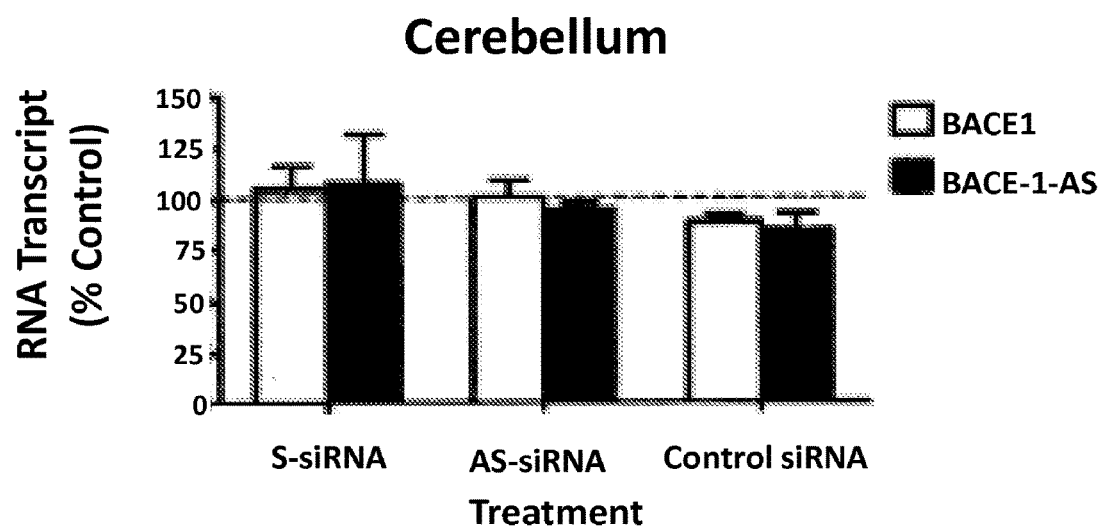

Notably, BACE-1 concentrations were reduced in all four brain regions upon administration of siRNA selectively directed against either BACE-1 or BACE-1-AS (FIGS. 14A-14D). siRNAs directed against either the sense or antisense transcript resulted in a concomitant decrease of both BACE-1 and BACE-1-AS levels compared with control treated groups. Additionally, we measured S-AS transcripts in cerebellum (FIG. 14E) as a control tissue and found that the level of BACE-1 and BACE-1-AS was unchanged, an expected result for a tissue that is not directly bathed in the cerebrospinal fluid of the third ventricle. Collectively, these in vivo findings replicate our in vitro observations which suggest a concordant regulation of BACE-1 mRNA by BACE-1-AS.

Figure 15A:
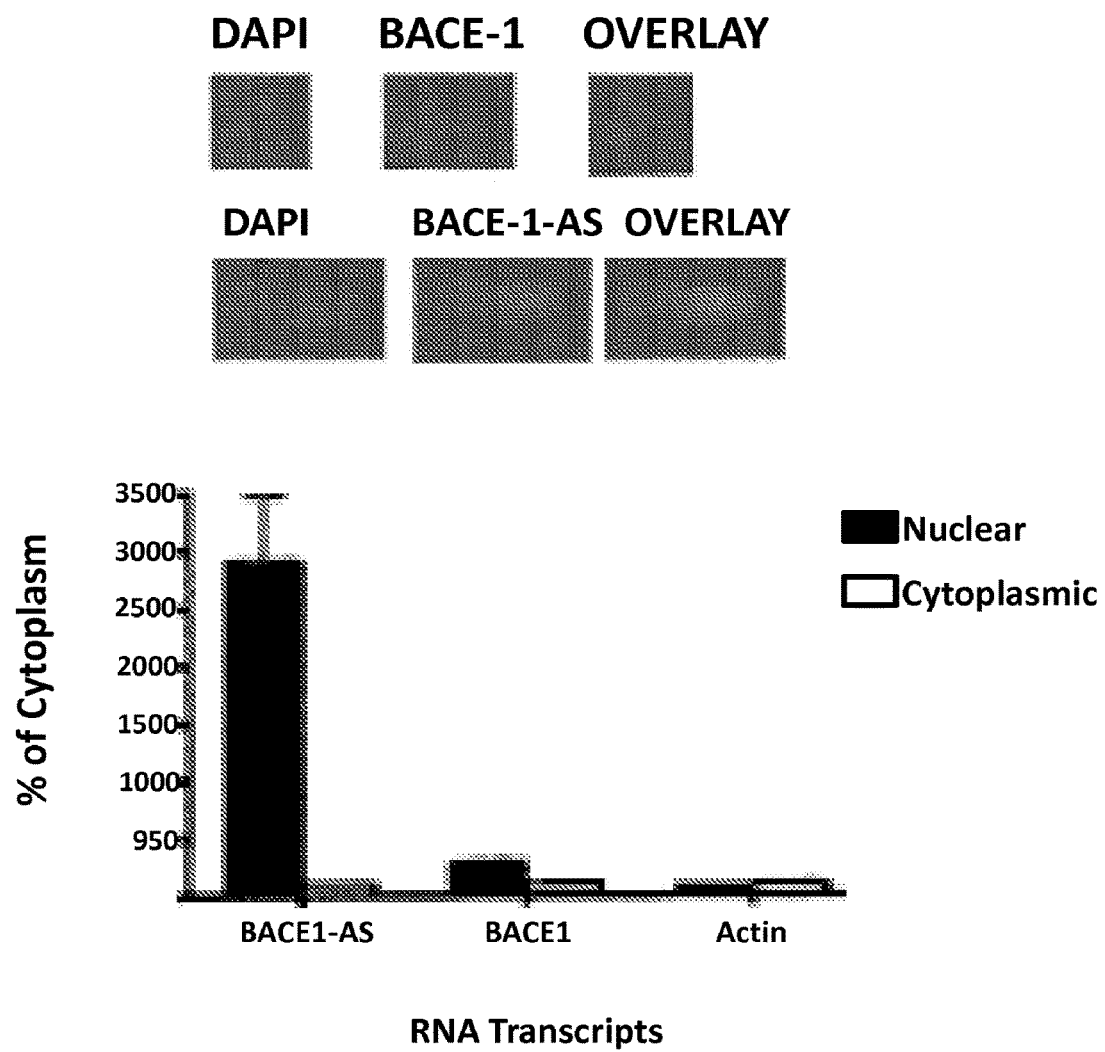
FIGS. 15A-15F show stress induced relocation of antisense transcript.

BACE-1-AS Transcript is Accumulated in the Cell Nucleus: To examine the cellular distribution of BACE-1 and BACE-1-AS, we separated lysates of SH-SY5Y cells into cytoplasm and nuclear fractions and extracted RNA for RT-PCR analyses. BACE-1-AS was enriched in the nuclear fraction compared with the cytoplasmic fraction (FIG. 15A). Nuclear retention of BACE-1-AS was confirmed by RNA fluorescent in situ hybridization (RNA-FISH) images of SH-SY5Y cells (FIG. 15A-15D inset). BACE-1-AS is approximately 30 times more abundant in the nucleus than the cytoplasm, whereas BACE-1 sense transcript (and β-Actin mRNA control) was distributed about equally between the nucleus and cytoplasm.

We also designed a RNA-FISH experiment using multi-color florescent probes to visualize the sub-cellular localization of the sense and antisense transcripts. Exposure of the cells to stressors, resulted in translocation in BACE-1-AS FISH signals. (FIG. 15A-15D inset). We utilized RNA probe that originates from Prltk luciferase, with no match in the human genome, as a negative control probe. As seen from the microscope images in FIG. 15A, the antisense transcript BACE-1-AS was predominately detectable in the nucleus. By contrast, sense BACE-1 transcript was more diffusely distributed throughout the cell.

Profiling RNA-Protein Interactions with Mass Spectrometry: To identify proteins that might be involved in nuclear retention and/or transport of the non-coding antisense transcript, we pulled out RNA and profiled the RNA interacting proteins. The high $MgCl_2$ and non-denaturing nature of the method facilitated the maintenance of RNA-protein interactions during experimental manipulations. Table-4 lists proteins that associate with BACE-1 and BACE-1-AS transcripts. Proteins involved in translation processes co-purified selectively with the BACE-1 mRNA. In contrast, proteins with a high nuclear abundance associated with the BACE-1-AS transcript. These findings are in agreement with non-coding nature of the antisense transcript and support the concept of its nuclear retention.

Cyclophilin-60 (Cyp60) and BACE-1-AS: Little is currently known about the mechanisms by which the expression and function of BACE-1 is regulated. However, a recent large scale siRNA screening effort revealed that Cyp60 knockdown reduces BACE-1 mRNA and protein levels (Espeseth et al., (2006) Mol. Cell Neurosci. 33, 227-235). Cyclophilin-60 (Cyp60) is a member of the cyclophilin family of peptidylprolyl isomerases. The cyclophilins make up a highly conserved protein family, members of which play an important role in protein folding, immunosuppression by cyclosporin A, and infection of HIV-1 virions. Cyp60 protein interacts with the proteinase inhibitor eglin c and is localized in the nucleus. Cyp60 has also been reported to be involved in cell surface expression of CD147 (also known as extracellular matrix metalloproteinase inducer), suggesting that Cyp60 plays a role in the translocation of CD147 to the cell surface.

Figure 16A:
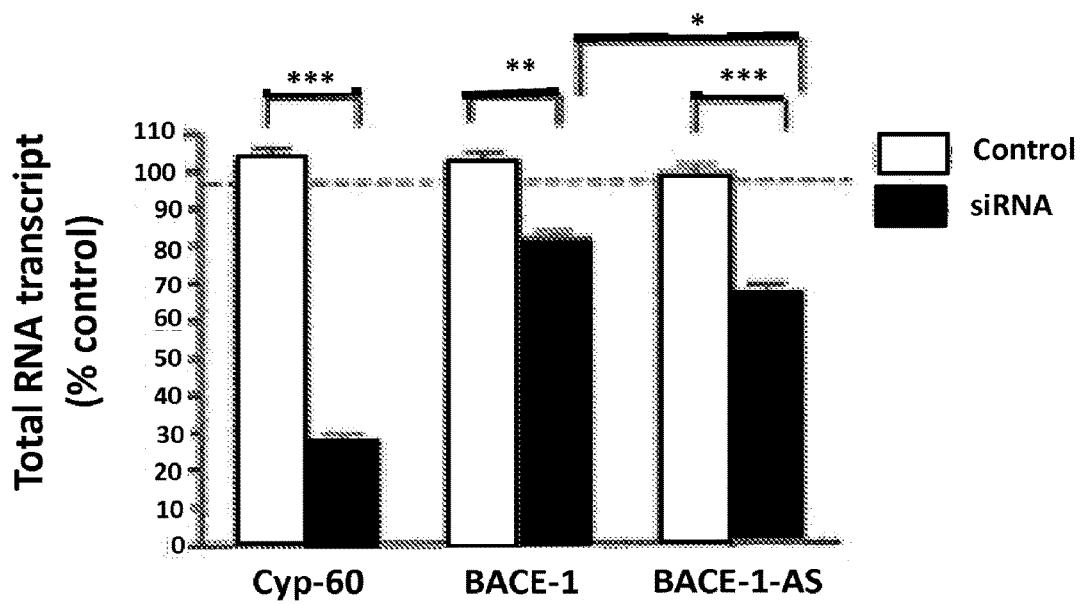
Figure 16B:
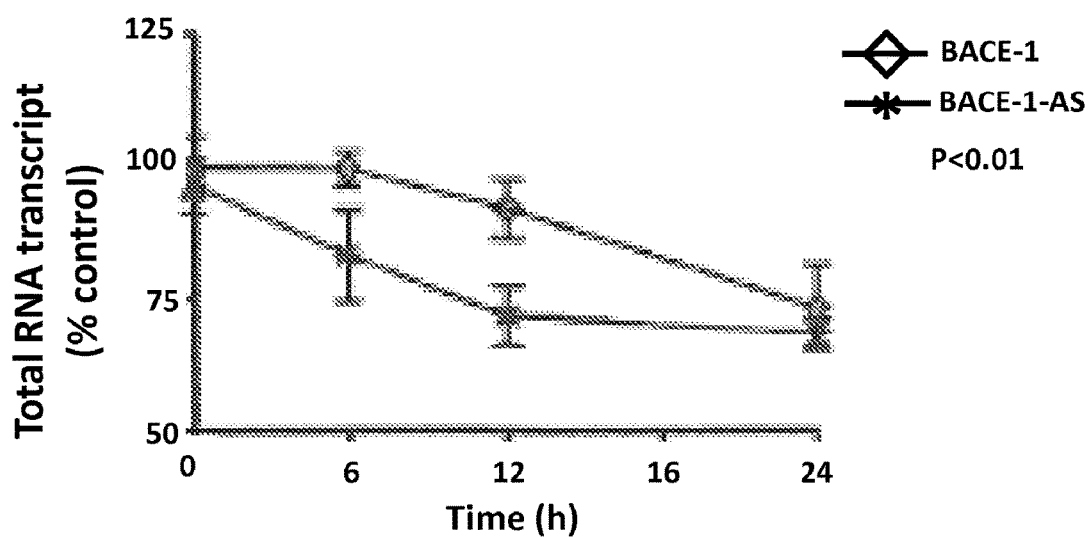
Figure 16C:
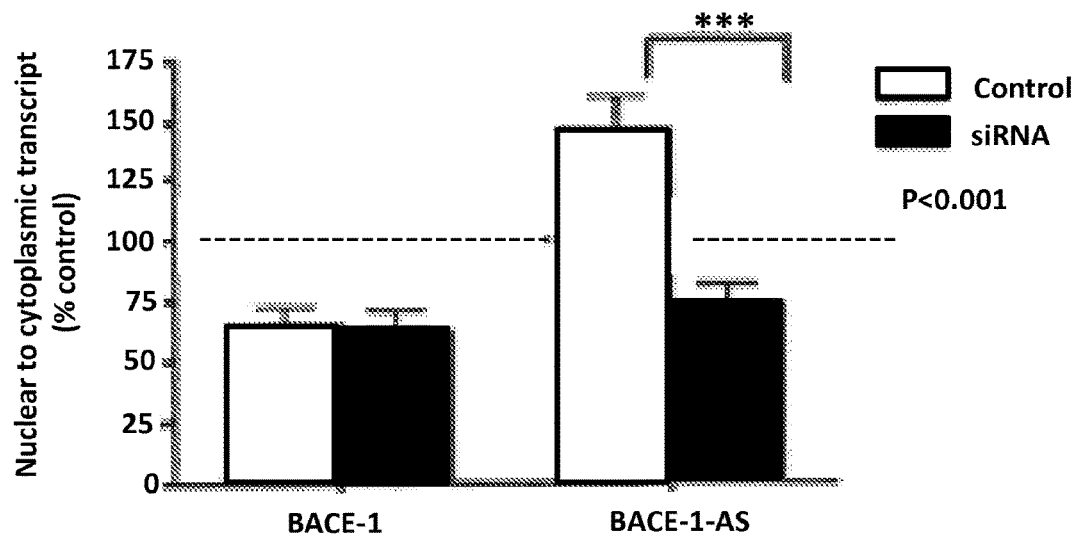

Given the proposed role for BACE-1-AS in regulating BACE-1 expression, and the previously published observation that Cyp60 regulates BACE-1 mRNA expression, we hypothesized that Cyp60 may also play a role in regulating BACE-1-AS. To test this hypothesis, we examined the effects of knocking down Cyp60 on BACE-1 and BACE-1-AS expression. First, we confirmed a role for Cyp60 in regulating BACE-1 mRNA expression by demonstrating that siRNA-mediated knockdown of Cyp60 reduced BACE-1 mRNA levels in human embryonic kidney cells (HEK293T). However, the BACE-1-AS transcript was also reduced by Cyp60 siRNA exposure (FIG. 16A). When compared to the Cyp60 knockdown-induced reduction of BACE1 mRNA, the magnitude of the BACE-1-AS transcript reduction was greater, and occurred at an earlier time point (FIG. 16B). Since Cyp60 is retained almost exclusively in the nucleus (Wang et al., (1996) Biochem J. 314 (Pt 1), 313-319), where the BACE-1-AS is also localized, suggests that Cyp60 may act preferentially on BACE-1-AS to modulate the expression of BACE-1 mRNA. Consistent with this hypothesis, Cyp60 knockdown significantly altered the nuclear retention pattern of BACE-1-AS transcript (FIG. 16C).

Human BACE-1-AS sequences shown here are based on the 5', 3' RACE cloning and sequencing results and compared to EST sequence from UCSC (cDNA CB960709).

Human BACE-1-AS main variant (10 clones) SEQ ID NO: 64:
TCTAGCGAGGTGACAGCGTAGAACCAG

GCGGGGTCCCTCCCATTACATACTACTGCTCTGGCCTCTGCCCGTCATAG

TTGCCATCTGGTCATTTCCTTCCCATAAAGCCAGGGCTCACCGCAACCTC

CACCGTCCTGAGTTAAAGTGATTCTCCTGTCTCAGCCCCTGAGTAGCTA

GGATTACAGGCGTGCGCCACCACACCCAGCTAATTTTTGTACTTTTAGTA

GAGATGGGATTTCACCCTGTTGGTCAGGCTGGTCTTGAACTCCTGACCTA

GTGATCTGCCCACCTTGGCCTCCCAAAGTGCTGGGATTACAGGCGTGAGC

CACCACGCCTGGCTAGGGGAAGAGTGC(t)TTTAAGAGCTCTGAGTAGAA

GGGTCTAAGTGCAGACATCTTGGCTGTTGCTGAAGAATGTGACTCTCACC

GCCTCCCTCTGACACTGTACCATCTCTTTTACCCCCATCCTTAGTCCACT

CACGGAGGAGGCTGCCTTGATGGATTTGACTA(g)CAGCTTCAAACACTT

TCTTGGGCAAACGAAGGTTGGTGGTGCCACTGTCCACAATGCTCTTGTCA

TAGTTGTACTAAGAGGGAAAAGAGAGAGTTAAAAGAGTCAAAAGGTTTTT

GATGCTGGGCTCTGGGCAGTAGGGGGTTACTGCTGGGGCCCCAGCTGGGT

TGGCATCTTGGCTTTGGCACCTCCTAAGTGTACCTGCTTGGACAAGTTAA

CCTCTGTGCCTCAGTTCCTTCATCTCTAAAGTGAGGATAAAAATAGCACC

TACCTCAAAGGGTTATTGTAAGGATTAAATAAATCAGCAATGTAAAGCAC

TTAGAATCGTGCCCAGCAGAGAGAAGGCACTTGGTAAATGTTTATTCTTG

TTAATCTTGGGTGGGCAGGTAGTCTCCAAACTTGAAAAAAAAAAAA

AGCACCTTATAAATCGTGCCCCGCCAGAAGAGAAAGGGCACTTTGGGAAA

AATGGTTTTAATTCCCTTGTTTAAATTCTTTGGGGGTGGGGGGCCAAGGT

TAAGTTTCTTCCCCAAAAACCTTTGGAAAAAAATT

Human BACE-1-AS short variant (6 clones) SEQ ID
NO: 65:
C(t)TTTAAGAGCTCTGAGTAGAAAGGGTCTAAGTGCAGACATCTTGGCTG

TTGCTGAAGAATGTGACTCTCACCGCCTCCCTCTGACACTGTACCATCTC

TTTTACCCCCATCCTTAGTCCACTCC(a)C

GGAGGAGGCTGCCTTGATGGATTTGACTGCAGCTTCAAACACTTTCTTGG

GCAAACGAAGGTTGGTGGTGCCACTGTCCACAATGCC(t)CTTGTCATAG

TTGTACTAAGAGGGAAAAAAAAAAA

Mouse BACE1-AS sequences shown here, are based on the 3′ RACE cloning and sequencing results and they compared EST sequences from UCSC (cDNA AK077428.1 and cDNA AK078885.1).

Mouse BACE-1-AS main variant (10 clones) SEQ ID
NO: 66:
GTCTACGGATCAGGAGGAGAAAGTGAGATACTGGCCTCATAAAGCTGTGA

GTGGGCATGGTGGCTCACACTGCCTGTGGTCCCAGAACTTAGAAGGCTAA

GGCATGAAGTTGTCAAGTTCAATGCTAACCTGGGCTACGTTCATGACCCC

ATCTCAAAAAAAAAAAAAAAAAAAAAAAGGCATCTCAATGCCAAGTCAA

CAGAGCAGTGGTTTGTAAGCGCCTGATGGAAGGATCTACGTATCTTTAG

GGCTTGCTGAGGAGTGTGACTGTCACTGACCGAGGAGGCTGCCTTGATGG

ACTTGACGGCAGCTTCAAATACTTTCTTGGGCAAGCGAAGGTTGGTGGTC

CCACTGTCCACAATGCTCTTGTCGTAGTTGTACTGAGGAGAGAGGGGGGG

AGAGGTGGAGGGGTGAATCTGACAGCTAAGCATCCTACTGGGGTTGGCA

TCTTAGCTTTCCCATTTTGTATATGTGCGTCCTTGGGCACGTTGCTTAAC

CTCTGTGTACCTGTTCTCTTGTTCTAAATTGAAGATAATAACAGTGCCTA

CCTCAAAGGTTACCATAAGGATTACATAGGTCAAAAGGCTGAAAGCACTA

AGTAGGTCCTGGCAGATCCCAGGCACTTGGTAAGTACTAACTTCGTCACC

TTGTGCGGGTAGGTGTTCTCTAAATCTAAAGCAGAAATGCCTTGTGTGGT

ATTTGTAACTTCTAGTACTTTTATGTAGTTATTCTCATTCACCATACATT

ATAATGGAGAGAAGGGTGGCTCAGCACGCACAAAGCCATGAGCTTGAGCT

CTGATGCTGCATGGTGGTATATGCCTGTAGAGAGACACTTGAGAGTCAGA

GAAAGGAGGACCAGGAGTTCAAGGTCATCTTTAGCTACCTAGCAAGTCTG

AGGTCAGCGTGGGCTACATAAGATCCTCAAAAAAGCCAAAAAAGGGGGCT

GTTGAGATAGGTAAGGGCACCTGCTACCAAGTCTGATGACCTGAGTTCAA

CCCCAGAGAGACCTACTAGTTACTGAAAATTGTCCTCTAACCTCCATACA

CAAGCTGTGGCACATGCCCCATCCTCATCCCAATAAATGTAAAACAAAAT

CTAGGGAAAGAGACCCTAAGTGTTGGCATTTGGGTATGCCAAGCATAACG

ACTAACACTTCATACATTGGCTTTGACCTTTACAGTCTGTGAGAACGCTT

GTGTATTTCTACCTCTGCCTTGTAGATGAGGAGTCTGGCACTGTAGTGAG

GAGCCTGAGGGCACTTAGTAACAGCAGGACTCTAGTCAGGTCCAACCTCT

GCCTCACAAAAGCCTTGCCCAAGGCTGAAGAGGCAGTGACTAGAGTCCAG

AAAGGAACTCTTTCATGTTTTCATTACTATACTTAAGTCATGTGGTCCAG

GCTCTGTGACTGCTCTGCCAGGCCCCGCCCTTCACCTTAGGGATTGCCTC

GTGATCCTGTGCTTCCACCCTCATGGCTCTCACACACTGTGAGACTCCCC

TTATGCTCACGAGAATCCCCTCCATCCCATTACCTCCTTGCAGTCCATCT

TGAGATCTTGACCATTGATTTCCACACGTACAATGATCACTTCATAATAC

CACTCCCGCCGGATGGGTGTGTACCAGAGACTGCCCGTGTATAGCGAGTG

GTCGATACCACCAATGATCTAAAAGAAAAAAAA

Mouse BACE-1-AS long variant (2 clones) SEQ ID
NO: 67:
GTCTACGGATCAGGAGGAGAAAGTGAGATACTGGCCTCATAAAGCTGTGA

GTGGGCATGGTGGCTCACACTGCCTGTGGTCCCAGAACTTAGAAGGCTAA

GGCATGAAGTTGTCAAGTTCAATGCTAACCTGGGCTACGTTCATGACCCC

ATCTCAAAAAAAAAAAAAAAAAAAAAAAGGCATCTCAATGCCAAGTCAA

CAGAGCAGTGGTTTGTAAGCGCCTGATGGAAGGATCTACGTATCTTTAG

GGCTTGCTGAGGAGTGTGACTGTCACTGACCGAGGAGGCTGCCTTGATGG

ACTTGACGGCAGCTTCAAATACTTTCTTGGGCAAGCGAAGGTTGGTGGTC

CCACTGTCCACAATGCTCTTGTCGTAGTTGTACTGAGGAGAGAGGGGGGG

AGAGGTGGAGGGGTGAATCTGACAGCTAAGCATCCTACTGGGGTTGGCA

TCTTAGCTTTCCCATTTTGTATATGTGCGTCCTTGGGCACGTTGCTTAAC

CTCTGTGTACCTGTTCTCTTGTTCTAAATTGAAGATAATAACAGTGCCTA

CCTCAAAGGTTACCATAAGGATTACATAGGTCAAAAGGCTGAAAGCACTA

AGTAGGTCCTGGCAGATCCCAGGCACTTGGTAAGTACTAACTTCGTCACC

TTGTGCGGGTAGGTGTTCTCTAAATCTAAAGCAGAAATGCCTTGTGTGGT

```
-continued
ATTTGTAACTTCTAGTACTTTTATGTAGTTATTCTCATTCACCATACATT

ATAATGGAGAGAAGGGTGGCTCAGCACGCACAAAGCCATGAGCTTGAGCT

CTGATGCTGCATGGTGGTATATGCCTGTAGAGAGACACTTGAGAGTCAGA

GAAAGGAGGACCAGGAGTTCAAGGTCATCTTTAGCTACCTAGCAAGTCTG

AGGTCAGCGTGGGCTACATAAGATCCTCAAAAAAGCCAAAAAAGGGGGCT

GTTGAGATAGGTAAGGGCACCTGCTACCAAGTCTGATGACCTGAGTTCAA

CCCCAGAGAGACCTACTAGTTACTGAAAATTGTCCTCTAACCTCCATACA

CAAGCTGTGGCACATGCCCCATCCTCATCCCAATAAATGTAAAACAAAAT

CTAGGGAAAGAGACCCTAAGTGTTGGCATTTGGGTATGCCAAGCATAACG

ACTAACACTTCATACATTGGCTTTGACCTTTACAGTCTGTGAGAACGCTT

GTGTATTTCTACCTCTGCCTTGTAGATGAGGAGTCTGGCACTGTAGTGAG

GAGCCTGAGGGCACTC(t)AGTAACAGCAGGACTCTAGTCAGGTCCACC

TCTGCCTCACAAAAGCCTTGCCCAAGGCTGAAGAGGCAGTGACTAGAGTC

CAGAAAGGAACTCTTTCATGTTTTCATTACTATACTTAAGTCATGTGGTC

CAGGCTCTGTGACTGCTCTGCCAGGCCCCGCCCTTCACCTTAGGGATTGC

CTCGTGATCCTGTGCTTCCACCCTCATGGCTCTCACACACTGTGAGACTC

CCCTTATGCTCACGAGAATCCCCTCCATCCCATTACCTCCTTGCAGTCCA

TCTTGAGATCTTGACCATTGATTTCCACACGTACAATGATCACTTCATAA

TACCACTCCCGCCGGAG(t)GGGTGTGTACCAGAGACTGCCCGTGTATAG

CGAGTGGTCGATACCACCAATGATCTAAAAGAAAAAGAGACAGACACCTA

TGTCCTAGCACAGAAGGAGAGCAAGTTACCCAAGACTAAATAATAAGATC

AGCCATTTCTTGGGGTGCCAAGATTCTCTCTAATCTCCCATCATGCCCCA

TGCATGGTAATATTTAGTTTCCTAAATGTGTTCAGGAGAAGAAACACATC

GGGATTATTTGTATCAAAATCTATAGCCCTTGACCGAAAGTTATTTAAGC

CC(t)AAGCTAGTACAATAAACGTGGAATGAACTGATTGTATGCTGCTTT

CATACATTTTCTTGTCTTTGCTTGTTGGAGAATACTTGTTACTGTCCTAA

TTAATAAATGGGCTTGAACTGAAAAAAAAAAAAA
```

Cell Stress Induced Alterations of BACE-1-AS Nuclear Retention Patterns: Different cell stressors like hypoxia, reoxygenation, oxidative stress and some proapoptotic factors have long been implicated in the pathogenesis of AD. These stressors enhance BACE-1 activity and Aβ generation (Tong et al., (2005) *Neural Transm* 112, 455-469). The nuclear retention of BACE-1-AS described above is reminiscent of the compartmental separation of CTN-RNA recently reported by Prasanth and colleagues (Prasanth et al., (2005) *Cell* 123, 249-263). This non-coding RNA transcript, like BACE-1-AS, is mainly located in nuclei and contains elements for adenosine-to-inosin editing, a key mechanism involved in its nuclear retention. CTN-RNA was shown to be cleaved under cell stress to produce the protein coding transcript mCAT2 mRNA. Based on these observations, we speculated that cell stress may release BACE-1-AS from the nucleus, and thereby modulate expression of BACE-1 mRNA. Cell stress is considered an important trigger that may contribute to the etiology of AD (Xue et al., (2006) *Neurosci Lett* 405, 231-235).

Figure 15B:
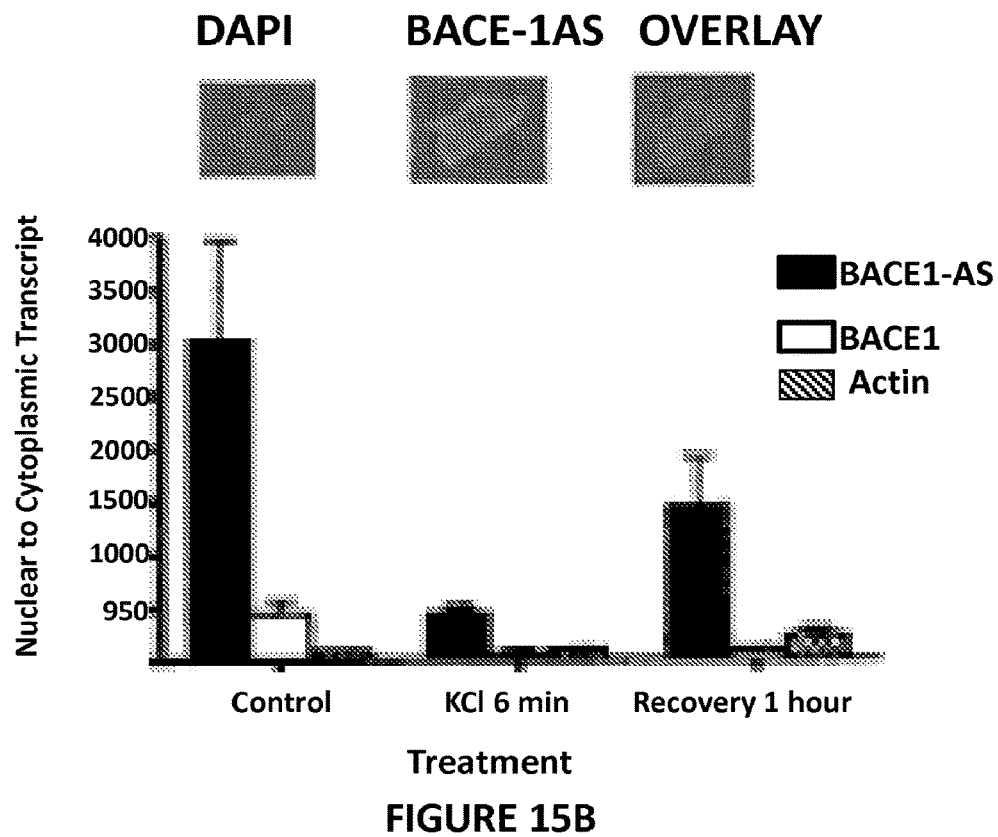

To investigate whether cell stress alters the nuclear retention of BACE-1-AS, we exposed SH-SY5Y cells to depolarizing concentrations of KCl (30 mM continuously for 5 mins), a known hyperosmotic cell stressor. This cell stress dramatically decreased the proportion of BACE-1-AS retained in the nucleus, implying that cell stress releases BACE-1-AS into the cytoplasm (FIG. 15B). To exclude the possibility that this shift in nuclear retention of BACE-1-AS after KCl treatment was related to nonspecific toxic phenomena and/or nuclear membrane breakdown, we treated cells with KCl, and then allowed a 60 min restoration period in regular medium. The proportional nuclear to cytoplasmic pattern of antisense transcript concentration returned to baseline.

There is considerable evidence that Aβ 1-42 has potent cell stressor effects. Indeed, Aβ 1-42 enhances BACE-1 mRNA and protein activity and thereby causes damage to the neuronal cells through various cell-stress related mechanisms (Tamagno et al., (2006) *Free Radic Biol Med* 41, 202-212). Also, direct injection of purified Aβ peptide into rat brain has been shown to cause oxidation of proteins and neuronal cell damage (Boyd-Kimball et al., 2005 *Neuroscience* 132, 313-324). Based on the above observations, we hypothesized that Aβ 1-42, at concentrations known to increase BACE-1 protein expression and thereby facilitate Aβ 1-42 synthesis (Tamagno et al., 2006), may also induce the nuclear release of BACE-1-AS.

Figure 15C:
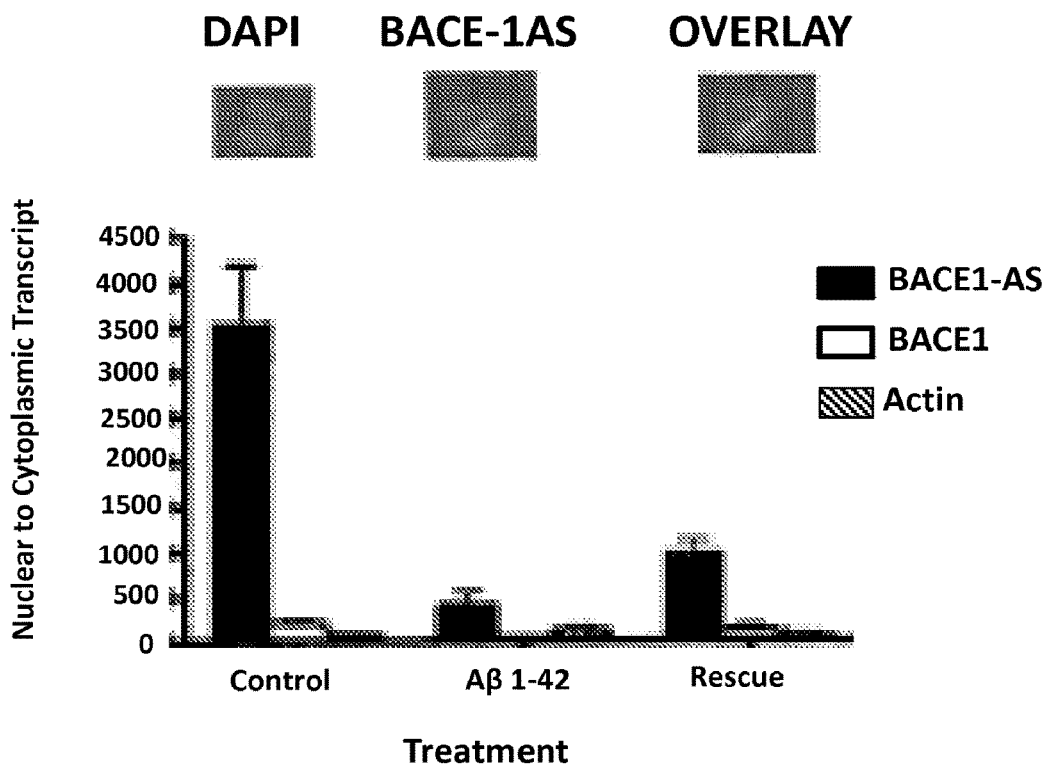
Figure 15D:
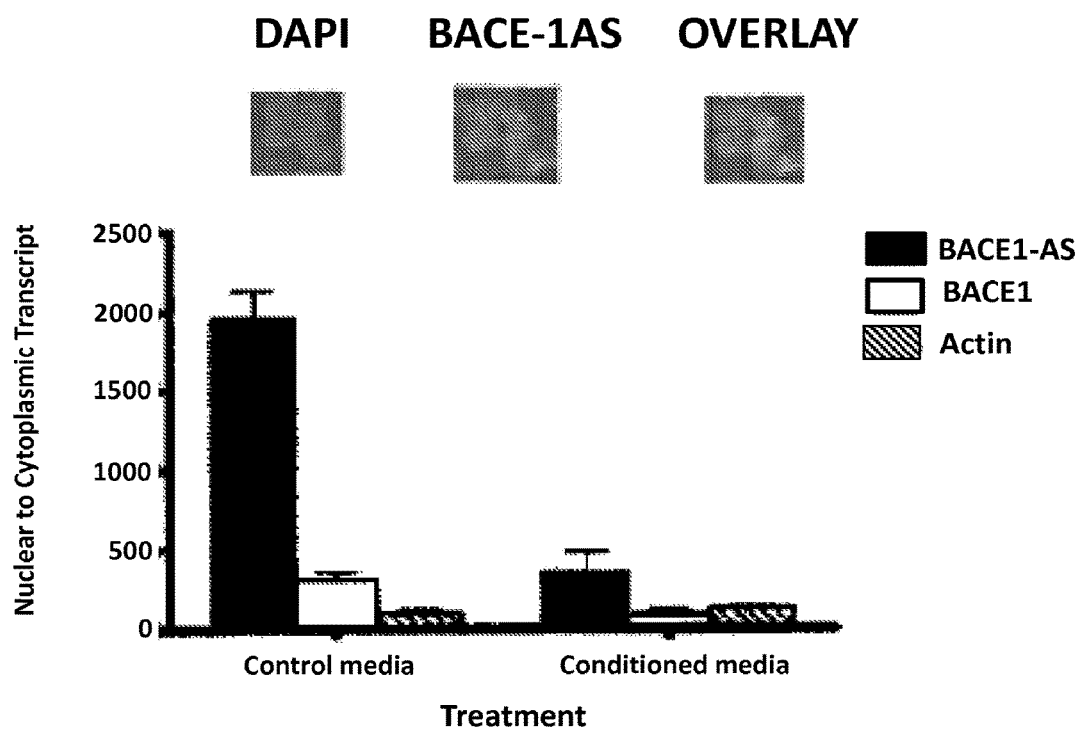
Figure 17:
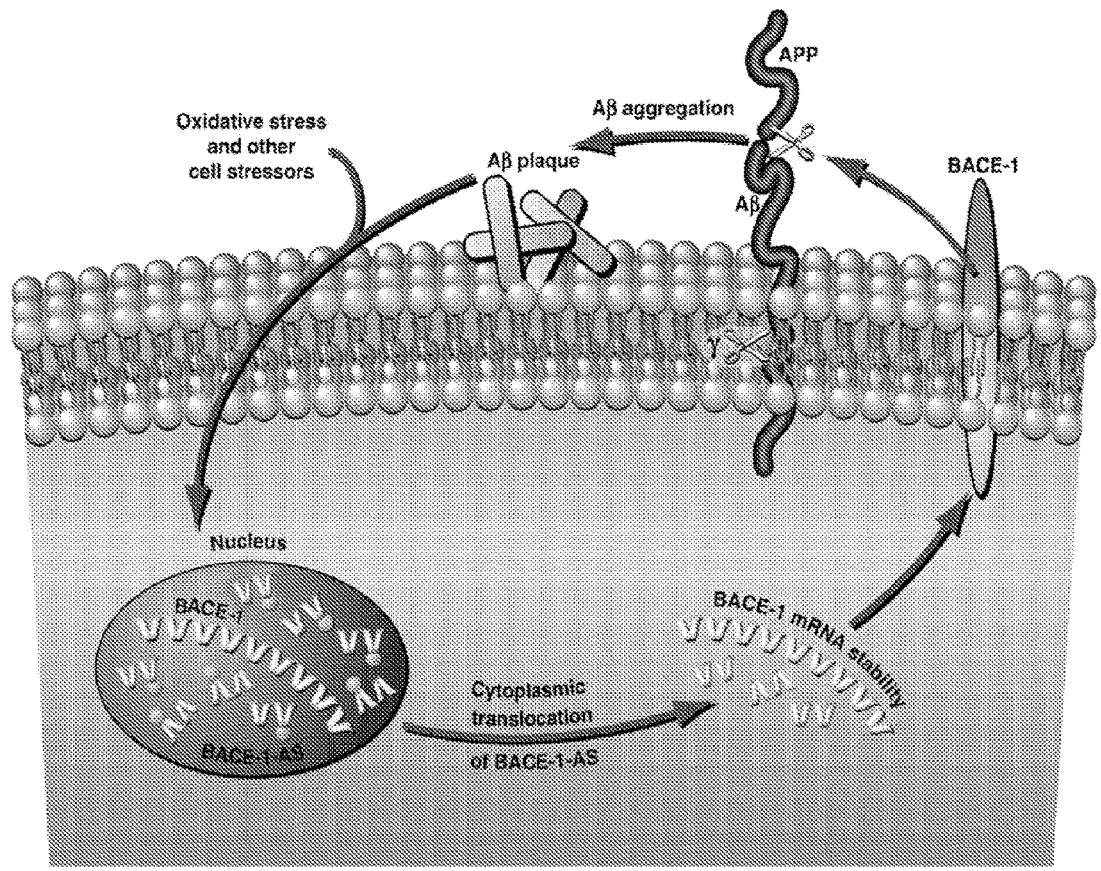
FIG. 17 is a schematic representation showing BACE-1-AS mediated regulation of BACE-1 and its proposed mechanism of involvement in Alzheimer's disease pathophysiology. BACE-1-AS RNA is mainly localized in nucleus during non-stress conditions throughout interaction with Cyclophilin-60(Cyp-60) and/or some other unknown proteins. Different kinds of cell stressors could potentially start series of events leading to translocation of BACE-1-AS, which then would cause increased in stability of BACE-1 mRNA. Increased levels of BACE-1 enhances the production of Aβ 1-42 leading to Aβ aggregation and formation of Aβ plaques. These later events are shown to be potent cell stressors and would act as a feed-forward mechanism leading to more BACE-1-AS release from nucleus.

Consistent with the above observations, synthetic Aβ 1-42 peptide (1 µM for 2 hours) released BACE-1-AS from the nucleus and increased its cytoplasmic concentrations in SH-SY5Y cells in a reversible manner (FIG. 15C). Furthermore, a 2-hour exposure of SH-SY5Y cells to conditioned media from CHO-7PA2 cells, which overexpress APP and contain significant levels Aβ 1-42 dimers and oligomers (Walsh et al., 2005 *Biochem Soc Trans* 33, 1087-1090.), also induced a similar translocation of BACE-1-AS transcript from nucleus to cytoplasm. As a control, mock conditioned media derived from parental CHO cells did not induce any translocation (FIG. 15D). Based on these observations, we propose that cell stress and/or Aβ 1-42 releases BACE-1-AS from the nucleus. Given that the expression of BACE-1-AS and BACE-1 mRNA are concordantly regulated, increased cytoplasmic BACE-1-AS would be expected to increase BACE-1 mRNA stability, contributing to further Aβ 1-42 production and resulting in a feed-forward loop (FIG. 17). Such a mechanism could provide an explanation for Alzheimer's disease progression.

Figure 16D:
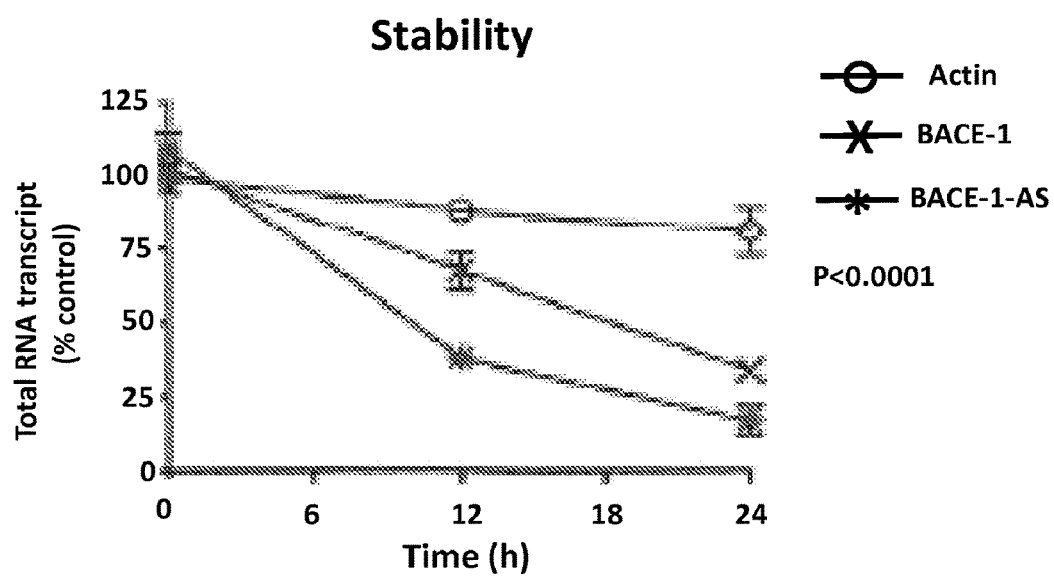

Stability of BACE-1 Sense and BACE-1-AS Antisense Transcripts: Given the concordant relationship between BACE-1-AS and BACE-1 mRNA, increased cytoplasmic concentrations of BACE-1-AS associated with cell stress or exposure to Aβ 1-42 likely increases the stability of BACE-1 and thereby increases Aβ 1-42 production. To test this hypothesis and assess potential mechanisms by which the increased cytoplasmic concentrations of BACE-1-AS may increase BACE-1 expression and function, we examined whether BACE-1-AS increases the stability and longevity of BACE-1 mRNA. To measure stability of the sense-antisense transcripts, we blocked new RNA synthesis with α-amanitin (5 µg/ml), and measured alterations in the levels of four species of RNA (18srRNA, β-Actin, BACE-1 and BACE-1-AS), over a 24 hour period. BACE-1-AS had a shorter basal half-life than BACE-1 mRNA, an observation that is in agreement with its regulatory properties (FIG. 16D). Additionally, blocking RNA synthesis with α-amanitin confirms that BACE-1-AS is a product of RNA polymerase II and further substantiates our RACE data described above. Indeed, 18s ribosomal RNA, which is a product of RNA polymerase III, was not affected by α-amanitin treatment.

Figure 16E:
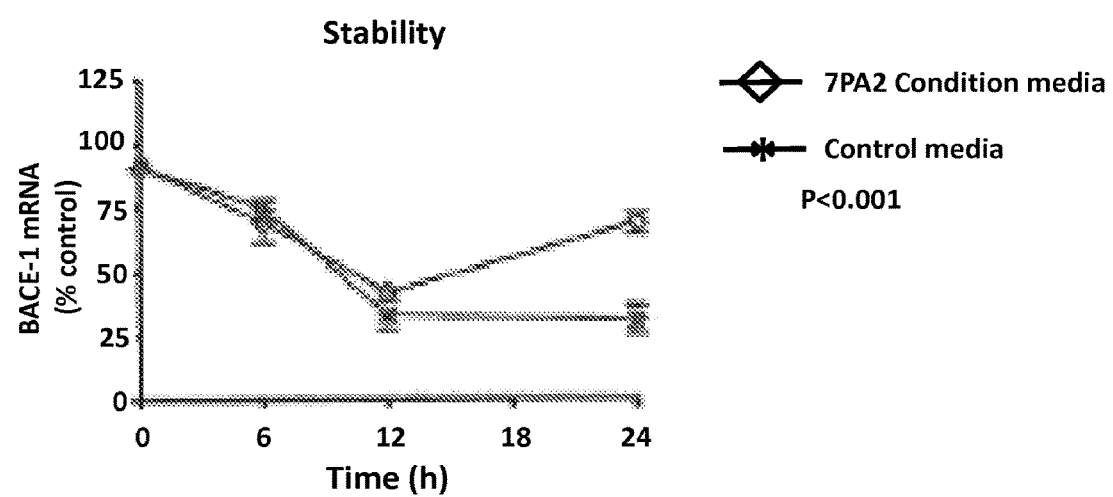

Interestingly, Aβ 1-42-mediated translocation of BACE-1-AS RNA during α-amanitin mediated blockade of RNA polymerase II significantly increases the BACE-1 stability (FIG. 16E). Collectively, these observations suggest a model of regulation for the BACE-1 mRNA by a non-coding NAT through sub-cellular compartmentalization/release of NAT, and resultant modulation of sense transcript stability and longevity (FIG. 17).

Figure 15E:
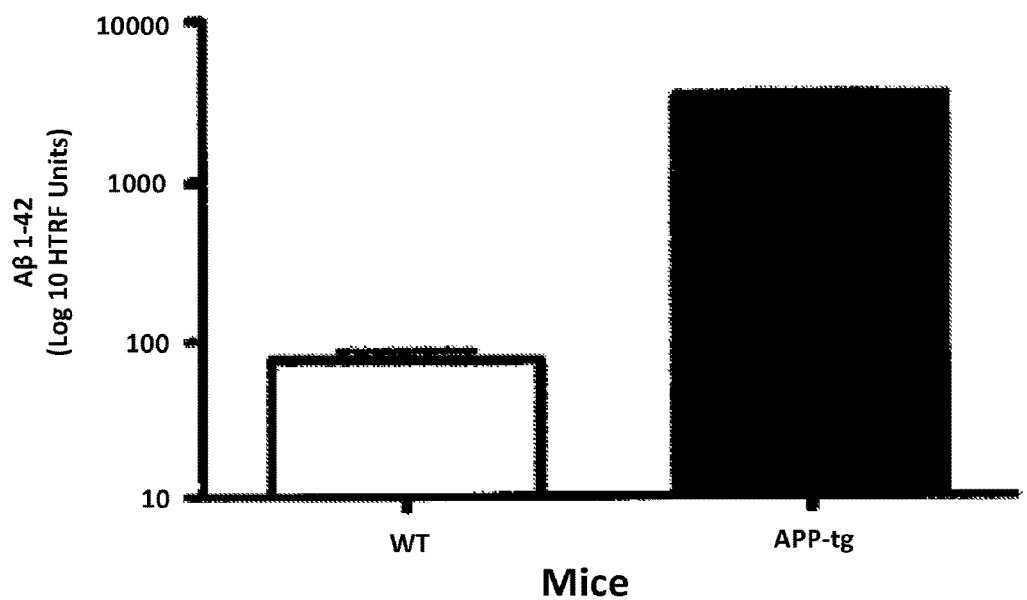
Figure 15F:
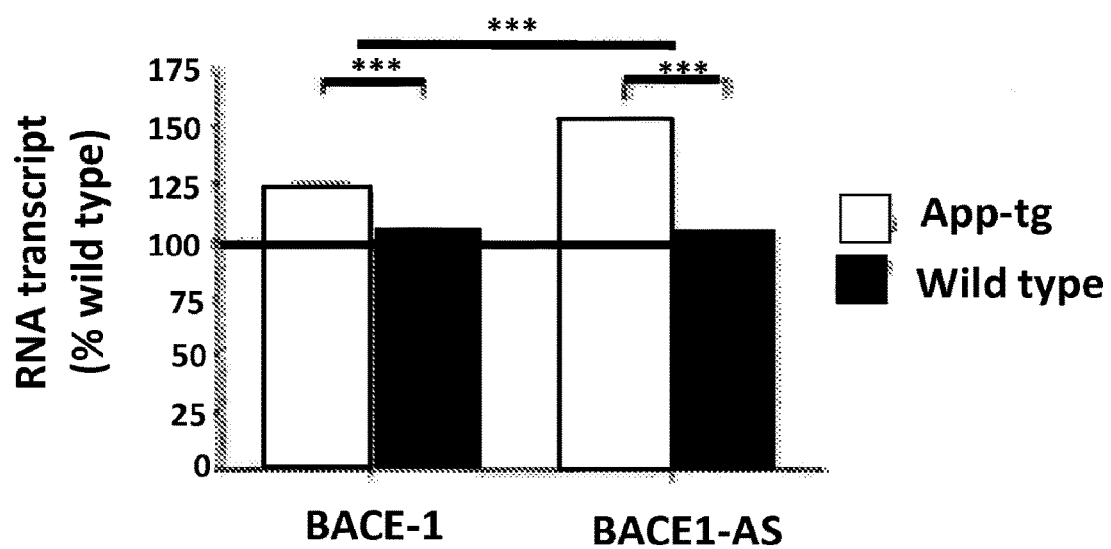

Increased Levels of BACE-1-AS in the Brains of APP Transgenic Mice: We postulate that increased levels of BACE-1-AS may stabilize BACE-1 mRNA and thereby increase the expression and function of BACE-1, contributing to increased Aβ 1-42 production and thereby facilitating the progression of AD-related pathophysiology. If this is indeed the case, mice that overexpress APP which have increased levels of Aβ 1-42 should display increased cytoplasmic concentrations of BACE-1-AS. We next investigated if increased Aβ 1-42 levels in APP overexpressing mice (Li et al., (2004a) *J. Neurochem* 89, 1308-1312) altered BACE-1 sense or antisense transcript expression. Whole brain, cerebellum and liver were excised from four male APP mice and four matched wild type control mice aged six weeks and used for protein and RNA extraction. As expected, APP mice had markedly increased (~300 fold) levels of Aβ 1-42 compared with wild-type mice, as shown by homogeneous time resolved fluorescence (HTRF) assay (FIG. 15F). More importantly, the BACE-1-AS transcript was up-regulated by about 45%, and BACE-1 mRNA was increased by about 25% in the brains of the APP mice compared with controls (FIG. 15E). These observations are consistent with the hypothesis that: i) BACE-1-AS and BACE-1 mRNA are concordantly regulated; ii) that elevated levels of Aβ 1-42 are associated with increased cytoplasmic concentrations of BACE-1-AS; and iii) that increased levels of BACE-1-AS are associated with increased levels of BACE-1, and concomitantly increased levels of Aβ 1-42. Finally, it may be noted that Aβ 1-42 accumulation in the AD brain is a chronic process and even a small positive feedback loop and elevation of BACE-1 expression may lead to a significant increase in amyloid deposition over time (Li et al., (2006) *Faseb J* 20, 285-292).

Conclusion: We have characterized a highly conserved and nuclear retained noncoding cis-antisense transcript for the BACE-1 and shown that it concordantly regulates the corresponding sense BACE-1 mRNA in vitro and in vivo. Several lines of evidence are presented supporting the notion that BACE-1 mRNA levels are concordantly regulated by this natural antisense transcript. We also provide evidence in support of a feed-forward model of Alzheimer's disease progression in which cellular stressors, including Aβ 1-42 exposure, releases this natural antisense transcript from the nucleus, thereby increasing BACE-1 activity and the production of Aβ 1-42. This is, to our knowledge, the first report directly implicating a noncoding RNA in the β-amyloid pathway.

TABLE 4

List of proteins which were co-purified with BACE-1 and BACE-1-AS transcripts

| # | Protein name | Repeats |
|---|---|---|
| | Proteins interacting with BACE-1 mRNA | |
| 1 | Ribonuclease inhibitor | 5 |
| 2 | Glyceraldehyde-3-phosphate dehydrogenase | 3 |
| 3 | ATP synthase beta chain, mitochondrial precursor | 3 |
| 4 | Eukaryotic initiation factor 4A-I | 2 |
| 5 | Heat shock protein HSP 90-alpha 2 | 2 |
| 6 | 60S ribosomal protein L4 | 2 |
| 7 | Chromobox protein homolog 1 | 2 |
| 8 | Phosphatidylethanolamine-binding protein 1 | 2 |
| 9 | 60S ribosomal protein L9 | 2 |
| 10 | Creatine kinase B-type | 2 |
| 11 | Lung cancer oncogene 7 | 2 |
| | Proteins interacting with BACE-1-AS RNA | |
| 1 | Calnexin precursor | 3 |
| 2 | Fructose-bisphosphate aldolase A | 3 |
| 3 | Ribonuclease inhibitor | 3 |
| 4 | Heterogeneous nuclear ribonucleoprotein U isoform a | 2 |
| 5 | Tubulin, beta 2 | 2 |
| 6 | Glutathione S-transferase P | 2 |
| 7 | Isoform 2 of Triosephosphate isomerase | 2 |
| 8 | Proliferating cell nuclear antigen | 2 |
| 9 | DNA replication licensing factor MCM4 | 2 |
| 10 | Tyrosine 3-monooxygenase/tryptophan 5-monooxygenase activation protein, beta polypeptide | 2 |
| 11 | 14-3-3 protein epsilon | 2 |
| 12 | Inorganic pyrophosphatase | 2 |
| 13 | NCL protein | 2 |
| 14 | DNA replication licensing factor MCM6 | 2 |

Proteins involved in translation processes (Bolded) were co-purified selectively with the BACE-1 mRNA. In contrast, proteins with a high nuclear abundance (Bolded) were exclusively associated with the BACE-1-AS transcript.

TABLE 5

List of siRNA, primers and probes and their sequences (F: Forward; R: Reverse, P: Probe).

| # | Primer name | Application | Sequence |
|---|---|---|---|
| 1 | Mouse BACE-1-AS_a-F | Real-time PCR | GTAGGCAGGGAAGCTAGTACTGA (SEQ ID NO: 33) |
| 2 | Mouse BACE-1-AS_a-R | Real-time PCR | AGAGGCTTGCAGTCCAGTTC (SEQ ID NO: 34) |
| 3 | Mouse BACE-1-AS_a-P | Real-time PCR | CCTGGAAGGAGAAACAG (SEQ ID NO: 35) |
| 4 | Mouse BACE-1-AS_b-F | Real-time PCR | TCTGCCTTGTAGATGAGGAGTCT (SEQ ID NO: 36) |
| 5 | Mouse BACE-1-AS_b-R | Real-time PCR | CCTGACTAGAGTCCTGCTGTTACTA (SEQ ID NO: 37) |

TABLE 5-continued

List of siRNA, primers and probes and their sequences (F: Forward; R: Reverse, P: Probe).

| # | Primer name | Application | Sequence |
|---|---|---|---|
| 6 | Mouse BACE-1-AS_b-P | Real-time PCR | CTCAGGCTCCTCACTACAG (SEQ ID NO: 38) |
| 7 | Mouse BACE-1 target site | Real-time PCR | CCACAGACGCTCAACATCCTGGTGG (SEQ ID NO: 39) |
| 8 | Mouse BACE-1-AS siRNA | siRNA | GCTCGAGCTGCTATCAGTTTCCAAT (SEQ ID NO: 40) |
| 9 | Human BACE-1-AS siRNA_a | siRNA | CCCTCTGACACTGTACCATCTCTTT (SEQ ID NO: 41) |
| 10 | Human BACE-1-AS siRNA_b | siRNA | AGAAGGGTCTAAGTGCAGACATCTG (SEQ ID NO: 42) |
| 11 | Human BACE-1-AS siRNA_c | siRNA | CCAGAAGAGAAAGGGCACT (SEQ ID NO: 43) |
| 12 | Human BACE-1 siRNA_a | siRNA | GAGCCTTTCTTTGACTCTCTGGTAA (SEQ ID NO: 44) |
| 13 | Human BACE-1 siRNA_b | siRNA | CCACGGAGAAGTTCCCTGATGGTTT (SEQ ID NO: 45) |
| 14 | BACEASCLON-F | 3'RACE | TAGCGAGGTGACAGCGTAGA (SEQ ID NO: 46) |
| 15 | BACEASCLON-R | 5'RACE | GGGGAAGAAACTTAACCTTGG (SEQ ID NO: 47) |
| 16 | HBAS-F | 3'RACE | TTGGCTGTTGCTGAAGAATG (SEQ ID NO: 48) |
| 17 | HBAS-R | 5'RACE | CAGAGCCCACCATCAAAAAC (SEQ ID NO: 49) |
| 18 | BACE1AS-F | 3'RACE | TACCATCTCTTTTACCCCCATCCT (SEQ ID NO: 50) |
| 19 | BACE1AS-R | 5'RACE | AAGCTGCAGTCAAATCCATCAA (SEQ ID NO: 51) |
| 20 | MBAS1-F | 3'RACE | GCAGAGTGGCAACATGAAGA (SEQ ID NO: 52) |
| 21 | MBAS1-R | 5'RACE | TTTCTCCTCCTGATCCGTAGAC (SEQ ID NO: 53) |
| 22 | MBASTest-F | 3'RACE | GTCTACGGATCAGGAGGAGAAA (SEQ ID NO: 54) |
| 23 | MBAS2-F | 3'RACE | CCCTAAGTGTTGGCATTTGG (SEQ ID NO: 55) |
| 24 | MBAS2-R | 5'RACE | GGGCATGATGGGAGAATAGA (SEQ ID NO: 56) |
| 25 | MBASTest-R | 5'RACE | CCAAATGCCAACACTTAGGG (SEQ ID NO: 57) |
| 26 | MBAS | siRNA | CAGAGAGACCTACTAGTTATT (SEQ ID NO: 58) |
| 27 | MBAS | siRNA | TAACTAGTAGGTCTCTCTGTT (SEQ ID NO: 59) |
| 28 | MBACE | siRNA | CACTGTGCGTGCCAACATTTT (SEQ ID NO: 60) |
| 29 | MBACE | siRNA | AATGTTGGCACGCACAGTGTT (SEQ ID NO: 61) |
| 30 | Negative control | siRNA | CCTCTCCACGCGCAGTACATT (SEQ ID NO: 62) |
| 31 | Negative control | siRNA | TGTACTGCGCGTGGAGAGGTT (SEQ ID NO: 63) |

Other Embodiments

It is to be understood that while the invention has been described in conjunction with the detailed description thereof, the foregoing description is intended to illustrate and not limit the scope of the invention. Other aspects, advantages, and modifications are within the scope of the following claims and their legal equivalents.

While the above specification contains many specifics, these should not be construed as limitations on the scope of the invention, but rather as examples of preferred embodiments thereof. Many other variations are possible. All references cited herein, are incorporated herein by reference.

What is claimed is:

1. A pharmaceutical composition comprising at least one modified nucleic acid molecule targeting a gene encoding a drug target for a neurological disorder, wherein the at least one modified nucleic acid molecule binds to a naturally-occurring anti-sense transcript of a sense strand of the targeted gene encoding the drug target, wherein the at least one modified nucleic acid molecule is about 10 to about 22 residues in length, wherein the at least one modified nucleic acid molecule comprises at least one modified base or sugar moiety, wherein the at least one modified nucleic acid molecule that binds to the naturally-occurring anti-sense transcript is complementary to the naturally-occurring anti-sense transcript, and wherein the targeted gene is selected from the group consisting of PINK1, HIF1α, Gnbp3g, Adrenomedullin AM1 receptor, 3-oxoacid CoA transferase, Cathepsin W and BACE1.

2. The pharmaceutical composition of claim 1, wherein the neurological disorder is Alzheimer's Disease.

3. The pharmaceutical composition of claim 2, wherein the drug target is BACE1.

4. The pharmaceutical composition of claim 3, wherein the naturally-occurring anti-sense transcript is selected from SEQ ID NOS: 64 and 65.

5. The pharmaceutical composition of claim 2, wherein the at least one modified nucleic acid molecule is selected from SEQ ID NOS: 4-6.

6. The pharmaceutical composition of claim 1, wherein the neurological disorder is Parkinson's Disease.

7. The pharmaceutical composition of claim 6, wherein the drug target is PINK1.

8. The pharmaceutical composition of claim 7, wherein the at least one modified nucleic acid molecule is selected from SEQ ID NOS: 1-3.

9. The pharmaceutical composition of claim 2, wherein the at least one nucleic acid molecule that binds to the sense transcript of the targeted gene is selected from SEQ ID NOS: 7 and 8.

10. A pharmaceutical composition comprising at least one modified nucleic acid molecule targeting a gene encoding a drug target for a neurological disorder, wherein the at least one modified nucleic acid molecule binds to a naturally-occurring anti-sense transcript of a sense strand of the targeted gene encoding the drug target, wherein the at least one modified nucleic acid molecule is about 10 to about 22 residues in length, wherein the at least one modified nucleic acid molecule comprises at least one modified base or sugar moiety, wherein the at least one modified nucleic acid molecule that binds to the naturally-occurring anti-sense transcript is complementary to the naturally-occurring anti-sense transcript, and wherein the neurological disorder is Alzheimer's Disease or Parkinson's Disease.

11. The pharmaceutical composition of claim 10, wherein the neurological disorder is Alzheimer's Disease and the drug target is BACE1.

12. The pharmaceutical composition of claim 11, wherein the naturally-occurring anti-sense transcript is selected from SEQ ID NOS: 64and 65.

13. The pharmaceutical composition of claim 11, wherein the at least one modified nucleic acid molecule is selected from SEQ ID NOS: 4- 6.

14. The pharmaceutical composition of claim 11, wherein the at least one nucleic acid molecule that binds to the sense transcript of the targeted gene is selected from SEQ ID NOS: 7and 8.

15. The pharmaceutical composition of claim 10, wherein the neurological disorder is Parkinson's Disease and the drug target is PINK1.

16. The pharmaceutical composition of claim 15, wherein the at least one modified nucleic acid molecule is selected from SEQ ID NOS: 1-3.

* * * * *

SEQUENCE LISTING

<160> NUMBER OF SEQ ID NOS: 67

<210> SEQ ID NO 1
<211> LENGTH: 25
<212> TYPE: DNA
<213> ORGANISM: Homo sapiens

<400> SEQUENCE: 1
ggaagctgta gctagaacat ctgtt                                          25

<210> SEQ ID NO 2
<211> LENGTH: 25
<212> TYPE: DNA
<213> ORGANISM: Homo sapiens

<400> SEQUENCE: 2
caggtaagta gtctcctcta tcatt                                          25

<210> SEQ ID NO 3
<211> LENGTH: 25
<212> TYPE: DNA
<213> ORGANISM: Homo sapiens

<400> SEQUENCE: 3
tctcaaccca aagcctgctt tgtta                                          25

<210> SEQ ID NO 4
<211> LENGTH: 25
<212> TYPE: DNA
<213> ORGANISM: Homo sapiens

<400> SEQUENCE: 4
ccctctgaca ctgtaccatc tcttt                                          25

<210> SEQ ID NO 5
<211> LENGTH: 25
<212> TYPE: DNA
<213> ORGANISM: Homo sapiens

<400> SEQUENCE: 5
agaagggtct aagtgcagac atctg                                          25

<210> SEQ ID NO 6
<211> LENGTH: 19
<212> TYPE: DNA
<213> ORGANISM: Homo sapiens

<400> SEQUENCE: 6
ccagaagaga aagggcact                                                 19

<210> SEQ ID NO 7
<211> LENGTH: 25
<212> TYPE: DNA
<213> ORGANISM: Homo sapiens

<400> SEQUENCE: 7
gagcctttct ttgactctct ggtaa                                          25

<210> SEQ ID NO 8
<211> LENGTH: 25
<212> TYPE: DNA
<213> ORGANISM: Homo sapiens

<400> SEQUENCE: 8
ccacggagaa gttccctgat ggttt                                              25

<210> SEQ ID NO 9
<211> LENGTH: 23
<212> TYPE: DNA
<213> ORGANISM: Homo sapiens

<400> SEQUENCE: 9
gaagatcaag atcattgctc ctc                                                23

<210> SEQ ID NO 10
<211> LENGTH: 27
<212> TYPE: DNA
<213> ORGANISM: Homo sapiens

<400> SEQUENCE: 10
ctgcacaaac ttggttagtt caatttt                                            27

<210> SEQ ID NO 11
<211> LENGTH: 25
<212> TYPE: DNA
<213> ORGANISM: Homo sapiens

<400> SEQUENCE: 11
actgcaatgc aatggtttaa atacc                                              25

<210> SEQ ID NO 12
<211> LENGTH: 40
<212> TYPE: DNA
<213> ORGANISM: Homo sapiens

<400> SEQUENCE: 12 tttttagta tgttctttaa tgctggatca cagacagctc                               40

<210> SEQ ID NO 13
<211> LENGTH: 30
<212> TYPE: DNA
<213> ORGANISM: Homo sapiens

<400> SEQUENCE: 13
atactctttt caatgggata ttatggttgt                                         30

<210> SEQ ID NO 14
<211> LENGTH: 32
<212> TYPE: DNA
<213> ORGANISM: Homo sapiens

<400> SEQUENCE: 14
tggtactggt tatttctaca tttatcttag tg                                      32

<210> SEQ ID NO 15
<211> LENGTH: 40
<212> TYPE: DNA
<213> ORGANISM: Homo sapiens

<400> SEQUENCE: 15
taacatgaca tttagggact caacatacat taaggtgatg                              40

<210> SEQ ID NO 16
<211> LENGTH: 21
<212> TYPE: DNA
<213> ORGANISM: Homo sapiens

```
<400> SEQUENCE: 16
gccactgaaa attcagcttc a                                        21

<210> SEQ ID NO 17
<211> LENGTH: 24
<212> TYPE: DNA
<213> ORGANISM: Homo sapiens

<400> SEQUENCE: 17
atccgcatcc aactattaaa atgg                                     24

<210> SEQ ID NO 18
<211> LENGTH: 20
<212> TYPE: DNA
<213> ORGANISM: Homo sapiens

<400> SEQUENCE: 18
ccagcccaac ccctaaagac                                          20

<210> SEQ ID NO 19
<211> LENGTH: 23
<212> TYPE: DNA
<213> ORGANISM: Homo sapiens

<400> SEQUENCE: 19
cctcaggaat cagctaaagc aaa                                      23

<210> SEQ ID NO 20
<211> LENGTH: 29
<212> TYPE: DNA
<213> ORGANISM: Homo sapiens

<400> SEQUENCE: 20
aaactgcaga acttttacct cggcatcca                                29

<210> SEQ ID NO 21
<211> LENGTH: 28
<212> TYPE: DNA
<213> ORGANISM: Homo sapiens

<400> SEQUENCE: 21
cggaattcag cgagaaccca gacctttc                                 28

<210> SEQ ID NO 22
<211> LENGTH: 28
<212> TYPE: DNA
<213> ORGANISM: Homo sapiens

<400> SEQUENCE: 22
cggaattcaa cttttacctc ggcatcca                                 28

<210> SEQ ID NO 23
<211> LENGTH: 29
<212> TYPE: DNA
<213> ORGANISM: Homo sapiens

<400> SEQUENCE: 23
aaactgcaga gcgagaaccc agacctttc                                29

<210> SEQ ID NO 24
<211> LENGTH: 28
<212> TYPE: DNA
<213> ORGANISM: Homo sapiens
```

```
<400> SEQUENCE: 24
cggaattcaa cttttacctc ggcatcca                                          28

<210> SEQ ID NO 25
<211> LENGTH: 29
<212> TYPE: DNA
<213> ORGANISM: Homo sapiens

<400> SEQUENCE: 25
aaactgcaga acttttacct cggcatcca                                         29

<210> SEQ ID NO 26
<211> LENGTH: 28
<212> TYPE: DNA
<213> ORGANISM: Homo sapiens

<400> SEQUENCE: 26
cgggatccag cgagaaccca gacctttc                                          28

<210> SEQ ID NO 27
<211> LENGTH: 21
<212> TYPE: DNA
<213> ORGANISM: Homo sapiens

<400> SEQUENCE: 27
aaaaccaacc ctgacgacag a                                                 21

<210> SEQ ID NO 28
<211> LENGTH: 18
<212> TYPE: DNA
<213> ORGANISM: Homo sapiens

<400> SEQUENCE: 28
gcagcgccat cagaggaa                                                     18

<210> SEQ ID NO 29
<211> LENGTH: 27
<212> TYPE: DNA
<213> ORGANISM: Homo sapiens

<400> SEQUENCE: 29
catcatgtgc gcttggaatc caagaga                                           27

<210> SEQ ID NO 30
<211> LENGTH: 22
<212> TYPE: DNA
<213> ORGANISM: Homo sapiens

<400> SEQUENCE: 30
gcatttcaag tatcccgtga tg                                                22

<210> SEQ ID NO 31
<211> LENGTH: 20
<212> TYPE: DNA
<213> ORGANISM: Homo sapiens

<400> SEQUENCE: 31
tgttgagtag ccgggatcct                                                   20

<210> SEQ ID NO 32
<211> LENGTH: 23
<212> TYPE: DNA
```

<213> ORGANISM: Homo sapiens

<400> SEQUENCE: 32
agcgggcttc ctacatgcct ccc                                          23

<210> SEQ ID NO 33
<211> LENGTH: 23
<212> TYPE: DNA
<213> ORGANISM: Mus musculus

<400> SEQUENCE: 33
gtaggcaggg aagctagtac tga                                          23

<210> SEQ ID NO 34
<211> LENGTH: 20
<212> TYPE: DNA
<213> ORGANISM: Mus musculus

<400> SEQUENCE: 34
agaggcttgc agtccagttc                                              20

<210> SEQ ID NO 35
<211> LENGTH: 17
<212> TYPE: DNA
<213> ORGANISM: Mus musculus

<400> SEQUENCE: 35
cctggaagga gaaacag                                                 17

<210> SEQ ID NO 36
<211> LENGTH: 23
<212> TYPE: DNA
<213> ORGANISM: Mus musculus

<400> SEQUENCE: 36
tctgccttgt agatgaggag tct                                          23

<210> SEQ ID NO 37
<211> LENGTH: 25
<212> TYPE: DNA
<213> ORGANISM: Mus musculus

<400> SEQUENCE: 37
cctgactaga gtcctgctgt tacta                                        25

<210> SEQ ID NO 38
<211> LENGTH: 19
<212> TYPE: DNA
<213> ORGANISM: Mus musculus

<400> SEQUENCE: 38
ctcaggctcc tcactacag                                               19

<210> SEQ ID NO 39
<211> LENGTH: 25
<212> TYPE: DNA
<213> ORGANISM: Mus musculus

<400> SEQUENCE: 39
ccacagacgc tcaacatcct ggtgg                                        25

<210> SEQ ID NO 40
<211> LENGTH: 25

```
<212> TYPE: DNA
<213> ORGANISM: Mus musculus

<400> SEQUENCE: 40
gctcgagctg ctatcagttt ccaat                                 25

<210> SEQ ID NO 41
<211> LENGTH: 25
<212> TYPE: DNA
<213> ORGANISM: Homo sapiens

<400> SEQUENCE: 41
ccctctgaca ctgtaccatc tcttt                                 25

<210> SEQ ID NO 42
<211> LENGTH: 25
<212> TYPE: DNA
<213> ORGANISM: Homo sapiens

<400> SEQUENCE: 42
agaagggtct aagtgcagac atctg                                 25

<210> SEQ ID NO 43
<211> LENGTH: 19
<212> TYPE: DNA
<213> ORGANISM: Homo sapiens

<400> SEQUENCE: 43
ccagaagaga aagggcact                                        19

<210> SEQ ID NO 44
<211> LENGTH: 25
<212> TYPE: DNA
<213> ORGANISM: Homo sapiens

<400> SEQUENCE: 44
gagcctttct ttgactctct ggtaa                                 25

<210> SEQ ID NO 45
<211> LENGTH: 25
<212> TYPE: DNA
<213> ORGANISM: Homo sapiens

<400> SEQUENCE: 45
ccacggagaa gttccctgat ggttt                                 25

<210> SEQ ID NO 46
<211> LENGTH: 20
<212> TYPE: DNA
<213> ORGANISM: Homo sapiens

<400> SEQUENCE: 46
tagcgaggtg acagcgtaga                                       20

<210> SEQ ID NO 47
<211> LENGTH: 21
<212> TYPE: DNA
<213> ORGANISM: Homo sapiens

<400> SEQUENCE: 47
ggggaagaaa cttaaccttg g                                     21

<210> SEQ ID NO 48
```

```
<211> LENGTH: 20
<212> TYPE: DNA
<213> ORGANISM: Homo sapiens

<400> SEQUENCE: 48
ttggctgttg ctgaagaatg                                               20

<210> SEQ ID NO 49
<211> LENGTH: 20
<212> TYPE: DNA
<213> ORGANISM: Homo sapiens

<400> SEQUENCE: 49
cagagcccac catcaaaaac                                               20

<210> SEQ ID NO 50
<211> LENGTH: 24
<212> TYPE: DNA
<213> ORGANISM: Homo sapiens

<400> SEQUENCE: 50
taccatctct tttaccccca tcct                                          24

<210> SEQ ID NO 51
<211> LENGTH: 22
<212> TYPE: DNA
<213> ORGANISM: Homo sapiens

<400> SEQUENCE: 51
aagctgcagt caaatccatc aa                                            22

<210> SEQ ID NO 52
<211> LENGTH: 20
<212> TYPE: DNA
<213> ORGANISM: Homo sapiens

<400> SEQUENCE: 52
gcagagtggc aacatgaaga                                               20

<210> SEQ ID NO 53
<211> LENGTH: 22
<212> TYPE: DNA
<213> ORGANISM: Homo sapiens

<400> SEQUENCE: 53
tttctcctcc tgatccgtag ac                                            22

<210> SEQ ID NO 54
<211> LENGTH: 22
<212> TYPE: DNA
<213> ORGANISM: Homo sapiens

<400> SEQUENCE: 54
gtctacggat caggaggaga aa                                            22

<210> SEQ ID NO 55
<211> LENGTH: 20
<212> TYPE: DNA
<213> ORGANISM: Homo sapiens

<400> SEQUENCE: 55
ccctaagtgt tggcatttgg                                               20
```

```
<210> SEQ ID NO 56
<211> LENGTH: 20
<212> TYPE: DNA
<213> ORGANISM: Homo sapiens

<400> SEQUENCE: 56
gggcatgatg ggagaataga                                              20

<210> SEQ ID NO 57
<211> LENGTH: 20
<212> TYPE: DNA
<213> ORGANISM: Homo sapiens

<400> SEQUENCE: 57
ccaaatgcca acacttaggg                                              20

<210> SEQ ID NO 58
<211> LENGTH: 21
<212> TYPE: DNA
<213> ORGANISM: Homo sapiens

<400> SEQUENCE: 58
cagagagacc tactagttat t                                            21

<210> SEQ ID NO 59
<211> LENGTH: 21
<212> TYPE: DNA
<213> ORGANISM: Homo sapiens

<400> SEQUENCE: 59
taactagtag gtctctctgt t                                            21

<210> SEQ ID NO 60
<211> LENGTH: 21
<212> TYPE: DNA
<213> ORGANISM: Homo sapiens

<400> SEQUENCE: 60
cactgtgcgt gccaacattt t                                            21

<210> SEQ ID NO 61
<211> LENGTH: 21
<212> TYPE: DNA
<213> ORGANISM: Homo sapiens

<400> SEQUENCE: 61
aatgttggca cgcacagtgt t                                            21

<210> SEQ ID NO 62
<211> LENGTH: 21
<212> TYPE: DNA
<213> ORGANISM: Homo sapiens

<400> SEQUENCE: 62
cctctccacg cgcagtacat t                                            21

<210> SEQ ID NO 63
<211> LENGTH: 21
<212> TYPE: DNA
<213> ORGANISM: Homo sapiens

<400> SEQUENCE: 63
tgtactgcgc gtggagaggt t                                            21
```

<210> SEQ ID NO 64
<211> LENGTH: 1055
<212> TYPE: DNA
<213> ORGANISM: Homo sapiens

<400> SEQUENCE: 64

```
tctagcgagg tgacagcgta gaaccaggcg gggtccctcc cattacatac tactgctctg        60
gcctctgccc gtcatagttg ccatctggtc atttccttcc cataaagcca gggctcaccg       120
caacctccac cgtcctgagt taaagtgatt ctcctgtctc agcccctga gtagctagga       180
ttacaggcgt gcgccaccac acccagctaa ttttttgtact tttagtgagag atgggatttc       240
accctgttgg tcaggctggt cttgaactcc tgacctagtg atctgcccac cttggcctcc       300
caaagtgctg ggattacagg cgtgagccac cacgcctggc taggggaaga gtgcttttaa       360
gagctctgag tagaagggtc taagtgcaga catcttggct gttgctgaag aatgtgactc       420
tcaccgcctc cctctgacac tgtaccatct cttttacccc catccttagt ccactcacgg       480
aggaggctgc cttgatggat ttgactagca gcttcaaaca ctttcttggg caaacgaagg       540
ttggtggtgc cactgtccac aatgctcttg tcatagttgt actaagaggg aaaagagaga       600
gttaaaagag tcaaaaggtt tttgatgctg ggctctgggc agtagggggt tactgctggg       660
gccccagctg ggttggcatc ttggcttttgg cacctcctaa gtgtacctgc ttggacaagt       720
taacctctgt gcctcagttc cttcatctct aaagtgagga taaaaatagc acctacctca       780
aagggttatt gtaaggatta aataaatcag caatgtaaag cacttagaat cgtgcccagc       840
agagagaagg cacttggtaa atgtttattc ttgttaatct tgggtgggca ggtagtctcc       900
aaacttgaaa aaaaaaaaaa agcaccttat aaatcgtgcc ccgccagaag agaaagggca       960
ctttgggaaa aatggtttta attcccttgt ttaaattctt tgggggtggg gggccaaggt      1020
taagtttctt ccccaaaaac ctttggaaaa aaatt                                  1055
```

<210> SEQ ID NO 65
<211> LENGTH: 250
<212> TYPE: DNA
<213> ORGANISM: Homo sapiens

<400> SEQUENCE: 65

```
cttttaagag ctctgagtag aagggtctaa gtgcagacat cttggctgtt gctgaagaat        60
gtgactctca ccgcctccct ctgacactgt accatctctt ttaccccat ccttagtcca       120
ctccacggag gaggctgcct tgatggattt gactgcagct tcaaacactt tcttgggcaa       180
acgaaggttg gtggtgccac tgtccacaat gcctcttgtc atagttgtac taagagggaa       240
aaaaaaaaaa                                                               250
```

<210> SEQ ID NO 66
<211> LENGTH: 1685
<212> TYPE: DNA
<213> ORGANISM: Homo sapiens

<400> SEQUENCE: 66

```
gtctacggat caggaggaga aagtgagata ctggcctcat aaagctgtga gtgggcatgg        60
tggctcacac tgcctgtggt cccagaactt agaaggctaa ggcatgaagt tgtcaagttc       120
aatgctaacc tgggctacgt tcatgacccc atctcaaaaa aaaaaaaaaa aaaaaaaag       180
gcatctcaat gccaagtcaa cagagcagtg gtttgtaagc gcctgatggg aaggatctac       240
gtatctttag ggcttgctga ggagtgtgac tgtcactgac cgaggaggct gccttgatgg       300
```

```
acttgacggc agcttcaaat actttcttgg gcaagcgaag gttggtggtc ccactgtcca    360
caatgctctt gtcgtagttg tactgaggag agagggggg agaggtggga ggggtgaatc    420
tgacagctaa gcatcctact ggggttggca tcttagcttt cccattttgt atatgtgcgt    480
ccttgggcac gttgcttaac ctctgtgtac ctgttctctt gttctaaatt gaagataata    540
acagtgccta cctcaaaggt taccataagg attacatagg tcaaaaggct gaaagcacta    600
agtaggtcct ggcagatccc aggcacttgg taagtactaa cttcgtcacc ttgtgcgggt    660
aggtgttctc taaatctaaa gcagaaatgc cttgtgtggt atttgtaact tctagtactt    720
ttatgtagtt attctcattc accatacatt ataatgaga gaagggtggc tcagcacgca    780
caaagccatg agcttgagct ctgatgctgc atggtggtat atgcctgtag agagacactt    840
gagagtcaga gaaaggagga ccaggagttc aaggtcatct ttagctacct agcaagtctg    900
aggtcagcgt gggctacata agatcctcaa aaaagccaaa aagggggct gttgagatag    960
gtaagggcac ctgctaccaa gtctgatgac ctgagttcaa ccccagagag acctactagt   1020
tactgaaaat tgtcctctaa cctccataca caagctgtgg cacatgcccc atcctcatcc   1080
caataaatgt aaaacaaaat ctagggaaag agaccctaag tgttggcatt tgggtatgcc   1140
aagcataacg actaacactt catacattgg ctttgacctt tacagtctgt gagaacgctt   1200
gtgtatttct acctctgcct tgtagatgag gagtctggca ctgtagtgag gagcctgagg   1260
gcacttagta acagcaggac tctagtcagg tccaacctct gcctcacaaa agccttgccc   1320
aaggctgaag aggcagtgac tagagtccag aaaggaactc tttcatgttt tcattactat   1380
acttaagtca tgtggtccag gctctgtgac tgctctgcca ggccccgccc ttcaccttag   1440
ggattgcctc gtgatcctgt gcttccaccc tcatggctct cacacactgt gagactcccc   1500
ttatgctcac gagaatcccc tccatcccat tacctccttg cagtccatct tgagatcttg   1560
accattgatt tccacacgta caatgatcac ttcataatac cactcccgcc ggatgggtgt   1620
gtaccagaga ctgcccgtgt atagcgagtg gtcgatacca ccaatgatct aaaagaaaaa   1680
aaaaa                                                              1685
```

<210> SEQ ID NO 67
<211> LENGTH: 2028
<212> TYPE: DNA
<213> ORGANISM: Homo sapiens

<400> SEQUENCE: 67

```
gtctacggat caggaggaga aagtgagata ctggcctcat aaagctgtga gtgggcatgg     60
tggctcacac tgcctgtggt cccagaactt agaaggctaa ggcatgaagt tgtcaagttc    120
aatgctaacc tgggctacgt tcatgacccc atctcaaaaa aaaaaaaaa aaaaaaaag    180
gcatctcaat gccaagtcaa cagagcagtg gtttgtaagc gcctgatggg aaggatctac    240
gtatctttag ggcttgctga ggagtgtgac tgtcactgac cgaggaggct gccttgatgg    300
acttgacggc agcttcaaat actttcttgg gcaagcgaag gttggtggtc ccactgtcca    360
caatgctctt gtcgtagttg tactgaggag agagggggg agaggtggga ggggtgaatc    420
tgacagctaa gcatcctact ggggttggca tcttagcttt cccattttgt atatgtgcgt    480
ccttgggcac gttgcttaac ctctgtgtac ctgttctctt gttctaaatt gaagataata    540
acagtgccta cctcaaaggt taccataagg attacatagg tcaaaaggct gaaagcacta    600
agtaggtcct ggcagatccc aggcacttgg taagtactaa cttcgtcacc ttgtgcgggt    660
```

-continued

```
aggtgttctc taaatctaaa gcagaaatgc cttgtgtggt atttgtaact tctagtactt    720
ttatgtagtt attctcattc accatacatt ataatggaga gaagggtggc tcagcacgca    780
caaagccatg agcttgagct ctgatgctgc atggtggtat atgcctgtag agagacactt    840
gagagtcaga gaaaggagga ccaggagttc aaggtcatct ttagctacct agcaagtctg    900
aggtcagcgt gggctacata agatcctcaa aaaagccaaa aaaggggct gttgagatag     960
gtaagggcac ctgctaccaa gtctgatgac ctgagttcaa ccccagagag acctactagt   1020
tactgaaaat tgtcctctaa cctccataca caagctgtgg cacatgcccc atcctcatcc   1080
caataaatgt aaaacaaaat ctagggaaag agaccctaag tgttggcatt tgggtatgcc   1140
aagcataacg actaacactt catacattgg ctttgacctt tacagtctgt gagaacgctt   1200
gtgtatttct acctctgcct tgtagatgag gagtctggca ctgtagtgag gagcctgagg   1260
gcactctagt aacagcagga ctctagtcag gtccaacctc tgcctcacaa aagccttgcc   1320
caaggctgaa gaggcagtga ctagagtcca gaaaggaact cttcatgtt ttcattacta    1380
tacttaagtc atgtggtcca ggctctgtga ctgctctgcc aggccccgcc cttcaccta    1440
gggattgcct cgtgatcctg tgcttccacc ctcatggctc tcacacactg tgagactccc   1500
cttatgctca cgagaatccc ctccatccca ttacctcctt gcagtccatc ttgagatctt   1560
gaccattgat ttccacacgt acaatgatca cttcataata ccactcccgc cggagtgggt   1620
gtgtaccaga gactgcccgt gtatagcgag tggtcgatac caccaatgat ctaaaagaaa   1680
aagagacaga cacctatgtc ctagcacaga aggagagcaa gttacccaag actaaataat   1740
aagatcagcc atttcttggg gtgccaagat tctctctaat ctcccatcat gccccatgca   1800
tggtaatatt tagtttccta aatgtgttca ggagaagaaa cacatcggga ttatttgtat   1860
caaaatctat agcccttgac cgaaagttat ttaagcccta agctagtaca ataaacgtgg   1920
aatgaactga ttgtatgctg ctttcataca ttttcttgtc tttgcttgtt ggagaatact   1980
tgttactgtc ctaattaata aatgggcttg aactgaaaaa aaaaaaaa               2028
```